US009644012B2

(12) United States Patent
Johansson et al.

(10) Patent No.: US 9,644,012 B2
(45) Date of Patent: May 9, 2017

(54) PRODUCTION OF PROTEINS AND POLYPEPTIDES

(75) Inventors: Jan Johansson, Stockholm (SE); Anna Rising, Uppsala (SE); My Hedhammar, Stockholm (SE); Kerstin Nordling, Knivsta (SE)

(73) Assignee: SPIBER TECHNOLOGIES AB, Uppsala (SE)

( * ) Notice: Subject to any disclaimer, the term of this patent is extended or adjusted under 35 U.S.C. 154(b) by 395 days.

(21) Appl. No.: 13/634,519

(22) PCT Filed: Oct. 27, 2010

(86) PCT No.: PCT/SE2010/051163
§ 371 (c)(1),
(2), (4) Date: Nov. 27, 2012

(87) PCT Pub. No.: WO2011/115538
PCT Pub. Date: Sep. 22, 2011

(65) Prior Publication Data
US 2013/0065278 A1    Mar. 14, 2013

(30) Foreign Application Priority Data

Mar. 18, 2010  (EP) ..................... 10156927
Apr. 21, 2010  (SE) ................... PCT/SE2010/050439

(51) Int. Cl.
*C07K 14/435* (2006.01)
*C12N 15/62* (2006.01)
(52) U.S. Cl.
CPC ........ *C07K 14/43518* (2013.01); *C12N 15/62* (2013.01)
(58) Field of Classification Search
CPC .......................... C17K 14/43518; C12N 15/62
See application file for complete search history.

(56) References Cited

U.S. PATENT DOCUMENTS 5,985,261 A  * 11/1999 White ..................... A61K 38/44
                                                    424/450
6,017,735 A  *  1/2000 O'Hare et al. ............... 435/69.7

FOREIGN PATENT DOCUMENTS

| EP | 2243792 A1 | 10/2010 |
|---|---|---|
| WO | WO 03/057727 A1 | 7/2003 |
| WO | WO 2005/111068 A2 | 11/2005 |
| WO | WO 2007/078239 A2 | 7/2007 |
| WO | WO 2008/113145 A1 | 9/2008 |
| WO | WO 2008/154547 A2 | 12/2008 |
| WO | WO 2010/123450 A1 | 10/2010 |

OTHER PUBLICATIONS

Rising et al., N-Terminal Nonrepetitive Domain Common to Dragline, Flagelliform, and Cylindriform Spider Silk Proteins., Biomacromolecules (2006), vol. 7, pp. 3120-3124.*
LaVallie et al., Thioredoxin and Related Proteins as Multifunctional Fusion Tags for Soluble Expression in *E. coli*., Methods in Molecular Biology™ (2003), vol. 205, pp. 119-140.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Q05H60 major ampullate spidroin MaSP1 (last viewed on Feb. 7, 2015).*
Stark et al., Macroscopic Fibers Self-Assembled from Recombinant Miniature Spider Silk Proteins., Biomacromolecules (2007), vol. 8, pp. 1695-1701.*
Hedhammar et al. Structural properties of recombinant nonrepetitive and repetitive parts of major ampullate spidroin 1 from Euprosthenops australis: implications for fiber formation., Biochemistry (2008), vol. 47(11), pp. 3407-3417.*
Branden and Tooze, Introduction to Protein Structure (1999), 2nd edition, Garland Science Publisher, pp. 3-12.*
Askarieh et al., "Self-assembly of spider silk proteins is controlled by a pH-sensitive relay", Nature, vol. 465, May 13, 2010, pp. 236-239.
Ayoub et al., "Blueprint for a High-Performance Biomaterial: Full-Length Spider Dragline Silk Genes", PLos One, Jun. 2007, Issue 6, e514, pp. 1-13.
Bittencourt et al., "Spidroins from the Brazilian spider *Nephilengys cruentata* (Araneae: Nephilidae)", Science Direct, Comparative Biochemistry and Physiology, Part B 147, (2007), pp. 597-606.
Dicko et al., "Spider Silk Protein Refolding is Controlled by Changing pH", Biomacromolecules 2004, pp. 704-710.
Gaines IV et al., "Identification and characterization of multiple Spidroin 1 genes encoding major ampullate silk proteins in Nephila clavipes", Insect Molecular Biology (2008), 17(5), pp. 465-474.
Grip, "Recombinant Production and Determinants for Fiber Formation", Artificial Spider Silk, Doctoral Thesis, Swedish University of Agricultural Science, Uppsala, 2008.
Hedhammer et al., "Structural Properties of Recombinant Nonrepetitive and Repetitive Parts of Major Ampullate Spidroin 1 from Euprosthenops australis: Implications for Fiber Formation", Biochemistry 2008, 47, pp. 3407-3417.
Lewis et al., "Expression and Purification of Spider Silk Protein: A New Strategy for Producing Repetitive Proteins", Protein Expression and Purification 7, (1996), pp. 400-406.
Motriuk-Smith et al., "Analysis of the Conserved N-Terminal Domains in Major Ampullate Spider Proteins", Biomacromolecules 2005,6, pp. 3152-3159.
Pan et al., "Cloning and prokaryotic expression of major ampullate spidroin gene of spider", Sheng Wu Gong Cheng Xue Bao, May 2007, Abstract.

(Continued)

*Primary Examiner* — Alexander Kim
(74) *Attorney, Agent, or Firm* — Birch, Stewart, Kolasch & Birch, LLP

(57) ABSTRACT

A method of producing a desired non-spidroin protein or polypeptide is comprising the steps of expressing in a suitable host a fusion protein, obtaining a mixture containing the fusion protein, and optionally isolating the fusion protein. The fusion protein is comprising at least one solubility-enhancing moiety which is derived from the N-terminal (NT) fragment of a spider silk protein. It is further comprising at least one moiety which is a desired non-spidroin protein or polypeptide. Each solubility-enhancing moiety is linked directly or indirectly to the desired protein or polypeptide moiety.

18 Claims, 6 Drawing Sheets

(56) References Cited

OTHER PUBLICATIONS

Rising et al., "N-Terminal nonrepetitive domain common to dragline, flagelliform, and cylinderiform spider silk proteins", (2006) Biomacromolecules 7: pp. 3120-3124, Nucleotide Sequence.
Rising et al., "N-Terminal Nonrepetitive Domain Common to Dragline, Flagelliform, and Cylinderiform Spider Silk Proteins", Biomacromolecules, 2006, 7, pp. 3120-3124.
Rising et al., "N-Terminal Nonrepetitive Domain Common to Dragline, flagelliform, and cylinderiform Spider Silk Proteins", Sequence, Creation Date: Oct. 6, 2006.
Rising, "Molecular Properties and Recombinant Expression", Spider Dragline Silk, Doctoral Thesis, Swedish University of Agricultural Science, Uppsala, 2007.
Stark et al., "Macroscopic Filbers Self-Assembled from Recombinant Miniature Spider Silk Proteins", Biomacromolecules 2007, 8, pp. 1698-1701.
Extended European Search Report, dated Nov. 29, 2013, for European Application No. 10848078.1.
Lin et al., "Solution structure of eggcase silk protein and its implications for silk fiber formation", PNAS, vol. 106, No. 22, Jun. 2, 2009, pp. 8906-8911.

\* cited by examiner

| | | |
|---|---|---|
| Ea MaSp1 | SHTTPWTNPGLAENFMNSFMQGLSSMPGFTASQLDDMSTIAQSMVQSIQSLAAQGRTSPNKLQALNMAFA |
| Lg MaSp1 | QANTPWSSKANADAFINSFISSAQNTGSFSQDQMDDMSLIGNTLMTAMDNMG---GRITPSKLQALDMAFA |
| Lh MaSp1 | QANTPWSSKANADAFINSFISAASNTGSFSQDQMEDMSLIGNTLMAAMDNMG---GRITPSKLQALDMAFA |
| Nc MaSp1 | --QNTPWSSTELADAFINAFMNEAGRTGAFTADQLDDMSTIGDTIKTAMDKMARSNKSSKGKLQALNMAFA |
| At MaSp2 | QGATPWENSQLAESFISRFLRFIGQSGAFSPNQLDDMSSIGDTLKTAIEKMAQSRKSSKSKLQALNMAFA |
| Lg MaSp2 | ---LRWSSKDNADRFINAFLQAASNSGAFSSDQVDDMSVIGNTLMTAMDNMG---GRITPSKLQALDMAFA |
| Lh MaSp2 | QANTPWSSKENADAFIGAFMNAASQSGAFSSDQIDDMSVISNTLMAAMDNMG---GRITQSKLQALDMAFA |
| Nim MaSp2 | QANTPWSDTATADAFIQNFLGAVSGSGAFTPDQLDDMSTVGDTIMSAMDKMARSNKSSKSKLQALNMAFA |
| Nc MaSp2 | QARSPWSDTATADAFIQNFLAAVSGSGAFTSDQLDDMSTIGDTIMSAMDKMARSNKSSQHKLQALNMAFA |
| Ab CySp1 | AVPSVFSSPNLASGFLQCLTFGIGNSPAFPTQEQQDLDAIAQVILNAVSSNTGATASAR--AQALSTALA |
| Ncl CySp1 | PVPSVFSSPSLASGFLQCLTTGIGLSPAFPFQEQQDLDDLAKVILSAVTSNTDTSKSAR--AQALSTALA |
| Lh TuSp1 | ASVNIFNSPNAATSFLNCLRSNIESSPAFPFQEADLDSIAEVILSDVSS-VNTASSAT--SLALSTALA |
| Nc flag | IANSPFSNPNTAEAFARSFVSNIVSSGEFGAQGAEDFDDIIQSLIQAQ-SMGKGRHDTKAKAKAMQVALA |
| Nlm flag | IVNSPFSNPNTAEAFARSFVSNVVSSGEFGAQGAEDFDDIIQSLIQAQ-SMGKGRHDTKAKAKAMQVALA |

| | | |
|---|---|---|
| Ea MaSp1 | SSMAEIAASEEGGGSLSTKTSSIASAMSNAFLQTTGVVNQPFINEITQLVSMFAQAGMNDV |
| Lg MaSp1 | SSVAEIAASEG--GDLGVTTNAIADALTSAFYQTTGVVNRFISEIRSLISMFAQASANDV |
| Lh MaSp1 | SSVAEIAASEG--GDLGVTTNAIADALTSAFYQTTGVVNSRFISEIRSLIGMFAQASANDV |
| Nc MaSp1 | SSMAEIAAVEQGGLSVDAKTNAIADSLNSAFYQTTGAANPQFVNEIRSLINMFAQSSANEV |
| At MaSp2 | SSMAEIAVAEQGGLSLEAKTNAIASALSAAFLETTGYVNQQFVNEIKTLIFMIAQASSNEI |
| Lg MaSp2 | SSVAEIAVADG--QNVGGATNAISNALRSAFYQTTGVVNQFISEISNLINMFAQVSANEV |
| Lh MaSp2 | SSVAEIAVADG--QNVGAATNAISDALRSAFYQTTGVVNQFITGISSLIGMFAQVSGNEV |
| Nim MaSp2 | SSMAEIAAVEQGGQSMDVKTNAIANALDSAFYMTTGSTNQQFVNEMRSLINMLSAAAVNEV |
| Nc MaSp2 | SSMAEIAAVEQGGMSMAVKTNAIVDGLNSAFYMTTGAANPQFVNEMRSLISMISAASANEV |
| Ab CySp1 | SSLTDLLIAESAESNYSNQLSELTGILSDCFIQTTGSDNPAFVSRIQSLISVLSQNADTNI |
| Ncl CySp1 | SSLADLLISESSGSSYQTQISALTNILSDCFVTTTGSNNPAFVSRVQTLIGVLSQSSSNAI |
| Lh TuSp1 | SSLAELLVTESAEEDIDNQVALSTILSQCFVETTGSPNPAFVASVKSLLGVLSQSASNYE |
| Nc flag | SSIAELVIAESSGGDVQRKTNVISNALRNALMSTTGSPNEEFVHEVQDLIQMLSQEQINEV |
| Nlm flag | SSIAELVIAESSGGDVQRKTNVISNALRNALMSTTGSPNEEFVHEVQDLIQMLSQEQINEV |

Fig 1

| | | | | | |
|---|---|---|---|---|---|
| CThyb_Esp | SRLSSPEASS | RVSSAVSNLV | SSG-PTNSAA | LSSTISNVVS | QIGASNPGLS |
| CTnat_Eau | SRLSSPSAVS | RVSSAVSSLV | SNG-QVNMAA | LPNIISNISS | SVSASAPGAS |
| AF350266_At1 | SRLSSPGAAS | RVSSAVTSLV | SSGGPTNSAA | LSNTISNVVS | QISSSNPGLS |
| AY666062_Cm1 | SHLSSPEASS | RVSSAVSNLV | SSG-STNSAA | LPNTISNVVS | QISSSNPGLS |
| AF350273_Lg1 | SALAAPATSA | RISSHASTLL | SNG-PTNPAS | ISNVISNAVS | QISSSNPGAS |
| AY953074_Lh1 | SALSAPATSA | RISSHASALL | SSG-PTNPAS | ISNVISNAVS | QISSSNPGAS |
| AY666068_Mh1 | SHLSSPEASS | RVSSAVSNLV | SGG-STNSAA | LPNTISNVVS | QISSSNPGLS |
| U20329_Nc1 | SRLSSPQASS | RVSSAVSNLV | ASG-PTNSAA | LSSTISNVVS | QIGASNPGLS |
| AY666076_Np1 | SRLSSPEASS | RVSSAVSNLV | SSG-PTNSAA | LSNTISNVVS | QISSSNPGLS |
| AF350277_Nm1 | SRLSSPQASS | RVSSAVSNLV | ASG-PTNSAA | LSSTISNAVS | QIGASNPGLS |
| AF350279_Ns1 | SRLSSPEASS | RVSSAVSNLV | SSG-PTNSAA | LSSTISNVVS | QIGASNPGLS |
| AY666057_Ov1 | SRLSSPEASS | RVSSAVSNLV | SSG-PTNSAA | LSNTISNVVS | QISSSNPGLS |
| AY666064_Ps1 | SRLSSPEASS | RVSSAVSNLV | SSG-PTNSAA | LPNTISNVVS | QISSSNPGLS |
| AF350285_Tk1 | SLLSSPASNA | RISSAVSALA | SGA-ASGPGY | LSSVISNVVS | QVSSNSGGLV |
| AF350286_Tv1 | SRLSSPASNA | RISSAVSALA | SGG-ASSPGY | LSSIISNVVS | QVSSNDGLS |
| ABU20328_Ab2 | SRLSSSAASS | RVSSAVSSLV | SSG-PTTPAA | LSNTISSAVS | QISASNPGLS |
| AY365016_Aam2 | -RLSSPQASS | RVSSAVSTLV | SSG-PTNPAS | LSNAIGSVVS | QVSASNPGLP |
| AF350263_Aau2 | SRLSSPQASS | RVSSAVSTLV | SSG-PTNPAA | LSNAISSVVS | QVSASNPGLS |
| AF350267_At2 | SRLSSPQASS | RVSSAVSTLV | SSG-PTNPAS | LSNAISSVVS | QVSSSNPGLS |
| AF350272_Gm2 | SRLSSPQAGA | RVSSAVSALV | ASG-PTSPAA | VSSAISNVAS | QISASNPGLS |
| AF350275_Lg2 | SALSSPTTHA | RISSHASTLL | SSG-PTNSAA | ISNVISNAVS | QVSASNPGSS |
| AY953075_Lh2 | SALSSPTTHA | RISSHASTLL | SSG-PTNAAA | LSNVISNAVS | QVSASNPGSS |
| AY654293_Nc2 | SRLASPDSGA | RVASAVSNLV | SSG-PTSSAA | LSSVISNAVS | QIGASNPGLS |
| AF350278_Nm2 | SRLASPDSGA | RVASAVSNLV | SSG-PTSSAA | LSSVISNAVS | QIGASNPGLS |
| AF350280_Ns2 | SRLASPDSGA | RVASAVSNLV | SSG-PTSSAA | LSSVIXNAVS | QIGASNPGLS |
| AF350269_DtFb1 | SRLSSPEAAS | RVSSAVSSLV | SNG-QVNVDA | LPSIISNLSS | SISASATTAS |
| AF350270_DtFb2 | SRLSSPQAAS | RVSSAVSSLV | SNG-QVNVAA | LPSIISSLSS | SISASSTAAS |
| U47853_ADF1 | NRLSSAGAAS | RVSSNVAAIA | SAG----AAA | LPNVISNIYS | GVLSS--GVS |
| U47854_ADF2 | SRLSSPSAAA | RVSSAVS-LV | SNGGPTSPAA | LSSSISNVVS | QISASNPGLS |
| U47855_ADF3 | SRLSSPAASS | RVSSAVSSLV | SSG-PTKHAA | LSNTISSVVS | QVSASNPGLS |
| U47856_ADF4 | SVYLRLQPRL | EVSSAVSSLV | SSG-PTNGAA | VSGALNSLVS | QISASNPGLS |
| | | | | | |
| Consensus | SRLSSPQASS | RVSSAVSNLV | SSG-PTNSAA | LSNTISNVVS | QISASNPGLS |

Fig 2

```
CThyb_Esp      GCDVLVQALL EVVSALIHIL GSSSIGQVNY GSAGQATQLV GQSVYQALGE F
CTnat_Eau      GCEVIVQALL EVITALVQIV SSSSVGYINP SAVNQITNVV ANAMAQVMG- -
AF350266_At1   GCDVLVQALL EIVSALVHIL GSANIGQVNS SGVGRSASIV GQSINQAFS- -
AY666062_Cm1   GCDVLVQALL EVVSALIHIL GSSSIGQVNY GSAGQATQIV ---------- -
AF350273_Lg1   SCDVLVQALL ELVTALLTII GSSNVGNVNY DSSGQYAQVV SQSVQNAFV- -
AY953074_Lh1   ACDVLVQALL ELVTALLTII GSSNIGSVNY DSSGQYAQVV TQSVQNVFG- -
AY666068_Mh1   GCDVLVQALL EVVSALIHIL GSSSIGQVDY GSAGQATQIV GQSA------ -
U20329_Nc1     GCDVLIQALL EVVSALIQIL GSSSIGQVNY GSAGQATQIV GQSVYQALG- -
AY666076_Np1   GCDVLVQALL EVVSALIHIL GSSSIGQVNY GSAGQATQIV ---------- -
AF350277_Nm1   GCDVLIQALL EVVSALIHIL GSSSIGQVNY GSAGQATQ-- ---------- -
AF350279_Ns1   GCDVLIQALL EVVSALVHIL GSSSIGQVNY GSAGQATQ-- ---------- -
AY666057_Ov1   GCDVLVQALL EVVSAPIHIL GSSSIGQVNY GSAGQATQIV ---------- -
AY666064_Ps1   GCDVLVQALL EVVSALIHIL GSSSIGQVNY GSAGQATQIV ---------- -
AF350285_Tk1   GCDTLVQALL EAAAALVEVL ASSSGGQVNL NTAGYTSQL- ---------- -
AF350286_Tv1   GCDTVVQALL EVAAALVEVL ASSNIGQVNL NTAGYTSQL- ---------- -
ABU20328_Ab2   GCDVLVQALL EVVSALVHIL GSSSVGQINY GASAQYAQMV ---------- -
AY365016_Aam2  SCDVLVQALL EIVSALVHIL GSSSIGQINY SASSQYARLV GQSIAQALG- -
AF350263_Aau2  GCDVLVQALL ELVSALVHIL GSSSIGQINY AAS------- ---------- -
AF350267_At2   GCDVLVQALL EIVSALVHIL GSSSIGQINY AASSQYAQLV GQSLTQALG- -
AF350272_Gm2   GCDVLVQALL EIVSALVSIL SSASIGQINY GASGQYAAMI ---------- -
AF350275_Lg2   SCDVLVQALL ELITALISIV DSSNIGQVNY GSSGQYAQMV G--------- -
AY953075_Lh2   SCDVLVQALL EIITALISIL DSSSVGQVNY GSSGQYAQIV GQSMQQAMG- -
AY654293_Nc2   GCDVLIQALL EIVSACVTIL SSSSIGQVNY GAASQFAQVV GQSVLSAF-- -
AF350278_Nm2   GCDVLIQALL EIVSACVTIL SSSSIGQVNY GAA------- ---------- -
AF350280_Ns2   GCDVLIXALL EIVSACVTIL SSSSIGQVNY GAA------- ---------- -
AF350269_DtFb1 DCEVLVQVLL EVVSALVQIV CS-------- ---------- ---------- -
AF350270_DtFb2 DCEVLVQVLL EIVSALVQIV SSANVGYINP EASGSLN-AV GSALAAAMG- -
U47853_ADF1    SSEALIQALL EVISALIEVL GSASIGNVSS VGVNSALNAV QNAVGAYAG- -
U47854_ADF2    GCDILVQALL EIISALVHIL GSANIGPVNS SSAGQSASIV GQSVYRALS- -
U47855_ADF3    GCDVLVQALL EVVSALVSIL GSSSIGQINY GASAQYTQMV GQSVAQALA- -
U47856_ADF4    GCDALVQALL ELVSALVAIL SSASIGQVNV SSVSQSTQMI SQALS----- -

Consensus      GCDVLVQALL EVVSALVHIL GSSSIGQVNY GSAGQATQIV GQSVAQALGE F
```

Fig 2 (continued)

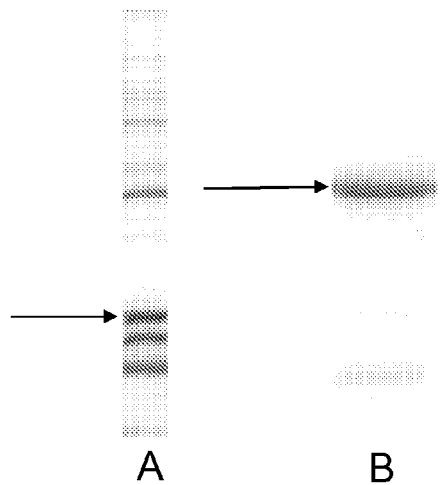
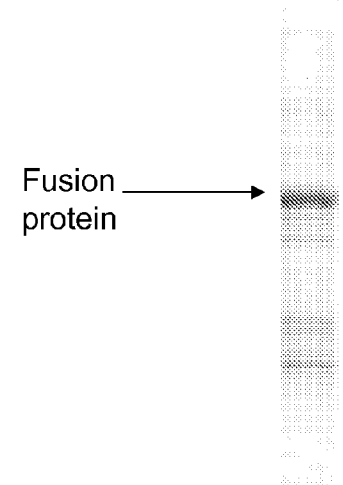
Fig. 6
Fig. 7
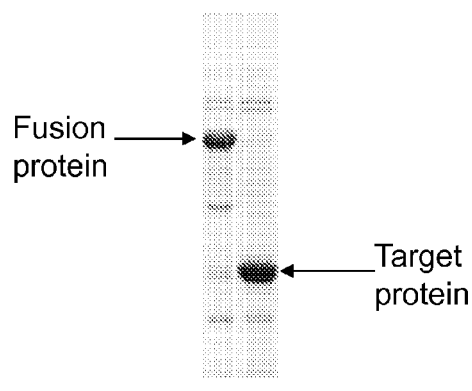
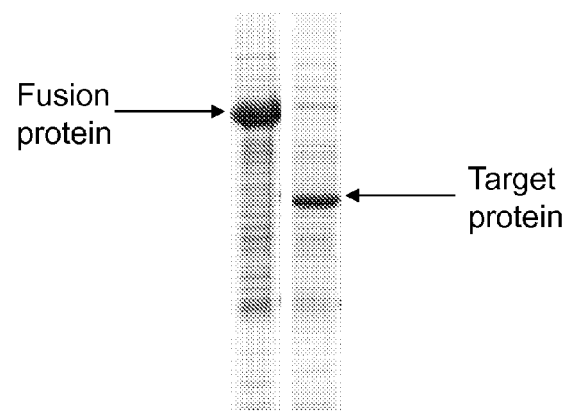
Fig. 8
Fig. 9

US 9,644,012 B2

PRODUCTION OF PROTEINS AND POLYPEPTIDES

TECHNICAL FIELD OF THE INVENTION

The present invention relates to the field of production of proteins and polypeptides, and more specifically to production of spider silk proteins (spidroins) and other, non-spidroin proteins and polypeptides. The present invention provides a method of producing a desired protein, which may be a spidroin protein/polypeptide or a non-spidroin protein/polypeptide. There is also provided novel fusion protein intermediates for production of the desired proteins and polypeptides as well as polynucleic acid molecules encoding these intermediates.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-06-11 0104-0859PUS1 $_{ST}$25.txt" created on Jun. 11, 2015 and is 188,568 bytes in size. The sequence listing contained in this .txt file is part of the specification and is hereby incorporated by reference herein in its entirety.

BACKGROUND TO THE INVENTION

Production of proteins and polypeptides from DNA can be achieved in various hosts, but a common problem is the formation of insoluble protein/polypeptide aggregates. This may severely impede or even prevent production of a functional protein/polypeptide. One solution to this problem is to express the desired protein or polypeptide as a fusion protein with a protein or polypeptide that provides the required solubility. The fusion protein may be cleaved, and the desired protein isolated.

The problem is typically aggravated with low-solubility proteins and polypeptides, e.g. membrane-associated proteins and polypeptides. For instance, lung surfactant protein C (SP-C; Table 6) is a transmembrane protein that is produced by alveolar type II cells and is a constituent of surfactant, that is necessary to prevent alveolar collapse at end expiration. Neonatals often suffer from respiratory distress due to insufficient amounts of surfactant. Today, this condition is treated with surfactant preparations extracted from animal lungs. SP-C-33 is a variant of SP-C, where the residues in the transmembrane helix (normally mainly valines) are exchanged for leucines. SP-C-33 retains the function of native SP-C, including proper insertion in membranes, but is less prone to aggregate and therefore feasible to produce in large quantities for development of a synthetic surfactant preparation. Since SP-C-33 so far has not been possible to produce from DNA, it is today manufactured by chemical synthesis.

Other examples of proteins and polypeptides that pose difficulties when expressed from recombinant DNA are Aβ-peptide, IAPP, PrP, α-synuclein, calcitonin, prolactin, cystatin, ATF and actin; SP-B, α-defensins and β-defensins; class A-H apolipoproteins; LL-37, SP-C, SP-C33Leu, Brichos, GFP, neuroserpin; hormones, including EPO and GH, and growth factors, including IGF-I and IGF-II; avidin and streptavidin; and protease 3C.

SUMMARY OF THE INVENTION

It is an object of the present invention to provide new means and methods for production of proteins and polypeptides, and in particular non-spidroin proteins and polypeptides.

It is also an object of the present invention to provide new means and methods for production of proteins and polypeptides, and in particular non-spidroin proteins and polypeptides, with low solubility in water, e.g. proteins and polypeptides that are prone to aggregate when produced from recombinant DNA, membrane proteins and polypeptides, and amyloid-forming proteins and polypeptides.

It is a further object of the present invention to provide alternative means and methods for production of protein or polypeptide drugs and drug targets.

It is an object of the present invention to provide new means and methods for production of disulphide-containing proteins and polypeptides.

It is also an object of the present invention to provide new means and methods for production of apolipoproteins.

For these and other objects that will be evident from the following specification, the present invention provides according to a first aspect a fusion protein that is useful in a method of producing a desired protein or polypeptide. The fusion protein may be useful as such, or it may be cleaved to obtain the desired protein or polypeptide in isolated form. Fusion proteins according to the invention are comprising (i) at least one solubility-enhancing moiety which is derived from the N-terminal (NT) fragment of a spider silk protein; and (ii) at least one moiety which is a desired protein or polypeptide; wherein each solubility-enhancing moiety is linked directly or indirectly to the desired protein or polypeptide moiety.

In certain embodiments of the fusion protein, each solubility-enhancing moiety has at least 80% identity to SEQ ID NO 6 or at least 50% identity to SEQ ID NO 8. In specific embodiments of the fusion protein, each solubility-enhancing moiety contains from 100 to 160 amino acid residues.

In one embodiment, the fusion protein is subject to the proviso that when the fusion protein comprises a single solubility-enhancing moiety which is derived from the N-terminal (NT) fragment of a spider silk protein, then the desired protein or polypeptide is a non-spidroin protein or polypeptide.

In preferred embodiments, the desired protein or polypeptide is a non-spidroin protein or polypeptide. In some embodiments, the desired protein or polypeptide has less than 30% identity to any of SEQ ID NO: 6-10.

In certain embodiments, the fusion protein is comprising at least two solubility-enhancing moieties, each being derived from the N-terminal (NT) fragment of a spider silk protein. In specific embodiments, the fusion protein is comprising at least two consecutive solubility-enhancing moieties, each being derived from the N-terminal (NT) fragment of a spider silk protein.

In some embodiments of the fusion protein, at least one solubility-enhancing moiety is linked directly or indirectly to the amino-terminal or the carboxy-terminal end of at least one desired protein or polypeptide moiety. In specific embodiments, at least one solubility-enhancing moiety constitutes the amino-terminal and/or the carboxy-terminal end of the fusion protein.

In one embodiment, the fusion protein is further comprising (iii) at least one cleavage site arranged between at least one desired protein or polypeptide moiety and at least one solubility-enhancing moiety.

In certain embodiments of the fusion protein, the desired protein or polypeptide is derived from sponges, comb jellies, jellyfishes, corals, anemones, flatworms, rotifers, roundworms, ribbon worms, clams, snails, octopuses, segmented worms, crustaceans, insects, bryozoans, brachiopods, phoronids, sea stars, sea urchins, tunicates, lancelets, vertebrates, including human, plants, fungi, yeast, bacteria, archaebacteria or viruses or is an artificial protein or polypeptide. In specific embodiments, the desired protein or polypeptide is derived from molluscs, insects, vertebrates, including human, plants, fungi, yeast, bacteria, archaebacteria or viruses or is an artificial protein or polypeptide. In further specific embodiments, the desired protein or polypeptide is derived from vertebrates, including human, plants, fungi, yeast, bacteria, archaebacteria or viruses or is an artificial protein or polypeptide.

In some embodiments of the fusion protein, the desired protein or polypeptide is selected from the group consisting of amyloid-forming proteins and polypeptides, disulphide-containing proteins and polypeptides, apolipoproteins, membrane proteins and polypeptides, protein and polypeptide drugs and drug targets, aggregation-prone proteins and polypeptides, and proteases. In specific embodiments of the fusion protein, the desired protein or polypeptide is selected from the group consisting of Aβ-peptide, IAPP, PrP, α-synuclein, calcitonin, prolactin, cystatin, ATF and actin; SP-B, α-defensins and β-defensins; class A-H apolipoproteins; LL-37, SP-C, SP-C33, SP-C33Leu, Brichos, GFP, neuroserpin; hormones, including EPO and GH, and growth factors, including IGF-I and IGF-II; avidin and streptavidin; and protease 3C.

Preferred embodiments of the fusion protein are selected from the group consisting of SEQ ID NOS 26, 28, 30, 34, 37, 39, 42 and 47 and proteins having at least 80%, preferably at least 90%, more preferably at least 95% identity, to any of these proteins.

According to a specific aspect, the desired protein or polypeptide is a spidroin protein or polypeptide. A preferred desired spidroin protein is comprising: a repetitive fragment of from 70 to 300 amino acid residues derived from the repetitive fragment of a spider silk protein; and a C-terminal fragment of from 70 to 120 amino acid residues, which fragment is derived from the C-terminal fragment of a spider silk protein, and optionally an N-terminal fragment of from 100 to 160 amino acid residues derived from the N-terminal fragment of a spider silk protein.

A further preferred desired spidroin protein is selected from the group of proteins defined by the formulas REP-CT and NT-REP-CT, wherein NT is a protein fragment having from 100 to 160 amino acid residues, which fragment is a N-terminal fragment derived from a spider silk protein; REP is a protein fragment having from 70 to 300 amino acid residues, wherein said fragment is selected from the group of $L(AG)_nL$, $L(AG)_nAL$, $L(GA)_nL$, $L(GA)_nGL$, wherein n is an integer from 2 to 10; each individual A segment is an amino acid sequence of from 8 to 18 amino acid residues, wherein from 0 to 3 of the amino acid residues are not Ala, and the remaining amino acid residues are Ala; each individual G segment is an amino acid sequence of from 12 to 30 amino acid residues, wherein at least 40% of the amino acid residues are Gly; and each individual L segment is a linker amino acid sequence of from 0 to 20 amino acid residues; and CT is a protein fragment having from 70 to 120 amino acid residues, which fragment is a C-terminal fragment derived from a spider silk protein.

According to another aspect, the present invention provides isolated polynucleic acids encoding the fusion proteins according to the invention. Preferred embodiments of the isolated polynucleic acids are selected from the group consisting of nucleic acids encoding a fusion protein selected from the group consisting of SEQ ID NOS 26, 28, 30, 34, 37, 39, 42 and 47 and proteins having at least 80%, preferably at least 90%, more preferably at least 95% identity, to any of these proteins; and the group of nucleic acids consisting of SEQ ID NOS 27, 29, 31, 38, 40, 43 and 48.

According to one aspect, the present invention provides a novel use of at least one moiety which is derived from the N-terminal (NT) fragment of a spider silk protein as a solubility enhancing moiety in a fusion protein for production of a desired protein or polypeptide. In a preferred embodiment, the desired protein or polypeptide is a non-spidroin protein or polypeptide. In one embodiment, the fusion protein is subject to the proviso that when the fusion protein comprises a single solubility-enhancing moiety which is derived from the N-terminal (NT) fragment of a spider silk protein, then the desired protein or polypeptide is a non-spidroin protein or polypeptide. In a specific embodiment, the desired protein or polypeptide is a spidroin protein or polypeptide.

According to another aspect, the present invention provides a method of producing a fusion protein, comprising the following steps: a) expressing in a suitable host a fusion protein according to the invention; and b) obtaining a mixture containing the fusion protein, and optionally isolating the fusion protein.

According to a related aspect, the present invention provides a method of producing a desired protein or polypeptide, comprising the following steps: a) expressing in a suitable host a fusion protein according to the invention; and b) obtaining a mixture containing the fusion protein or polypeptide, and optionally isolating the fusion protein or polypeptide. In certain embodiments, this method is further comprising the following steps: c) cleaving the fusion protein to provide the desired protein or polypeptide; and d) isolating the desired protein or polypeptide; wherein said fusion protein is comprising: (iii) at least one cleavage site arranged between at least one desired protein or polypeptide moiety and at least one solubility-enhancing moiety.

In certain embodiments of these methods, step b) further involves purification of the fusion protein on an affinity medium with an immobilized NT moiety and/or on an anion exchange medium. In specific embodiments, the purification of the fusion protein on an affinity medium is carried out with association to an affinity medium with an immobilized NT moiety at a pH of 6.3 or lower, followed by dissociation from the affinity medium with a desired dissociation medium. In further specific embodiments, the dissociation medium has a pH of 6.4 or higher, a pH of 4.1 or lower and/or has a high ionic strength. In some embodiments, purification of the fusion protein on an anion exchange medium is carried out with association to the anion exchange medium at a pH of 6.4 or higher, followed by dissociation from the anion exchange medium with a dissociation medium having a high ionic strength. In some embodiments of these methods, the purification of the fusion protein in step b) occurs in a column, on magnetic beads with functionalized surfaces, or on filters with functionalized surfaces.

LIST OF APPENDED SEQUENCES

| SEQ ID NO | |
|---|---|
| 1 | 4Rep |
| 2 | 4RepCT |
| 3 | NT4Rep |
| 4 | NT5Rep |
| 5 | NT4RepCTHis |
| 6 | NT |
| 7 | CT |
| 8 | consensus NT sequence |
| 9 | consensus CT sequence |
| 10 | repetitive sequence from *Euprosthenops australis* MaSp1 |
| 11 | consensus G segment sequence 1 |
| 12 | consensus G segment sequence 2 |
| 13 | consensus G segment sequence 3 |
| 14 | NT4Rep (DNA) |
| 15 | NT4RepCT (DNA) |
| 16 | NT5Rep (DNA) |
| 17 | NT4RepCTHis 2 |
| 18 | NT4RepCTHis 2 (DNA) |
| 19 | ZbasicNT4RepCT |
| 20 | NT4RepCT |
| 21 | HisTrxHisThrNT4RepCT |
| 22 | NT4RepCT 2 |
| 23 | HisNTNT4RepCT |
| 24 | HisNTNT4RepCT (DNA) |
| 25 | NT8RepCT |
| 26 | HisNTMetSP-C33Leu |
| 27 | HisNTMetSP-C33Leu (DNA) |
| 28 | HisNTNTMetSP-C33Leu |
| 29 | HisNTNTMetSP-C33Leu (DNA) |
| 30 | HisNTNTMetLL37 |
| 31 | HisNTNTMetLL37 (DNA) |
| 32 | NTHis |
| 33 | HisNTNT8RepCT |
| 34 | HisNTNTBrichos |
| 35 | HisTrxHisSP-C33Leu |
| 36 | HisTrxHisSP-C33Leu (DNA) |
| 37 | HisTrxNtSP-C33Leu |
| 38 | HisTrxNtSP-C33Leu (DNA) |
| 39 | 2HisNtNtQGBrichos |
| 40 | 2HisNtNtQGBrichos (DNA) |
| 41 | Brichos |
| 42 | 2HisNtNtQGGFP |
| 43 | 2HisNtNtQGGFP (DNA) |
| 44 | GFP (Green Fluorescent Protein) |
| 45 | ZbGFP |
| 46 | HisABPGFP |
| 47 | 2HisNtNtQGNS |
| 48 | 2HisNtNtQGNS (DNA) |
| 49 | NS (Neuroserpin) |

BRIEF DESCRIPTION OF THE DRAWINGS

FIG. 1 (SEQ ID NOS: 50-63) shows a sequence alignment of spidroin N-terminal domains.

FIG. 2 (SEQ ID NOS: 68-98) shows a sequence alignment of spidroin C-terminal domains.

FIG. 6 shows electrophoresis gels of SP-C33Leu fusion proteins.

FIG. 7 shows an electrophoresis gel of a Brichos fusion protein.

FIG. 8 shows an electrophoresis gel of a GFP fusion protein and GFP obtained from the fusion protein.

FIG. 9 shows an electrophoresis gel of a neuroserpin fusion protein and neuroserpin obtained from the fusion protein.

DETAILED DESCRIPTION OF THE INVENTION

Figure 3:
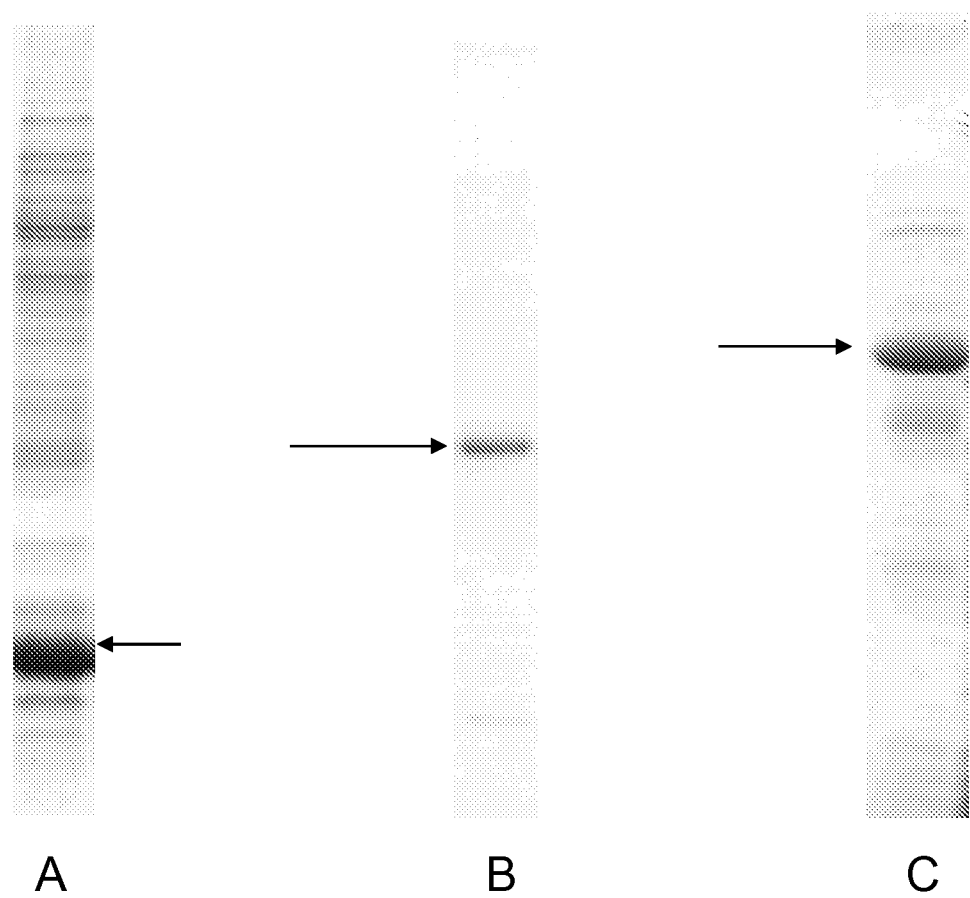
FIG. 3 shows electrophoresis gels of fusion proteins.

The present invention is concerned with production proteins and polypeptides, and in particular non-spidroin proteins and polypeptides. Depending on the purpose with this production, the end product may vary. It may for instance be desirable to obtain the protein or polypeptide inserted in a lipid membrane, in solution or associated with other biomolecules. It shall also be realized that it may also be highly desirable to obtain the desired protein or polypeptide as part of a fusion protein, which may provide a suitable handle for purification and detection and/or provide desirable properties, e.g. stability and solubility.

The present invention is generally based on the insight of the usefulness of the N-terminal (NT) fragment of a spider silk protein as a solubility-enhancing moiety in a fusion protein that is produced from recombinant DNA. Thus, the present invention provides according to a first aspect a fusion protein comprising (i) at least one solubility-enhancing moiety which is derived from the NT fragment of a spider silk protein; and (ii) at least one moiety which is a desired protein or polypeptide. In a preferred embodiment, the fusion proteins consists of (i) at least one solubility-enhancing moiety which is derived from the NT fragment of a spider silk protein; and (ii) at least one moiety which is a desired protein or polypeptide, optionally including other preferred features disclosed herein, e.g. a linker peptide and/or a cleavage site between the solubility-enhancing moiety and the desired protein or polypeptide. In experiments, surprisingly high yields of different fusion proteins has been achieved in *E. coli*. The fusion protein may be useful as such in isolated form, e.g. for studies of otherwise aggregated or poorly soluble proteins in soluble form, or in crystallization associated with X-ray crystallography. The fusion protein may also be cleaved to release the desired protein.

The term "fusion protein" implies here a protein that is made by expression from a recombinant nucleic acid, i.e. DNA or RNA that is created artificially by combining two or more nucleic acid sequences that would not normally occur together (genetic engineering). The fusion proteins according to the invention are recombinant proteins, and they are therefore not identical to naturally occurring proteins. In particular, wildtype spidroins are not fusion proteins according to the invention, because they are not expressed from a recombinant nucleic acid as set out above. The combined nucleic acid sequences encode different proteins, partial proteins or polypeptides with certain functional properties. The resulting fusion protein, or recombinant fusion protein, is a single protein with functional properties derived from each of the original proteins, partial proteins or polypeptides.

In certain embodiments, the fusion protein according to the invention and the corresponding genes are chimeric, i.e. the protein/gene fragments are derived from at least two different species. The solubility-enhancing moiety is derived from the N-terminal fragment of a spider silk protein. According to this aspect, it is preferred that, the desired protein or polypeptide is a non-spidroin protein. This implies that the desired protein or polypeptide is not derived from the C-terminal, repetitive or N-terminal fragment of a spider silk protein.

The fusion protein according to the invention may also contain one or more linker peptides. The linker peptide(s) may be arranged between the solubility-enhancing moiety and the desired protein or polypeptide moiety, or may be arranged at either end of the solubility-enhancing moiety and the desired protein or polypeptide moiety. If the fusion protein contains two or more solubility-enhancing moieties, the linker peptide(s) may also be arranged in between two solubility-enhancing moieties. The linker(s) may provide a spacer between the functional units of the fusion protein, but may also constitute a handle for identification and purification of the fusion protein, e.g. a His and/or a Trx tag. If the fusion protein contains two or more linker peptides for identification and purification of the fusion protein, it is preferred that they are separated by a spacer sequence, e.g. $His_6$-spacer-$His_6$-. The linker may also constitute a signal peptide, such as a signal recognition particle, which directs the fusion protein to the membrane and/or causes secretion of the fusion protein from the host cell into the surrounding medium. The fusion protein may also include a cleavage site in its amino acid sequence, which allows for cleavage and removal of the linker(s) and/or the solubility-enhancing moiety or moieties. Various cleavage sites are known to the person skilled in the art, e.g. cleavage sites for chemical agents, such as CNBr after Met residues and hydroxylamine between Asn-Gly residues, cleavage sites for proteases, such as thrombin or protease 3C. and self-splicing sequences, such as intein self-splicing sequences.

Each solubility-enhancing moiety is linked directly or indirectly to the desired protein or polypeptide moiety. A direct linkage implies a direct covalent binding between the two moieties without intervening sequences, such as linkers. An indirect linkage also implies that the two moieties are linked by covalent bonds, but that there are intervening sequences, such as linkers and/or one or more further solubility-enhancing moieties.

The at least one solubility-enhancing moiety may be arranged at either end of the desired protein or polypeptide, i.e. C-terminally arranged or N-terminally arranged. It is preferred that the least one solubility-enhancing moiety is arranged at the N-terminal end of the desired protein or polypeptide. If the fusion protein contains one or more linker peptide(s) for identification and purification of the fusion protein, e.g. a His or Trx tag(s), it is preferred that it is arranged at the N-terminal end of the fusion protein. The at least one solubility-enhancing moiety may also be integrated within the desired protein or polypeptide, for instance between domains or parts of a desired protein. In a preferred embodiment, at least one solubility-enhancing moiety constitutes the N-terminal and/or the C-terminal end of the fusion protein, i.e. no linker peptide or other sequence is present terminal of the solubility-enhancing moiety. A typical fusion protein according to the invention may contain 1-6, such as 1-4, such as 1-2 solubility-enhancing moieties.

In a preferred embodiment, the fusion protein is comprising at least two solubility-enhancing moieties, each being derived from the N-terminal (NT) fragment of a spider silk protein. The solubility-enhancing moieties, preferably two solubility-enhancing moieties, may be consecutively arranged at either end of the desired protein or polypeptide, i.e. C-terminally arranged or N-terminally arranged. Consecutively arranged solubility-enhancing moieties may also be integrated within the desired protein or polypeptide, for instance between domains or parts of a desired protein. The solubility-enhancing moieties may also be non-consecutively arranged, either at each end of the desired protein or polypeptide, i.e. C-terminally and N-terminally arranged, or at one end of the desired protein or polypeptide and integrated within the desired protein or polypeptide. A typical preferred fusion protein according to the invention may contain 2-6, such as 2-4 solubility-enhancing moieties.

In a preferred embodiment, the fusion protein according has at least one cleavage site arranged between at least one desired protein or polypeptide moiety and at least one solubility-enhancing moiety. This allows for cleavage of the fusion protein and purification of the desired protein. It is however noted that it may be desirable to obtain the desired protein or polypeptide as part of a fusion protein, which may provide a suitable handle for purification and detection and/or provide desirable properties, e.g. stability and solubility. In this case, the cleavage site may be omitted, or the cleavage site may be included but the cleavage step omitted.

A preferred fusion protein has the form of an N-terminally arranged solubility-enhancing moiety, coupled by a linker peptide of 1-30 amino acid residues, such as 1-10 amino acid residues, to a C-terminally arranged desired protein or polypeptide. The linker peptide may contain a cleavage site. Optionally, the fusion protein has an N-terminal or C-terminal linker peptide, which may contain a purification tag, such as a His tag, and a cleavage site.

Another preferred fusion protein has the form of an N-terminally arranged solubility-enhancing moiety coupled directly to a C-terminally arranged desired protein or polypeptide. Optionally, the fusion protein has an N-terminal or C-terminal linker peptide, which may contain a purification tag, such as a His tag, and a cleavage site.

One preferred fusion protein has the form of a two consecutive N-terminally arranged solubility-enhancing moieties, coupled by a linker peptide of 1-30 amino acid residues, such as 1-10 amino acid residues, to a C-terminally arranged desired protein or polypeptide. The linker peptide may contain a cleavage site. Optionally, the fusion protein has an N-terminal or C-terminal linker peptide, which may contain a purification tag, such as a His tag, and a cleavage site.

Another preferred fusion protein has the form of two consecutive N-terminally arranged solubility-enhancing moieties coupled directly to a C-terminally arranged desired protein or polypeptide. Optionally, the fusion protein has an N-terminal or C-terminal linker peptide, which may contain a purification tag, such as a His tag, and a cleavage site.

The solubility-enhancing moiety is derived from the NT fragment of a spider silk protein, or spidroin. Although the examples by necessity relate to specific NT fragments, in this case proteins derived from major spidroin 1 (MaSp1) from *Euprosthenops australis*, it is considered that the method disclosed herein is applicable to any similar protein moiety. The terms "spidroins" and "spider silk proteins" are used interchangeably throughout the description and encompass all known spider silk proteins, including major ampullate spider silk proteins which typically are abbreviated "MaSp", or "ADF" in the case of *Araneus diadematus*. These major ampullate spider silk proteins are generally of two types, 1 and 2. These terms furthermore include the new NT protein fragments according to the invention, as defined in the appended claims and itemized embodiments, and other non-natural proteins with a high degree of identity and/or similarity to the known spider silk NT protein fragments.

The solubility-enhancing moiety has a high degree of similarity to the N-terminal (NT) amino acid sequence of spider silk proteins. As shown in FIG. 1, this amino acid sequence is well conserved among various species and spider silk proteins, including MaSp1 and MaSp2. In FIG. 1, the following spidroin NT fragments are aligned, denoted with GenBank accession entries where applicable:

TABLE 1

Spidroin NT fragments

| Code | Species and spidroin protein | GenBank acc. no. |
|---|---|---|
| Ea MaSp1 | *Euprosthenops australis* MaSp 1 | AM259067 |
| Lg MaSp1 | *Latrodectus geometricus* MaSp 1 | ABY67420 |
| Lh MaSp1 | *Latrodectus hesperus* MaSp 1 | ABY67414 |
| Nc MaSp1 | *Nephila clavipes* MaSp 1 | ACF19411 |
| At MaSp2 | *Argiope trifasciata* MaSp 2 | AAZ15371 |
| Lg MaSp2 | *Latrodectus geometricus* MaSp 2 | ABY67417 |
| Lh MaSp2 | *Latrodectus hesperus* MaSp 2 | ABR68855 |
| Nim MaSp2 | *Nephila inaurata madagascariensis* MaSp 2 | AAZ15322 |
| Nc MaSp2 | *Nephila clavipes* MaSp 2 | ACF19413 |
| Ab CySp1 | *Argiope bruennichi* cylindriform spidroin 1 | BAE86855 |
| Ncl CySp1 | *Nephila clavata* cylindriform spidroin 1 | BAE54451 |
| Lh TuSp1 | *Latrodectus hesperus* tubuliform spidroin | ABD24296 |
| Nc Flag | *Nephila clavipes* flagelliform silk protein | AF027972 |
| Nim Flag | *Nephila inaurata madagascariensis* flagelliform silk protein | AF218623 (translated) |

Only the part corresponding to the N-terminal domain is shown for each sequence, omitting the signal peptide. Nc flag and Nlm flag are translated and edited according to Rising A. et al. Biomacromolecules 7, 3120-3124 (2006)).

It is not critical which specific solubility-enhancing moiety is present in fusion proteins according to the invention, as long as the solubility-enhancing moiety is not entirely missing. Thus, the solubility-enhancing moiety according to the invention can be selected from any of the amino acid sequences shown in FIG. 1 or sequences with a high degree of similarity. A wide variety of solubility-enhancing sequences can be used in the fusion protein according to the invention. Based on the homologous sequences of FIG. 1, the following sequence constitutes a consensus solubility-enhancing amino acid sequence:

```
                                      (SEQ ID NO 8)
QANTPWSSPNLADAFINSF(M/L)SA(A/I)SSSGAFSADQLDDMSTI

G(D/N/Q)TLMSAMD(N/S/K)MGRSG(K/R)STKSKLQALNMAFASS

MAEIAAAESGG(G/Q)SVGVKTNAISDALSSAFYQTTGSVNPQFV (N/S)EIRSLI(G/N)M(F/L)(A/S)QASANEV.
```

The sequence of the solubility-enhancing moiety according to the invention has at least 50% identity, preferably at least 60% identity, to the consensus amino acid sequence SEQ ID NO 8, which is based on the amino acid sequences of FIG. 1. In a preferred embodiment, the sequence of the solubility-enhancing moiety according to the invention has at least 65% identity, preferably at least 70% identity, to the consensus amino acid sequence SEQ ID NO 8. In preferred embodiments, the solubility-enhancing moiety according to the invention has furthermore 70%, preferably 80%, similarity to the consensus amino acid sequence SEQ ID NO 8.

A representative solubility-enhancing moiety according to the invention is the *Euprosthenops australis* sequence SEQ ID NO 6. According to a preferred embodiment of the invention, the solubility-enhancing moiety has at least 80% identity to SEQ ID NO 6 or any individual amino acid sequence in FIG. 1. In preferred embodiments of the invention, the solubility-enhancing moiety has at least 90%, such as at least 95% identity, to SEQ ID NO 6 or any individual amino acid sequence in FIG. 1. In preferred embodiments of the invention, the solubility-enhancing moiety is identical to SEQ ID NO 6 or any individual amino acid sequence in FIG. 1, in particular to Ea MaSp1.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The amino acid residues at each position are compared, and the percentage of positions in the query sequence that have identical correspondences in the target sequence is reported as % identity.

The term "% similarity", as used throughout the specification and the appended claims, is calculated as described for "% identity", with the exception that the hydrophobic residues Ala, Val, Phe, Pro, Leu, Ile, Trp, Met and Cys are similar; the basic residues Lys, Arg and His are similar; the acidic residues Glu and Asp are similar; and the hydrophilic, uncharged residues Gln, Asn, Ser, Thr and Tyr are similar. The remaining natural amino acid Gly is not similar to any other amino acid in this context.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

The solubility-enhancing moiety contains from 100 to 160 amino acid residues. It is preferred that the solubility-enhancing moiety contains at least 100, or more than 110, preferably more than 120, amino acid residues. It is also preferred that the solubility-enhancing moiety contains at most 160, or less than 140 amino acid residues. A typical solubility-enhancing moiety contains approximately 130-140 amino acid residues.

In certain embodiments of the present invention, the desired protein or polypeptide is a spidroin protein or polypeptide. The sequence of a desired spidroin protein or polypeptide according to the invention has at least 50% identity, such as at least 60% identity, preferably at least 70% identity, to any of the spidroin amino acid sequences disclosed herein. In a preferred embodiment, the sequence of a desired spidroin protein or polypeptide according to the invention has at least 80% identity, preferably at least 90% identity, to any of the spidroin amino acid sequences disclosed herein.

In a preferred embodiment, the desired spidroin protein is comprising a repetitive fragment of from 70 to 300 amino acid residues derived from the repetitive fragment of a spider silk protein; and a C-terminal fragment of from 70 to 120 amino acid residues, which fragment is derived from the C-terminal fragment of a spider silk protein. Optionally, the desired spidroin protein is comprising an N-terminal fragment of from 100 to 160 amino acid residues derived from the N-terminal fragment of a spider silk protein. The desired spidroin protein consists of from 170 to 600 amino acid residues, preferably from 280 to 600 amino acid residues, such as from 300 to 400 amino acid residues, more preferably from 340 to 380 amino acid residues. The small size is advantageous because longer spider silk proteins tend to form amorphous aggregates, which require use of harsh solvents for solubilisation and polymerisation. The protein fragments are covalently coupled, typically via a peptide bond.

In specific preferred embodiments, the desired spidroin protein is selected from the group of proteins defined by the formulas NT$_2$-REP-CT (or NT-NT-REP-CT), NT-REP-CT and REP-CT.

The NT fragment has a high degree of similarity to the N-terminal amino acid sequence of spider silk proteins. As shown in FIG. 1, this amino acid sequence is well conserved among various species and spider silk proteins, including MaSp1 and MaSp2, see also Table 1:

It is not critical which specific NT fragment is present in desired spidroin proteins according to the invention. Thus, the NT fragment according to the invention can be selected from any of the amino acid sequences shown in FIG. 1 or sequences with a high degree of similarity. A wide variety of N-terminal sequences can be used in the desired spidroin protein according to the invention. Based on the homologous sequences of FIG. 1, the following sequence constitutes a consensus NT amino acid sequence:

```
                                              (SEQ ID NO: 8)
QANTPWSSPNLADAFINSF(M/L)SA(A/I)SSSGAFSADQLDDMSTI

G(D/N/Q)TLMSAMD(N/S/K)MGRSG(K/R)STKSKLQALNMAFASS

MAEIAAAESGG(G/Q)SVGVKTNAISDALSSAFYQTTGSVNPQFV (N/S)EIRSLI(G/N)M(F/L)(A/S)QASANEV.
```

The sequence of the NT fragment according to the invention has at least 50% identity, preferably at least 60% identity, to the consensus amino acid sequence SEQ ID NO: 8, which is based on the amino acid sequences of FIG. 1. In a preferred embodiment, the sequence of the NT fragment according to the invention has at least 65% identity, preferably at least 70% identity, to the consensus amino acid sequence SEQ ID NO: 8. In preferred embodiments, the NT fragment according to the invention has furthermore 70%, preferably 80%, similarity to the consensus amino acid sequence SEQ ID NO: 8.

A representative NT fragment according to the invention is the *Euprosthenops australis* sequence SEQ ID NO: 6. According to a preferred embodiment of the invention, the NT fragment has at least 80% identity to SEQ ID NO: 6 or any individual amino acid sequence in FIG. 1. In preferred embodiments of the invention, the NT fragment has at least 90%, such as at least 95% identity, to SEQ ID NO: 6 or any individual amino acid sequence in FIG. 1. In preferred embodiments of the invention, the NT fragment is identical to SEQ ID NO: 6 or any individual amino acid sequence in FIG. 1, in particular to Ea MaSp1.

The NT fragment contains from 100 to 160 amino acid residues. It is preferred that the NT fragment contains at least 100, or more than 110, preferably more than 120, amino acid residues. It is also preferred that the NT fragment contains at most 160, or less than 140 amino acid residues. A typical NT fragment contains approximately 130-140 amino acid residues.

The REP fragment has a repetitive character, alternating between alanine-rich stretches and glycine-rich stretches. The REP fragment generally contains more than 70, such as more than 140, and less than 300, preferably less than 240, such as less than 200, amino acid residues, and can itself be divided into several L (linker) segments, A (alanine-rich) segments and G (glycine-rich) segments, as will be explained in more detail below. Typically, said linker segments, which are optional, are located at the REP fragment terminals, while the remaining segments are in turn alanine-rich and glycine-rich. Thus, the REP fragment can generally have either of the following structures, wherein n is an integer:

L(AG)$_n$L, such as LA$_1$G$_1$A$_2$G$_2$A$_3$G$_3$A$_4$G$_4$A$_5$G$_5$L;
L(AG)$_n$AL, such as LA$_1$G$_1$A$_2$G$_2$A$_3$G$_3$A$_4$G$_4$A$_5$G$_5$A$_6$L;
L(GA)$_n$L, such as LG$_1$A$_1$G$_2$A$_2$G$_3$A$_3$G$_4$A$_4$G$_5$A$_5$L; or
L(GA)$_n$GL, such as LG$_1$A$_1$G$_2$A$_2$G$_3$A$_3$G$_4$A$_4$G$_5$A$_5$G$_6$L.

It follows that it is not critical whether an alanine-rich or a glycine-rich segment is adjacent to the N-terminal or C-terminal linker segments. It is preferred that n is an integer from 2 to 10, preferably from 2 to 8, also preferably from 4 to 8, more preferred from 4 to 6, i.e. n=4, n=5 or n=6.

In preferred embodiments, the alanine content of the REP fragment according to the invention is above 20%, preferably above 25%, more preferably above 30%, and below 50%, preferably below 40%, more preferably below 35%. This is advantageous, since it is contemplated that a higher alanine content provides a stiffer and/or stronger and/or less extendible fiber.

In certain embodiments, the REP fragment is void of proline residues, i.e. there are no Pro residues in the REP fragment.

Now turning to the segments that constitute the REP fragment according to the invention, it shall be emphasized that each segment is individual, i.e. any two A segments, any two G segments or any two L segments of a specific REP fragment may be identical or may not be identical. Thus, it is not a general feature of the invention that each type of segment is identical within a specific REP fragment. Rather, the following disclosure provides the skilled person with guidelines how to design individual segments and gather them into a REP fragment, which is a part of a functional spider silk protein according to the invention.

Each individual A segment is an amino acid sequence having from 8 to 18 amino acid residues. It is preferred that each individual A segment contains from 13 to 15 amino acid residues. It is also possible that a majority, or more than two, of the A segments contain from 13 to 15 amino acid residues, and that a minority, such as one or two, of the A segments contain from 8 to 18 amino acid residues, such as 8-12 or 16-18 amino acid residues. A vast majority of these amino acid residues are alanine residues. More specifically, from 0 to 3 of the amino acid residues are not alanine residues, and the remaining amino acid residues are alanine residues. Thus, all amino acid residues in each individual A segment are alanine residues, with no exception or the exception of one, two or three amino acid residues, which can be any amino acid. It is preferred that the alanine-replacing amino acid(s) is (are) natural amino acids, preferably individually selected from the group of serine, glutamic acid, cysteine and glycine, more preferably serine. Of course, it is possible that one or more of the A segments are all-alanine segments, while the remaining A segments contain 1-3 non-alanine residues, such as serine, glutamic acid, cysteine or glycine.

In a preferred embodiment, each A segment contains 13-15 amino acid residues, including 10-15 alanine residues and 0-3 non-alanine residues as described above. In a more preferred embodiment, each A segment contains 13-15 amino acid residues, including 12-15 alanine residues and 0-1 non-alanine residues as described above.

It is preferred that each individual A segment has at least 80%, preferably at least 90%, more preferably 95%, most preferably 100% identity to an amino acid sequence selected from the group of amino acid residues 7-19, 43-56, 71-83, 107-120, 135-147, 171-183, 198-211, 235-248, 266-279, 294-306, 330-342, 357-370, 394-406, 421-434, 458-470, 489-502, 517-529, 553-566, 581-594, 618-630, 648-661, 676-688, 712-725, 740-752, 776-789, 804-816, 840-853, 868-880, 904-917, 932-945, 969-981, 999-1013, 1028-1042 and 1060-1073 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual A segment has at least 80%, preferably at least 90%, more preferably 95%, most preferably 100% identity to an amino acid sequence selected from the group of amino acid residues 143-152, 174-186, 204-218, 233-247 and 265-278 of SEQ ID NO: 3. Each sequence of this group corresponds to a segment of expressed, non-natural spider silk proteins according to the invention, which proteins have capacity to form silk fibers under appropriate conditions. Thus, in certain embodiments according to the invention, each individual A segment is identical to an amino acid sequence selected from the above-mentioned amino acid segments. Without wishing to be bound by any particular theory, it is envisaged that A segments according to the invention form helical structures or beta sheets.

Furthermore, it has been concluded from experimental data that each individual G segment is an amino acid sequence of from 12 to 30 amino acid residues. It is preferred that each individual G segment consists of from 14 to 23 amino acid residues. At least 40% of the amino acid residues of each G segment are glycine residues. Typically the glycine content of each individual G segment is in the range of 40-60%.

It is preferred that each individual G segment has at least 80%, preferably at least 90%, more preferably 95%, most preferably 100% identity to an amino acid sequence selected from the group of amino acid residues 20-42, 57-70, 84-106, 121-134, 148-170, 184-197, 212-234, 249-265, 280-293, 307-329, 343-356, 371-393, 407-420, 435-457, 471-488, 503-516, 530-552, 567-580, 595-617, 631-647, 662-675, 689-711, 726-739, 753-775, 790-803, 817-839, 854-867, 881-903, 918-931, 946-968, 982-998, 1014-1027, 1043-1059 and 1074-1092 of SEQ ID NO: 10. Each sequence of this group corresponds to a segment of the naturally occurring sequence of *Euprosthenops australis* MaSp1 protein, which is deduced from cloning of the corresponding cDNA, see WO 2007/078239. Alternatively, each individual G segment has at least 80%, preferably at least 90%, more preferably 95%, most preferably 100% identity to an amino acid sequence selected from the group of amino acid residues 153-173, 187-203, 219-232, 248-264 and 279-296 of SEQ ID NO: 3. Each sequence of this group corresponds to a segment of expressed, non-natural spider silk proteins according to the invention, which proteins have capacity to form silk fibers under appropriate conditions. Thus, in certain embodiments according to the invention, each individual G segment is identical to an amino acid sequence selected from the above-mentioned amino acid segments.

In certain embodiments, the first two amino acid residues of each G segment according to the invention are not -Gln-Gln-.

There are the three subtypes of the G segment according to the invention. This classification is based upon careful analysis of the *Euprosthenops australis* MaSp1 protein sequence (WO 2007/078239), and the information has been employed and verified in the construction of novel, non-natural spider silk proteins.

The first subtype of the G segment according to the invention is represented by the amino acid one letter consensus sequence GQG(G/S)QGG(Q/Y)GG (L/Q)GQG-GYGQGA GSS (SEQ ID NO: 11). This first, and generally the longest, G segment subtype typically contains 23 amino acid residues, but may contain as little as 17 amino acid residues, and lacks charged residues or contain one charged residue. Thus, it is preferred that this first G segment subtype contains 17-23 amino acid residues, but it is contemplated that it may contain as few as 12 or as many as 30 amino acid residues. Without wishing to be bound by any particular theory, it is envisaged that this subtype forms coil structures or $3_1$-helix structures. Representative G segments of this first subtype are amino acid residues 20-42, 84-106, 148-170, 212-234, 307-329, 371-393, 435-457, 530-552, 595-617, 689-711, 753-775, 817-839, 881-903, 946-968, 1043-1059 and 1074-1092 of SEQ ID NO: 10. In certain embodiments, the first two amino acid residues of each G segment of this first subtype according to the invention are not -Gln-Gln-.

The second subtype of the G segment according to the invention is represented by the amino acid one letter consensus sequence GQGGQGQG(G/R)Y GQG(A/S)G(S/G)S (SEQ ID NO: 12). This second, generally mid-sized, G segment subtype typically contains 17 amino acid residues and lacks charged residues or contain one charged residue. It is preferred that this second G segment subtype contains 14-20 amino acid residues, but it is contemplated that it may contain as few as 12 or as many as 30 amino acid residues. Without wishing to be bound by any particular theory, it is envisaged that this subtype forms coil structures. Representative G segments of this second subtype are amino acid residues 249-265, 471-488, 631-647 and 982-998 of SEQ ID NO: 10; and amino acid residues 187-203 of SEQ ID NO: 3.

The third subtype of the G segment according to the invention is represented by the amino acid one letter consensus sequence G(R/Q)GQG(G/R)YGQG (A/S/V)GGN (SEQ ID NO: 13). This third G segment subtype typically contains 14 amino acid residues, and is generally the shortest of the G segment subtypes according to the invention. It is preferred that this third G segment subtype contains 12-17 amino acid residues, but it is contemplated that it may contain as many as 23 amino acid residues. Without wishing to be bound by any particular theory, it is envisaged that this subtype forms turn structures. Representative G segments of this third subtype are amino acid residues 57-70, 121-134, 184-197, 280-293, 343-356, 407-420, 503-516, 567-580, 662-675, 726-739, 790-803, 854-867, 918-931, 1014-1027 of SEQ ID NO: 10; and amino acid residues 219-232 of SEQ ID NO: 3.

Thus, in preferred embodiments, each individual G segment has at least 80%, preferably 90%, more preferably 95%, identity to an amino acid sequence selected from SEQ ID NO: 11, SEQ ID NO: 12 and SEQ ID NO: 13.

In a preferred embodiment of the alternating sequence of A and G segments of the REP fragment, every second G segment is of the first subtype, while the remaining G segments are of the third subtype, e.g. . . . $A_1G_{short}A_2G_{long}A_3G_{short}A_4G_{long}A_5G_{short}$ . . . . In another preferred embodiment of the REP fragment, one G segment of the second subtype interrupts the G segment regularity via an insertion, e.g. . . . $A_1G_{short}A_2G_{long}A_3G_{mid}A_4G_{short}A_5G_{long}$ . . . .

Each individual L segment represents an optional linker amino acid sequence, which may contain from 0 to 20 amino acid residues, such as from 0 to 10 amino acid residues.

While this segment is optional and not functionally critical for the spider silk protein, its presence still allows for fully functional spider silk proteins, forming spider silk fibers according to the invention. There are also linker amino acid sequences present in the repetitive part (SEQ ID NO: 10) of the deduced amino acid sequence of the MaSp1 protein from *Euprosthenops australis*. In particular, the amino acid sequence of a linker segment may resemble any of the described A or G segments, but usually not sufficiently to meet their criteria as defined herein.

As shown in WO 2007/078239, a linker segment arranged at the C-terminal part of the REP fragment can be represented by the amino acid one letter consensus sequences ASASAAASAA STVANSVS (SEQ ID NO: 64) and ASASAAA (SEQ ID NO: 65), which are rich in alanine. In fact, the second sequence can be considered to be an A segment according to the invention, while the first sequence has a high degree of similarity to A segments according to the invention. Another example of a linker segment according the invention has the one letter amino acid sequence GSAMGQGS (SEQ ID NO: 66), which is rich in glycine and has a high degree of similarity to G segments according to the invention. Another example of a linker segment is SASAG (SEQ ID NO: 67).

Representative L segments are amino acid residues 1-6 and 1093-1110 of SEQ ID NO: 10; and amino acid residues 138-142 of SEQ ID NO: 3, but the skilled person in the art will readily recognize that there are many suitable alternative amino acid sequences for these segments. In one embodiment of the REP fragment according to the invention, one of the L segments contains 0 amino acids, i.e. one of the L segments is void. In another embodiment of the REP fragment according to the invention, both L segments contain 0 amino acids, i.e. both L segments are void. Thus, these embodiments of the REP fragments according to the invention may be schematically represented as follows: $(AG)_nL$, $(AG)_nAL$, $(GA)_nL$, $(GA)_nGL$; $L(AG)_n$, $L(AG)_nA$, $L(GA)_n$, $L(GA)_nG$; and $(AG)_n$, $(AG)_nA$, $(GA)_n$, $(GA)_nG$. Any of these REP fragments are suitable for use with any CT fragment as defined below.

The CT fragment of the desired spidroin protein has a high degree of similarity to the C-terminal amino acid sequence of spider silk proteins. As shown in WO 2007/078239, this amino acid sequence is well conserved among various species and spider silk proteins, including MaSp1 and MaSp2. A consensus sequence of the C-terminal regions of MaSp1 and MaSp2 is provided as SEQ ID NO: 9. In FIG. 2, the following MaSp proteins are aligned, denoted with GenBank accession entries where applicable:

TABLE 2

| Spidroin CT fragments | |
|---|---|
| Species and spidroin protein | Entry |
| *Euprosthenops* sp MaSp1 (Pouchkina-Stantcheva, N N & McQueen-Mason, S J, ibid) | Cthyb_Esp |
| *Euprosthenops australis* MaSp1 | CTnat_Eau |
| *Argiope trifasciata* MaSp1 | AF350266_Atl |
| *Cyrtophora moluccensis* Sp1 | AY666062_Cm1 |
| *Latrodectus geometricus* MaSp1 | AF350273_Lg1 |
| *Latrodectus hesperus* MaSp1 | AY953074_Lh1 |
| *Macrothele holsti* Sp1 | AY666068_Mh1 |
| *Nephila clavipes* MaSp1 | U20329_Nc1 |
| *Nephila pilipes* MaSp1 | AY666076_Np1 |
| *Nephila madagascariensis* MaSp1 | AF350277_Nm1 |
| *Nephila senegalensis* MaSp1 | AF350279_Ns1 |

TABLE 2-continued

| Spidroin CT fragments | |
|---|---|
| Species and spidroin protein | Entry |
| *Octonoba varians* Sp1 | AY666057_Ov1 |
| *Psechrus sinensis* Sp1 | AY666064_Ps1 |
| *Tetragnatha kauaiensis* MaSp1 | AF350285_Tk1 |
| *Tetragnatha versicolor* MaSp1 | AF350286_Tv1 |
| *Araneus bicentenarius* Sp2 | ABU20328_Ab2 |
| *Argiope amoena* MaSp2 | AY365016_Aam2 |
| *Argiope aurantia* MaSp2 | AF350263_Aau2 |
| *Argiope trifasciata* MaSp2 | AF350267_At2 |
| *Gasteracantha mammosa* MaSp2 | AF350272_Gm2 |
| *Latrodectus geometricus* MaSp2 | AF350275_Lg2 |
| *Latrodectus hesperus* MaSp2 | AY953075_Lh2 |
| *Nephila clavipes* MaSp2 | AY654293_Nc2 |
| *Nephila madagascariensis* MaSp2 | AF350278_Nm2 |
| *Nephila senegalensis* MaSp2 | AF350280_Ns2 |
| *Dolomedes tenebrosus* Fb1 | AF350269_DtFb1 |
| *Dolomedes tenebrosus* Fb2 | AF350270_DtFb2 |
| *Araneus diadematus* ADF-1 | U47853_ADF1 |
| *Araneus diadematus* ADF-2 | U47854_ADF2 |
| *Araneus diadematus* ADF-3 | U47855_ADF3 |
| *Araneus diadematus* ADF-4 | U47856_ADF4 |

It is not critical which specific CT fragment, if any, is present in spider silk proteins according to the invention. Thus, the CT fragment according to the invention can be selected from any of the amino acid sequences shown in FIG. 2 and Table 2 or sequences with a high degree of similarity. A wide variety of C-terminal sequences can be used in the spider silk protein according to the invention.

The sequence of the CT fragment according to the invention has at least 50% identity, preferably at least 60%, more preferably at least 65% identity, or even at least 70% identity, to the consensus amino acid sequence SEQ ID NO: 9, which is based on the amino acid sequences of FIG. 2.

A representative CT fragment according to the invention is the *Euprosthenops australis* sequence SEQ ID NO: 7, Thus, according to a preferred aspect of the invention, the CT fragment has at least 80%, preferably at least 90%, such as at least 95%, identity to SEQ ID NO: 7 or any individual amino acid sequence of FIG. 2 and Table 2. In preferred aspects of the invention, the CT fragment is identical to SEQ ID NO: 7 or any individual amino acid sequence of FIG. 2 and Table 2.

The CT fragment typically consists of from 70 to 120 amino acid residues. It is preferred that the CT fragment contains at least 70, or more than 80, preferably more than 90, amino acid residues. It is also preferred that the CT fragment contains at most 120, or less than 110 amino acid residues. A typical CT fragment contains approximately 100 amino acid residues.

According to another aspect, the desired protein or polypeptide according to the invention is a non-spidroin protein or polypeptide when the fusion protein comprises a single solubility-enhancing moiety which is derived from the N-terminal (NT) fragment of a spider silk protein. In a preferred embodiment, the desired protein or polypeptide is a non-spidroin protein or polypeptide. The sequence of a desired non-spidroin protein or polypeptide according to the invention preferably has less than 30% identity, such as less than 20% identity, preferably less than 10% identity, to any of the spidroin amino acid sequences disclosed herein, and specifically to any of SEQ ID NO: 6-10.

In a preferred embodiment, the desired non-spidroin protein or polypeptide is derived from sponges, comb jellies, jellyfishes, corals, anemones, flatworms, rotifers, roundworms, ribbon worms, clams, snails, octopuses, segmented worms, crustaceans, insects, bryozoans, brachiopods, phoronids, sea stars, sea urchins, tunicates, lancelets, vertebrates, including human, plants, fungi, yeast, bacteria, archaebacteria or viruses or is an artificial protein or polypeptide. By "derived" is meant that the sequence of a desired non-spidroin protein or polypeptide according to the invention has preferably at least 50% identity, preferably at least 60%, preferably at least 70%, more preferably at least 80% identity, or even at least 90% identity, such as 95-100% identity, to a corresponding naturally occurring protein and having a maintained function. In one preferred embodiment, the desired non-spidroin protein or polypeptide is derived from molluscs, insects, vertebrates, including human, plants, fungi, yeast, bacteria, archaebacteria or viruses or is an artificial protein or polypeptide. In a preferred embodiment, the desired non-spidroin protein or polypeptide is derived from vertebrates, including human, plants, fungi, yeast, bacteria, archaebacteria or viruses or is an artificial protein or polypeptide.

In a preferred embodiment, the desired non-spidroin protein or polypeptide is selected from the group consisting of amyloid-forming proteins and polypeptides, disulphide-containing proteins and polypeptides, apolipoproteins, membrane proteins and polypeptides, protein and polypeptide drugs and drug targets, aggregation-prone proteins and polypeptides, and proteases.

Amyloid-forming proteins and polypeptides according to the invention include proteins and polypeptides that are associated with disease and functional amyloid. Examples of amyloid-forming proteins and polypeptides include amyloid beta peptide (Aβ-peptide), islet amyloid polypeptide (amylin or IAPP), prion protein (PrP), α-synuclein, calcitonin, prolactin, cystatin, atrial natriuretic factor (ATF) and actin. Examples of amyloid-forming proteins and polypeptides according to the invention are listed in Table 3.

TABLE 3

Amyloid-forming proteins and polypeptides

| Protein | Uniprot ID |
|---|---|
| Aβ1-42 | P05067 |
| Apolipoprotein SAA | P02735 |
| Cystatin C | P01034 |
| Transthyretin | P02766 |
| Lysozyme | P61626 |
| α-synuclein | P37840 |
| Prion protein | P04156 |
| ODAM | A1E959 |
| Lactadherin | Q08431 |
| Tau | P10636 |
| Gelsolin | P06396 |
| ABri, ADan | Q9Y287 |
| Insulin | P01308 |
| Apolipoprotein A-II | P02652 |
| Apolipoprotein A-IV | P06727 |
| Semenogelin I | P04279 |
| Keratoepithelin | Q15582 |
| Lactotransferrin | P02788 |
| Fibrinogen α-chain | P02671 |
| ANF | P01160 |
| IAPP | P10997 |
| β2-microglobulin | P61769 |
| Calcitonin | P01258 |
| Prolactin | P01236 |
| Apolipoprotein A-I | P02647 |
| CsgA | P28307 |
| Sup35 | C7GN25 |
| Pmel17 | P40967 |
| HET-s | A8HR89 |
| Ure2p | Q8NIE6 |

Examples of disulphide-containing proteins and polypeptides include surfactant protein B (SP-B) and variants thereof, such as Mini-B, Mini-B27, Mini-BLeu, α-defensins and β-defensins. Without being limited to any specific theory, it is contemplated that the solubility-enhancing moiety promotes the desired formation of intrachain disulphide bonds over interchain disulphide bonds in defensins and other disulphide-containing proteins and polypeptides. Examples of disulphide-containing proteins and polypeptides according to the invention are listed in Table 4.

TABLE 4

Disulphide-containing proteins and polypeptides

| Protein | Sequence/Uniprot ID |
|---|---|
| Human SP-B | FPIPLPYCWLCRALIKRIQAMIPKGALAVAVAQVCRVVPL VAGGICQCLAERYSVILLDTLLGRMLPQLVCRLVLRCSM [a] |
| Mouse SP-B | LPIPLPFCWLCRTLIKRVQAVIPKGVLAVAVSQVCHVVPL VVGGICQCLAERYTVLLLDALLGRVVPQLVCGLVLRCST [a] |
| Pig SP-B | FPIPLPFCWLCRTLIKRIQAVVPKGVLLKAVAQVCHVVPL PVGGICQCLAERYIVICLNMLLDRTLPQLVCGLVLRCSS [a] |
| Rabbit SP-B | FPIPLPLCWLCRTLLKRIQAMIPKGVLAMAVAQVCHVVPL VVGGICQCLAERYTVILLEVLLGHVLPQLVCGLVLRCSS [a] |
| Rat SP-B | LPIPLPFCWLCRTLIKRVQAVIPKGVLAVAVSQVCHVVPL VVGGICQCLAERYTVLLLDALLGRVVPQLVCGLVLRCST [a] |
| Mini-B | CWLCRALIKRIQAMIPKGGRMLPQLVCRLVLRCS [b] |
| Mini-BLeu | CWLCRALIKRIQALIPKGGRLLPQLVCRLVLRCS [b] |
| Mini-B27 | CLLCRALIKRFNRYLTPQLVCRLVLRC [c] |
| 1a AA | CWLARALIKRIQALIPKGGRLLPQLVARLVLRCS [d] |
| 1b AA | AWLCRALIKRIQALIPKGGRLLPQLVCRLVLRAS [e] |
| 1a LL | CWLLRALIKRIQALIPKGGRLLPQLVLRLVLRCS [d] |
| 1b LL | LWLCRALIKRIQALIPKGGRLLPQLVCRLVLRLS [e] |
| Proinsulin | P01308 |
| CAR D1 [f] | P78310 |
| Brichos | SEQ ID NO: 41 |

[a] Cys8-Cys77, Cys11-Cys71, Cys35-Cys46 and intermolecular Cys48-Cys48 linkages
[b] Cys1-Cys33 and C4-C27 linkages
[c] Cys1-Cys27 and C4-C21 linkages
[d] Cys1-Cys33 linkage
[e] Cys4-Cys27 linkage
[f] Coxsackievirus and adenovirus receptor Examples of apolipoproteins include class A-H apolipoproteins. Examples of apolipoproteins according to the invention are listed in Table 5.

TABLE 5

Apolipoproteins

| Protein | Sequence/Uniprot ID |
|---|---|
| Apolipoprotein B-100 | P04114 |
| Apolipoprotein C-1 | P02654 |
| Apolipoprotein D | P05090 |
| Apolipoprotein E | P02649 |

Examples of membrane proteins and polypeptides include membrane-associated receptors, including cytokine receptors, KL4, LL-37, surfactant protein C(SP-C) and variants thereof, such as SP-C(Leu), SP-C33, SP-C30 and SP-C33Leu. Other specific examples include SP-C33Leu fused to Mini-B,Mini-BLeu, 1a AA, 1b AA, 0 AAAA, 1a LL, 1b LL, 0 LLLL or SP-B proteins, optionally via a linker, e.g. $Gly_n$, $Leu_n$, $Gly\text{-}Ala_n$ or the like. SP-C33Leu may be arranged N-terminal or, preferably, C-terminal to the Mini-B,Mini-BLeu, 1a AA, 1b AA, 0 AAAA, 1a LL, 1b LL, 0 LLLL or SP-B protein. Examples of membrane proteins and polypeptides according to the invention are listed in Table 6.

TABLE 6

Membrane proteins and polypeptides

| Protein | Sequence |
|---|---|
| SP-C | FGIPCCPVHLKRLLIVVVVVVLIVVVIV GALLMGL * |
| SP-C(Leu) | FGIPSSPVHLKRLKLLLLLLLLILLLILGALLMGL |
| SP-C33 | IPSSPVHLKRLKLLLLLLLLILLLILGALLMGL |
| SP-C30 | IPSSPVHLKRLKLLLLLLLLILLLILGALL |
| SP-C33(Leu) | IPSSPVHLKRLKLLLLLLLLILLLILGALLLGL |
| LL-37 | LLGDFFRKSKEKIGKEFKRIVQRIKDFLRNLV PRTES |
| KL4 | KLLLLKLLLLKLLLLKLLLLK |

* Cys-5 and Cys-6 in native SP-C are palmitoylated

| Protein | Uniprot ID |
|---|---|
| Growth hormone receptor | P10912 |
| G-protein coupled receptor 35 | Q9HC97 |
| Insulin receptor, | P06213 |
| Gonadotropin releasing hormone receptor | P30968 |

TABLE 6-continued

Membrane proteins and polypeptides

| | |
|---|---|
| Very low density lipoprotein receptor | P98155 |
| TGF-beta receptor, type 1 | P36897 |
| Prostaglandin D2 receptor | Q13258 |
| Receptor tyrosine-protein kinase erbB-2 (HER2) | P04626 |
| Receptor tyrosine-protein kinase erbB-4 (HER4) | Q15303 |
| Receptor tyrosine-protein kinase erbB-3 (HER3) | P21860 |
| Aquaporin-1 | P29972 |
| Aquaporin-2 | P41181 |
| Chloride channel protein CIC-Ka | P51800 |
| Chloride channel protein CIC-Kb | P51801 |
| Integral membrane protein DGCR2/IDD | P98153 |
| Interleukin 9 receptor | Q01113 |

Examples of protein and polypeptide drugs and drug targets include hormones that are produced recombinantly, including peptide and protein hormones, such as erythropoietin (EPO) and growth hormone (GH), cytokines, growth factors, such as insulin-like growth factors (IGF-I and IGF-II), KL4, LL-37, surfactant protein C(SP-C) and variants thereof, such as SP-C(Leu), SP-C33, SP-C30 and SP-C33Leu. Other specific examples include SP-C33Leu fused to Mini-B,Mini-BLeu, 1a AA, 1b AA, 0 AAAA, 1a LL, 1b LL, 0 LLLL or SP-B proteins, optionally via a linker, e.g. $Gly_n$, $Leu_n$, $Gly\text{-}Ala_n$ or the like. SP-C33Leu may be arranged N-terminal or, preferably, C-terminal to the Mini-B,Mini-BLeu, 1a AA, 1b AA, 0 AAAA, 1a LL, 1b LL, 0 LLLL or SP-B protein Examples of protein and polypeptide drugs and drug targets according to the invention are listed in Table 7.

TABLE 7

Protein and polypeptide drugs and drug targets

| Protein | Sequence/Uniprot ID |
|---|---|
| Insulin-like growth factor IA | P01243 |
| Insulin like growth factor IB | P05019 |
| Growth hormone 1, variant 1 | Q6IYF1 |

TABLE 7-continued

Protein and polypeptide drugs and drug targets

| | |
|---|---|
| Growth hormone 1, variant 2 | Q6IYF0 |
| Growth hormone 2, variant 2 | B1A4H7 |
| Insulin | P01308 |
| Erythropoietin | P01588 |
| Coagulation Factor VIII | P00451 |
| Coagulation Factor IX | P00740 |
| Prothrombin | P00734 |
| Serum albumin | P02768 |
| Antithrombin III | P01008 |
| Interferon alfa | P01563 |
| Somatotropin | P01241 |
| Major pollen allergen Bet v 1-A | P15494 |
| OspA (*Piscirickettsia salmonis*) | Q5BMB7 |
| 17 kDa antigen variant of OspA (*P. salmonis*) | Q9F9K8 |
| Transforming growth factor beta-1 | P01137 |
| Transforming growth factor beta-2 | P61812 |
| Transforming growth factor beta-3 | P10600 |
| Interleukin 1 beta | P01584 |
| Interleukin 1 alfa | P01583 |
| Interleukin 2 | P60568 |
| Interleukin 3 | P08700 |
| Interleukin 4 | P05112 |
| Interleukin 5 | P05113 |
| Interleukin 6 | P05231 |
| Interleukin 7 | P13232 |
| Interleukin 8 | P10145 |
| Interleukin 9 | P15248 |
| Interleukin 10 | P22301 |
| Interleukin 12 subunit alfa | P29459 |
| Interleukin 12 subunit beta | P29460 |
| Interleukin 18 | Q14116 |
| Interleukin 21 | Q9HBE4 |
| Thymic stromal lymphopoietin | Q969D9 |
| Brichos | SEQ ID NO: 41 |
| Neuroserpin | SEQ ID NO: 49 |

| Protein | Sequence |
|---|---|
| SP-C | FGIPCCPVHLKRLLIVVVVVLIVVVIVGALLMGL [a] |
| SP-C(Leu) | FGIPSSPVHLKRLKLLLLLLLLILLLILGALLMGL |

TABLE 7-continued

Protein and polypeptide drugs and drug targets

| | |
|---|---|
| SP-C33 | IPSSPVHLKRLKLLLLLLLLILLLILGALLMGL |
| SP-C30 | IPSSPVHLKRLKLLLLLLLLILLLILGALL |
| SP-C33(Leu) | IPSSPVHLKRLKLLLLLLLLILLLILGALLLGL |
| LL-37 | LLGDFFRKSKEKIGKEFKRIVQRIKDFLRNLVPRTES |
| KL4 | KLLLLKLLLLKLLLLKLLLLK |
| 1a AA | CWLARALIKRIQALIPKGGRLLPQLVARLVLRCS [b] |
| 1b AA | AWLCRALIKRIQALIPKGGRLLPQLVCRLVLRAS [c] |
| 0 AAAA | AWLARALIKRIQALIPKGGRLLPQLVARLVLRAS |
| 1a LL | CWLLRALIKRIQALIPKGGRLLPQLVLRLVLRCS [b] |
| 1b LL | LWLCRALIKRIQALIPKGGRLLPQLVCRLVLRLS [c] |
| 0 LLLL | LWLLRALIKRIQALIPKGGRLLPQLVLRLVLRLS |

[a] Cys-5 and Cys-6 in native SP-C are palmitoylated
[b] Cys1-Cys33 linkage
[c] Cys4-Cys27 linkage Examples of aggregation-prone proteins and polypeptides include avidin, streptavidin and extracellular, ligand-binding parts of cytokine receptors. Examples of aggregation-prone proteins and polypeptides according to the invention are listed in Table 8.

TABLE 8

Aggregation-prone proteins and polypeptides

| Protein | Uniprot ID/ other reference |
|---|---|
| Streptavidin, *Streptomyces avidinii* | P22629 |
| Streptavidin, *Streptomyces lavendulae* | B8YQ01 |
| Streptavidin V1, *Streptomyces venezuelae* | Q53532 |
| Streptavidin V2, *Streptomyces venezuelae* | Q53533 |
| Putative Streptavidin, *Burkholderia mallei* (strain SAVP1) | A1V7ZO |
| Putative Streptavidin, *Burkholderia thailandensis* | Q2T1V4 |
| Putative Streptavidin, *Burkholderia mallei* | Q62EP2 |
| Core Streptavidin | GenBank: CAA77107.1 |
| M4 (quadruple mutein of Streptavidin) | J Biol Chem 280(24): 23225-23231 (2005) |
| Avidin, *Gallus gallus* | P02701 |
| | GenBank: CAC34569.1 |
| Actin | P68133 |
| Interleukin 6 receptor subunit alfa | P08887 |
| Interleukin 6 receptor subunit beta | P40189 |
| Interleukin 2 receptor subunit alfa | P01589 |
| Interleukin 2 receptor subunit beta | P14784 |
| Cytokine receptor common subunit gamma | P31785 |
| Green Fluorescent Protein (GFP) | SEQ ID NO: 44 |

Examples of proteases include protease 3C from coxsackie virus or human rhinovirus. Further examples of proteases according to the invention are listed in Table 9.

TABLE 9

Proteases

| Protease | Class | Accession no. |
|---|---|---|
| Trypsin (bovine) | serine | P00760 |
| Chymotrypsin (bovine) | serine | P00766 |
| Elastase (porcine) | serine | P00772 |
| Endoproteinase Arg-C (mouse submaxillary gland) | serine | |
| Endoproteinase Glu-C (V8 protease) (*Staphylococcus aureus*) | serine | P04188 |
| Acylamino-acid-releasing enzyme (porcine) | serine | P19205 |
| Carboxypeptidase (*Penicillium janthinellum*) | serine | P43946 |
| Proteinase K (*Tritirachium album*) | serine | P06873 |
| Subtilisin (*Bacillus subtilis*) | serine | P04189 |
| | | P29122 |
| Carboxypeptidase Y (yeast) | serine | P00729 |
| Endoproteinase Lys-C (*Lysobacter enzymogenes*) | serine | S77957 |
| Enteropeptidase (human) | serine | P98073 |
| Prothrombin | serine | P00734 |
| Factor X | serine | P00742 |
| Pepsin | aspartic | P00791 |
| | | P00790 |
| Cathepsin D (human) | aspartic | P07339 |
| HIV-1 protease | aspartic | Q9YQ34 |
| Cathepsin C | cysteine | |
| Clostripain (endoproteinase-Arg-C) (*Clostridium histolyticum*) | cysteine | P09870 |
| Papain (*Carica papaya*) | cysteine | P00784 |
| Protease 3C | cysteine | Q04107 |
| Tobacco Etch virus (TEV) | cysteine | Q0GDU8 |
| Thermolysin (*Bacillus thermo-proteolyticus*) | metallo | P00800 |
| Endoproteinase Asp-N (*Pseudomonas fragi*) | metallo | Q9R4J4 |
| Carboxypeptidase A (bovine) | metallo | P00730 |
| Carboxypeptidase B (porcine) | metallo | P00732 |
| IgA protease | metallo | Q97QP7 |

In preferred embodiments of the invention, the desired non-spidroin protein is selected from surfactant protein B (SP-B) and variants thereof, such as Mini-B, Mini-B27, Mini-BLeu, KL4, LL-37, and surfactant protein C(SP-C) and variants thereof, such as SP-C(Leu), SP-C33, SP-C30 and SP-C33Leu. Other preferred non-spidroin proteins according to the invention are neuroserpin, GFP, and the 1a AA, 1b AA, 0 AAAA, 1a LL, 1b LL and 0 LLLL proteins.

In certain preferred embodiments of the invention, the fusion protein is selected from the group consisting of SEQ ID NOS 26, 28, 30, 34, 37, 39, 42 and 47; and proteins having at least 80%, preferably at least 90%, more preferably at least 95% identity, to any of these proteins.

According to another aspect, the present invention provides an isolated polynucleic acid encoding a fusion protein according to the invention. In a preferred embodiment, the isolated polynucleic acid is selected from the group consisting of SEQ ID NOS 27, 29, 31, 38, 40, 43 and 48. In another preferred embodiment, the isolated polynucleic acid is selected from the group consisting of SEQ ID NOS 14-16, 18 and 24.

According to one aspect, the present invention provides a novel use of at least one moiety which is derived from the N-terminal (NT) fragment of a spider silk protein as a solubility enhancing moiety in a fusion protein for production of a desired protein or polypeptide. In a preferred embodiment, the desired protein or polypeptide is a spidroin protein or polypeptide. When the fusion protein comprises a single solubility-enhancing moiety which is derived from the N-terminal (NT) fragment of a spider silk protein, then it is a preferred alternative that the desired protein is a non-spidroin protein or polypeptide. In one preferred embodiment, the desired protein or polypeptide is a non-spidroin protein or polypeptide.

According to another aspect, the present invention provides a method of producing a fusion protein. The first step involves expressing in a suitable host a fusion protein according to the invention. Suitable hosts are well known to a person skilled in the art and include e.g. bacteria and eukaryotic cells, such as yeast, insect cell lines and mammalian cell lines. Typically, this step involves expression of a polynucleic acid molecule which encodes the fusion protein in *E. coli*.

The second method step involves obtaining a mixture containing the fusion protein. The mixture may for instance be obtained by lysing or mechanically disrupting the host cells. The mixture may also be obtained by collecting the cell culture medium, if the fusion protein is secreted by the host cell. The thus obtained protein can be isolated using standard procedures. If desired, this mixture can be subjected to centrifugation, and the appropriate fraction (precipitate or supernatant) be collected. The mixture containing the fusion protein can also be subjected to gel filtration, chromatography, e.g. anion exchange chromatography, dialysis, phase separation or filtration to cause separation. Optionally, lipopolysaccharides and other pyrogens are actively removed at this stage. If desired, linker peptides may be removed by cleavage in this step.

In a preferred embodiment, the obtained mixture comprises the fusion protein dissolved in a liquid medium, typically a salt buffer or cell culture medium. In one preferred embodiment, the mixture has a pH below 6.3, and preferably below 6, which promotes assembly of soluble NT domains. In another preferred embodiment, the mixture has a pH above 6.4, and preferably above 7, which prevents or decreases assembly of soluble NT domains. A pH above 6.4, such as above 7, may be particularly useful to improve solubility of fusion proteins according to the invention wherein the desired protein/polypeptide is derived from a spidroin protein or wherein the desired protein/polypeptide is an amyloid-forming or aggregation-prone protein/polypeptide.

According to a related aspect, the present invention provides a method of producing a desired protein or polypeptide. The first step involves expressing in a suitable host a fusion protein according to the invention. Suitable hosts are well known to a person skilled in the art and include e.g. bacteria and eukaryotic cells, such as yeast, insect cell lines and mammalian cell lines. Typically, this step involves expression of a polynucleic acid molecule which encodes the fusion protein in *E. coli*.

The second method step involves obtaining a mixture containing the fusion protein. The mixture may for instance be obtained by lysing or mechanically disrupting, e.g. sonicating, the host cells. The mixture may also be obtained by collecting the cell culture medium, if the fusion protein is secreted by the host cell. The thus obtained protein can be isolated using standard procedures. If desired, this mixture can be subjected to centrifugation, and the appropriate fraction (precipitate or supernatant) be collected. The mixture containing the fusion protein can also be subjected to gel filtration, chromatography, e.g. anion exchange chromatography, dialysis, phase separation or filtration to cause separation. Optionally, lipopolysaccharides and other pyrogens are actively removed at this stage. If desired, linker peptides may be removed by cleavage in this step. As set out above, this may be the most suitable form of the desired protein or polypeptide, i.e. as part of a fusion protein. It may provide a suitable handle for purification and detection and/or provide desirable properties, e.g. stability and in particular solubility.

In a preferred embodiment, the method may also comprise the step of cleaving the fusion protein to provide the desired protein or polypeptide. In this embodiment, the fusion protein is comprising at least one cleavage site arranged between at least one desired protein or polypeptide moiety and at least one solubility-enhancing moiety. In a typical fusion protein, this implies the presence of a single cleavage site between the solubility-enhancing moiety or moieties and the desired protein or polypeptide. Cleavage may be achieved using standard procedures, for instance cleavage by cyanogen bromide (CNBr) after Met residues, cleavage by hydroxylamine between Asn and Gly residues, cleavage by protease 3C between Gln and Gly residues at—XLETLFQGX—(SEQ ID NO: 120) sites, and at various other protease sites that are well known to the person skilled in the art.

The thus obtained desired protein or polypeptide can be isolated using standard procedures. If desired, this mixture can be subjected to centrifugation, and the appropriate fraction (precipitate or supernatant) be collected. The mixture containing the desired protein or polypeptide can also be subjected to gel filtration, chromatography, dialysis, phase separation or filtration to cause separation. Optionally, lipopolysaccharides and other pyrogens are actively removed at this stage. If desired, linker peptides may be removed by cleavage in this step.

In a preferred embodiment, the obtained mixture comprises the fusion protein dissolved in a liquid medium, typically a salt buffer or cell culture medium. In one preferred embodiment, the mixture has a pH below 6.3, and preferably below 6, such as in the interval 4.2-6.3 or 4.2-6, which promotes assembly of soluble NT domains. In another preferred embodiment, the mixture has a pH above 6.4, and preferably above 7, which prevents or decreases assembly of soluble NT domains. A pH above 6.4, such as above 7, may be particularly useful to improve solubility of fusion proteins according to the invention wherein the desired protein/polypeptide is derived from a spidroin protein or wherein the desired protein/polypeptide is an amyloid-forming or aggregation-prone protein/polypeptide.

Thus, the fusion protein is typically obtained as a solution in a liquid medium. By the terms "soluble" and "in solution" is meant that the fusion protein is not visibly aggregated and does not precipitate from the solvent at 60 000×g. The liquid medium can be any suitable medium, such as an aqueous medium, preferably a physiological medium, typically a buffered aqueous medium, such as a 10-50 mM Tris-HCl buffer or phosphate buffer. The liquid medium preferably has a pH of 6.4 or higher, such as 7 or higher, and/or an ion composition that prevents polymerisation of the solubility-enhancing moiety. That is, the liquid medium typically has either a pH of 6.4 or higher, such as 7 or higher, or an ion composition that prevents polymerisation of the solubility-enhancing moiety, or both.

Ion compositions that prevent polymerisation of the solubility-enhancing moiety can readily be prepared by the skilled person. A preferred ion composition that prevents polymerisation of the solubility-enhancing moiety has an ionic strength of more than 300 mM. Specific examples of ion compositions that prevent polymerisation of the solubility-enhancing moiety include above 300 mM NaCl, 100 mM phosphate and combinations of these ions having desired preventive effect on the polymerisation of the solubility-enhancing moiety, e.g. a combination of 10 mM phosphate and 300 mM NaCl.

It has been surprisingly been found that the presence of an solubility-enhancing moiety improves the stability of the solution and prevents polymer formation under these conditions. This can be advantageous when immediate polymerisation may be undesirable, e.g. during protein purification, in preparation of large batches, or when other conditions need to be optimized. It is preferred that the pH of the liquid medium is adjusted to 6.7 or higher, such as 7.0 or higher to achieve high solubility of the fusion protein. It can also be advantageous that the pH of the liquid medium is adjusted to the range of 6.4-6.8, which provides sufficient solubility of the spider silk protein but facilitates subsequent pH adjustment to 6.3 or lower.

Another aspect of the invention is based on the insight that the NT domain will form large soluble assemblies when the pH is lowered from ca 7 to 6, or more specifically from above 6.4 to below 6.3. This assembly occurs most efficiently at a pH above 4.2, i.e. in the range of 4.2-6.3, such as 4.2-6. This property can be used for affinity purification, e.g. if NT is immobilised on a column. This approach allows release of bound proteins by a shift in pH within a physiologically relevant interval, since the assembly will resolve when pH is elevated from ca 6 to 7.

In a preferred embodiment of the methods according to the invention, the step of isolating the fusion protein involves purification of the fusion protein on an affinity medium, such as an affinity column, with an immobilized NT moiety and/or on an anion exchange medium, such as an anion exchange column. Purification of the fusion protein on an affinity medium is preferably carried out with association to an affinity medium with an immobilized NT moiety at a pH of 6.3 or lower, preferably in the range of 4.2-6.3, followed by dissociation from the affinity medium with a desired dissociation medium, e.g. having a pH of 6.4 or higher, a pH of 4.1 or lower and/or having a high ionic strength. Purification of the fusion protein on an anion exchange medium is preferably carried out with association to the anion exchange medium at a pH of 6.4 or higher, followed by dissociation from the anion exchange medium with a dissociation medium having a high ionic strength. If desired, purification of the fusion protein on an affinity medium, such as an affinity column, with an immobilized NT moiety can be combined with purification on an anion exchange medium, such as an anion exchange column. A dissociation medium having high ionic strength typically has an ionic strength of more than 300 mM, such as above 300 mM NaCl.

These two affinity-based procedures utilize the inherent properties of the solubility-enhancing moiety according to the invention. Of particular interest is the strong tendency of spidroin NT protein fragments to associate at a pH below 6.3, in particular in the range of 4.2-6.3. This can advantageously be utilized as a powerful affinity purification tool, allowing one-step purification of fusion proteins according to the invention from complex mixtures. Although chromatography is preferred, other affinity-based purification methods than chromatography can obviously be employed, such as magnetic beads with functionalized surfaces or filters with functionalized surfaces.

This insight that the NT domain will form large soluble assemblies when the pH is lowered from ca 7 to 6, or more specifically from above 6.4 to below 6.3, preferably in the range of 4.2-6.3, such as 4.2-6, is also useful when it is desired to promote assembly of NT-containing proteins, such as in a method of producing macroscopic polymers, e.g. fibers, films, foams, nets or meshes, of a spider silk protein such as those disclosed herein. A preferred method of producing polymers of an isolated spider silk protein, is comprising the steps of:

(i) providing a spider silk protein consisting of from 170 to 600 amino acid residues and comprising:
   an N-terminal fragment of from 100 to 160 amino acid residues derived from the N-terminal fragment of a spider silk protein; and
   a repetitive fragment of from 70 to 300 amino acid residues derived from the repetitive fragment of apidroin protein; and optionally
   a C-terminal fragment of from 70 to 120 amino acid residues, which fragment is derived from the C-terminal fragment of a spider silk protein;
(ii) providing a solution of said spider silk protein in a liquid medium at pH 6.4 or higher and/or an ion composition that prevents polymerisation of said spider silk protein, optionally involving removal of lipopolysaccharides and other pyrogens;
(iii) adjusting the properties of said liquid medium to a pH of 6.3 or lower, such as 4.2-6.3, and an ion composition that allows polymerisation of said spider silk protein;
(iv) allowing the spider silk protein to form solid polymers in the liquid medium, said liquid medium having a pH of 6.3 or lower, such as 4.2-6.3, and an ion composition that allows polymerisation of said spider silk protein; and
(v) isolating the solid spider silk protein polymers from said liquid medium.

The present invention will in the following be further illustrated by the following non-limiting examples.

EXAMPLES

Example 1

Production of an SP-C33Leu Fusion Protein

An expression vector was constructed comprising a gene encoding NT-MetSP-C33Leu as a fusion to $His_6$ (SEQ ID NOS: 26-27). The vector was used to transform *Escherichia coli* BL21(DE3) cells (Merck Biosciences) that were grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme was added, and the cells were incubated for 30 min on ice. Tween was added to a final concentration of 0.7%. The cells were disrupted by sonication on ice for 5 min, alternating 2 seconds on and 2 seconds off. The cell lysate was centrifuged at 20 000×g for 30 min. The supernatant was loaded on a Ni-NTA sepharose column, equilibrated with 20 mM Tris-HCl, pH 8 buffer containing 0.7% Tween. The column was washed with 20 mM Tris-HCl, pH 8 buffer containing 0.7% Tween, and the bound protein was eluted with 20 mM Tris-HCl pH 8, 300 mM imidazole buffer containing 0.7% Tween.

The eluate was subjected to SDS-PAGE on a 12% Tris-Glycine gel under reducing conditions. A major band corresponding to the fusion protein is indicated by the arrow in FIG. 3A. The yield was determined by mg purified protein from 1 liter shake flask culture grown to an $OD_{600}$ of 1. The yield was 64 mg/l. It is concluded that a fusion protein containing a single NT moiety results in surprisingly high yield in the presence of detergent in the cell lysate.

Example 2

Production of an SP-C33Leu Fusion Protein

An expression vector was constructed comprising a gene encoding $NT_2$-MetSP-C33Leu (i.e. NTNT-MetSP-C33Leu) as a fusion to $His_6$ (SEQ ID NOS: 28-29). The vector was used to transform *Escherichia coli* BL21(DE3) cells (Merck Biosciences) that were grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme was added, and the cells were incubated for 30 min on ice.

Tween was either not added or added to a final concentration of 0.7%. The cells were disrupted by sonication on ice for 5 min, alternating 2 seconds on and 2 seconds off. The cell lysate was centrifuged at 20 000×g for 30 min. The supernatants were loaded on a Ni-NTA sepharose column, equilibrated with 20 mM Tris-HCl, pH 8 buffer±0.7% Tween. The column was washed with 20 mM Tris-HCl, pH 8 buffer±0.7% Tween, and the bound protein was eluted with 20 mM Tris-HCl pH 8, 300 mM imidazole buffer±0.7% Tween.

The eluate was subjected to SDS-PAGE on a 12% Tris-Glycine gel under reducing conditions. A major band corresponding to the fusion protein is indicated by the arrow in FIG. 3B. The yield was determined by mg purified protein from 1 liter shake flask culture grown to an $OD_{600}$ of 1. The yield was 40 mg/l in the absence of Tween, and 68 mg/l in the presence of 0.7% Tween. It is concluded that a fusion protein containing two consecutive NT moieties results in surprisingly high yield in the absence of detergent in the cell lysate, and an even further increased yield in the presence of detergent in the cell lysate.

Example 3

Production of SP-C33Leu Fusion Proteins

Expression vectors are constructed comprising a gene encoding NT-MetSP-C33Leu, $NT_2$-MetSP-C33Leu and NT-MetSP-C33Leu-NT, respectively. The vectors are used to transform *Escherichia coli* BL21(DE3) cells (Merck Biosciences) that are grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells are harvested by centrifugation and resuspended in 20 mM Tris-HCl, pH 8.

Lysozyme is added, and the cells are incubated for 30 min on ice. Tween is either not added or added to a final concentration of 0.7%. The cells are disrupted by sonication on ice for 5 min, alternating 2 seconds on and 2 seconds off. The cell lysates are centrifuged at 20 000×g for 30 min.

Example 4

Preparation of NT-Sepharose

A $CysHis_6NT$ construct is used to transform *Escherichia coli* BL21(DE3) cells (Merck Biosciences). The cells are grown at 30° C. in Luria-Bertani medium containing kanamycin to an $OD_{600}$ of 0.8-1, induced with isopropyl-β-D-thiogalactopyranoside (IPTG), and further incubated for up to 4 hours at room temperature. Thereafter, cells are harvested and resuspended in 20 mM Tris-HCl, pH 8.0, supplemented with lysozyme and DNase I. After complete lysis, the 15000 g supernatants are loaded on a column packed with Ni sepharose (GE Healthcare). The column is washed extensively, and then bound proteins are eluted with 100-300 mM imidazole. Fractions containing the target proteins are pooled and dialyzed against 20 mM Tris-HCl, pH 8.0. Purified $Cys-His_6$-NT protein is coupled to activated thiol Sepharose using standard protocol (GE Healthcare).

Example 5

Purification of Fusion Proteins Using Nt Sepharose

Cell lysates from Example 3 are loaded on a column packed with NT sepharose, pre-equilibrated with 20 mM NaPi, pH 6. The column is washed extensively with 20 mM NaPi, pH 6 and then bound proteins are eluted with 20 mM NaPi, pH 7. Fractions containing the target proteins are pooled. Protein samples are separated on SDS-PAGE gels and then stained with Coomassie Brilliant Blue R-250. Protein content is determined from absorbance at 280 nm.

Example 6

Purification of Fusion Proteins on Anion Exchanger

Cell lysates from Example 3 are loaded on a HiTrap Q FF column (GE Healthcare), pre-equilibrated with 20 mM NaP pH 6.5. The column is washed extensively and then bound proteins are eluted with a linear gradient of NaCl up to 1 M. Fractions containing the target proteins are pooled. Protein samples are separated on SDS-PAGE gels and then stained with Coomassie Brilliant Blue R-250. Protein content is determined from absorbance at 280 nm.

Example 7

Cleavage and Isolation of Desired Protein

The fusion proteins of Examples 3, 5 and 6 are dissolved in 70% aqueous formic acid, supplemented with 0.1 g/ml CNBr and left at room temp. for 24 hours. Thereafter the mixtures are dried, and separated in the two-phase system chloroform/methanol/water, 8:4:3, by vol. SP-C33Leu is found in the organic phase and can thereafter optionally be further purified with reversed-phase HPLC using a C18 column. The activity of SP-C33Leu mixed with synthetic phospholipids can be tested in vitro or in vivo, as described in e.g. J. Johansson et al., J. Appl. Physiol. 95, 2055-2063 (2003).

Example 8

Production of LL-37 Fusion Protein

An expression vector was constructed comprising a gene encoding $NT_2$-LL37 (i.e. NTNT-LL37) as a fusion to $His_6$ (SEQ ID NOS: 30-31). The vector was used to transform Escherichia coli BL21(DE3) cells (Merck Biosciences) that were grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme was added, and the cells were incubated for 30 min on ice. The cells were disrupted by sonication on ice for 5 min, alternating 2 seconds on and 2 seconds off. The cell lysate was centrifuged at 20 000×g for 30 min. The supernatants were loaded on a Ni-NTA sepharose column, equilibrated with 20 mM Tris-HCl, pH 8, 250 mM NaCl buffer. The column was washed with 20 mM Tris-HCl, pH 8, 250 mM NaCl buffer, and the bound protein was eluted with 20 mM Tris-HCl pH 8, 300 mM imidazole buffer.

Example 9

Production of $NT$-$REP_4$-$CT$

An expression vector was constructed to produce NT-$REP_4$-CT as an N-terminal fusion to $His_6$ (SEQ ID NOS 17-18). The vector was used to transform Escherichia coli BL21(DE3) cells (Merck Biosciences) that were grown at 30° C. in Luria-Bertani medium containing kanamycin to an $OD_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I.

After complete lysis, the 15000 g supernatants were loaded onto a column packed with Ni-Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0).

Protein samples were separated via SDS-PAGE and then stained with Coomassie Brilliant Blue R-250. The resulting NT-$REP_4$-CT protein was concentrated by ultrafiltration using a 5 kDa molecular mass cutoff cellulose filter (Millipore).

Example 10

Production of NT-$REP_4$-CT

An expression vector was constructed to produce NT-$REP_4$-CT as a C-terminal fusion to Zbasic (SEQ ID NO 19). The vector was used to transform Escherichia coli BL21(DE3) cells (Merck Biosciences) that were grown at 30° C. in Luria-Bertani medium containing kanamycin to an $OD_{600}$ of ~1, induced with isopropyl-β-D-thiogalactopyranoside (IPTG), and further incubated for up to 2-4 hours at room temperature. Thereafter, cells were harvested and resuspended in 50 mM Na phosphate (pH 7.5) supplemented with lysozyme and DNase I.

After complete lysis, the 15000 g supernatants were loaded onto cation exchanger (HiTrap S, GE Healthcare, Uppsala, Sweden). The column was washed extensively before bound proteins were eluted with a gradient against 500 mM NaCl. Fractions containing the target proteins were pooled and dialyzed against 50 mM Na phosphate (pH 7.5). The NT-$REP_4$-CT protein (SEQ ID NO 20) was released from the Zbasic tags by proteolytic cleavage using a protease 3C:fusion protein ratio of 1:50 (w/w) at 4° C. over night. To remove the released Zbasic tag, the cleavage mixture was loaded onto a second cation exchanger, and the flowthrough was collected.

Example 11

Production of NT-$REP_4$-CT

An expression vector was constructed to produce NT-$REP_4$-CT as an C-terminal fusion to H isTrxHis (SEQ ID NO 21). The vector was used to transform Escherichia coli BL21(DE3) cells (Merck Biosciences) that were grown at 30° C. in Luria-Bertani medium containing kanamycin to an $OD_{600}$ of ~1, induced with isopropyl-β-D-thiogalactopyranoside (IPTG), and further incubated for up to 2-4 hours at room temperature. Thereafter, cells were harvested and resuspended in 20 mM Tris-HCl (pH 8.0) supplemented with lysozyme and DNase I.

After complete lysis, the 15000 g supernatants were loaded onto column packed with Ni-Sepharose (GE Healthcare, Uppsala, Sweden). The column was washed extensively before bound proteins were eluted with a gradient against 500 mM NaCl. Fractions containing the target proteins were pooled and dialyzed against 20 mM Tris-HCl (pH 8.0). The NT-$REP_4$-CT protein (SEQ ID NO 22) was released from the HisTrxHis tags by proteolytic cleavage using a thrombin:fusion protein ratio of 1:1000 (w/w) at 4° C. over night. To remove the released H isTrxHis, the cleavage mixture was loaded onto a second Ni-Sepharose column, and the flowthrough was collected.

Example 12

Production of $NT_2$-$REP_4$-CT

An expression vector was constructed comprising a gene encoding $NT_2$-$REP_4$-CT (i.e. NTNT-$REP_4$-CT) as a fusion to $His_6$ (SEQ ID NOS: 23-24). The vector was used to transform Escherichia coli BL21(DE3) cells (Merck Biosciences) that were grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells were harvested by centrifugation and resuspended in 20 mM Tris-HCl, pH 8.

Lysozyme and DNase were added, and the cells were incubated for 30 min on ice. The cell lysate was centrifuged at 20 000×g for 30 min. The supernatants were loaded on a Ni-NTA sepharose column, equilibrated with 20 mM Tris-HCl, pH 8 buffer. The column was washed with 20 mM Tris-HCl, pH 8 buffer, and the bound protein was eluted with 20 mM Tris-HCl pH 8, 300 mM imidazole buffer.

The eluate was subjected to SDS-PAGE on a 12% Tris-Glycine gel under reducing conditions. A major band corresponding to the fusion protein is indicated by the arrow in FIG. 3C. The yield was determined by mg purified protein from 1 liter shake flask culture grown to an $OD_{600}$ of 1. The yield was 30 mg/l. It is concluded that spidroin miniature proteins can advantageously be expressed as fusions with two NT moieties.

Example 13

Production of NT-REP$_4$-CT NT$_2$-REP$_4$-CT and NT-REP$_8$-CT

Expression vectors are constructed comprising a gene encoding NT-REP$_4$-CT (SEQ ID NOS 20 and 22), NT$_2$-REP$_4$-CT (SEQ ID NO 23), and NT-REP$_8$-CT (SEQ ID NO: 25), respectively. The vectors are used to transform *Escherichia coli* BL21(DE3) cells (Merck Biosciences) that are grown at 30° C. in Luria-Bertani medium containing kanamycin to an $OD_{600}$ of 0.9-1, induced with isopropyl-β-D-thiogalactopyranoside (IPTG), and further incubated for 3 hours at 25° C. The cells are harvested by centrifugation and resuspended in 20 mM Tris-HCl, pH 8.

Lysozyme is added, and the cells are incubated for 30 min on ice. Tween is either not added or added to a final concentration of 0.7%. The cell lysates are centrifuged at 20 000×g for 30 min. One portion of the supernatant is loaded on an anion exchange column in accordance with Example 6.

An NT affinity medium is prepared as described in Example 4. Another portion of the supernatant is loaded on an NT affinity column in accordance with Example 5.

Eluates from the anion exchange column and the NT affinity column are subjected to gel electrophoresis.

Example 14

Production of NTHis NT$_2$-REP$_8$-CT and NT$_2$-Brichos

A) NTHis

An expression vector was constructed to produce NT as an N-terminal fusion to His$_6$ (SEQ ID NO 32). The vector was used to transform *Escherichia coli* BL21(DE3) cells (Merck Biosciences) that were grown at 30° C. in Luria-Bertani medium containing kanamycin to an $OD_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I.

After complete lysis, the 15000 g supernatants were loaded onto a column packed with Ni-Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0). Protein samples were separated via SDS-PAGE and then stained with Coomassie Brilliant Blue R-250. The resulting NT protein (SEQ ID NO 32) was concentrated by ultrafiltration using a 5 kDa molecular mass cutoff cellulose filter (Millipore). The yield was 112 mg/liter shake flask grown to an $OD_{600}$ of 1.

B) NT$_2$-REP$_8$-CT

An expression vector was constructed to produce NT$_2$-REP$_8$-CT (NTNT8REPCT) as an N-terminal fusion to His$_6$ (SEQ ID NO 33). The vector were used to transform *Escherichia coli* BL21(DE3) cells (Merck Biosciences) that were grown at 30° C. in Luria-Bertani medium containing kanamycin to an $OD_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I. Protein samples were separated via SDS-PAGE and then stained with Coomassie Brilliant Blue R-250 to confirm protein expression.

After complete lysis, the 15000 g supernatants are loaded onto a column packed with Ni-Sepharose (GE Healthcare, Uppsala, Sweden). The column is washed extensively before bound proteins are eluted with 300 mM imidazole. Fractions containing the target proteins are pooled and dialyzed against 20 mM Tris-HCl (pH 8.0). Protein samples are separated via SDS-PAGE and then stained with Coomassie Brilliant Blue R-250.

C) NT$_2$-Brichos

An expression vector was constructed to produce NT$_2$-Brichos (NT-NT-Brichos) as an N-terminal fusion to His$_6$ (SEQ ID NO 34). The vector was used to transform *Escherichia coli* BL21(DE3) cells (Merck Biosciences) that were grown at 30° C. in Luria-Bertani medium containing kanamycin to an $OD_{600}$ of ~1, induced with isopropyl-β-D-thiogalactopyranoside (IPTG), and further incubated for up to 4 hours at room temperature. Thereafter, cells were harvested and resuspended in 20 mM Tris-HCl (pH 8.0) supplemented with lysozyme and DNase I. The cells were further disrupted by sonication on ice for 5 minutes, 2 seconds on and 2 seconds off.

After complete lysis, the 15000 g supernatants were loaded onto a column packed with Ni-Sepharose (GE Healthcare, Uppsala, Sweden). The column was washed extensively before bound proteins were eluted with 300 mM imidazole. Fractions containing the target proteins were pooled and dialyzed against 20 mM Tris-HCl (pH 8.0). Protein samples were separated via SDS-PAGE and then stained with Coomassie Brilliant Blue R-250. The resulting NT$_2$-Brichos protein (SEQ ID NO 34) was concentrated by ultrafiltration using a 5 kDa molecular mass cutoff cellulose filter (Millipore). The yield was 20 mg/liter shake flask grown to an $OD_{600}$ of 1.

Example 15

NT for pH-Dependent, Reversible Capture

Purpose: Use covalently immobilised NT (and NTNT) to reversibly capture NT fusion proteins.

Strategy: Investigate pH dependent assembly of NT (and NTNT) fusion proteins to fibers (and film) with covalently linked NT (and NTNT). Fibers and films without NT are used as control.

A) Fibers

Fibers (~0.5 cm long, ~50 μg) of NT-REP$_4$-CT (SEQ ID NO 20), NT$_2$-REP$_4$-CT (SEQ ID NO 23) and REP$_O$-CT (SEQ ID NO 2, control) were submerged in 100 μl solution of 5 mg/ml soluble NTHis (SEQ ID NO 32) or NT$_2$-Brichos (SEQ ID NO 34) at pH 8 for 10 minutes. The pH was decreased by addition of 400 μl sodium phosphate buffer (NaP) to pH 6 and incubated for 10 minutes to allow assembly of soluble NT to the fiber. The fibers were transferred to 500 μl of NaP at pH 6, and washed twice. Finally, the fibers were transferred to 500 μl of NaP at pH 7, and incubated 10 minutes to allow release of soluble NT. The same was done in the presence of 300 mM NaCl in all pH 6 NaP buffers. Samples from the different solutions were analysed on SDS-PAGE.

Using the NT$_2$-REP$_4$-CT and NT-REP$_4$-CT fibers, both NTHis and NT$_2$-Brichos were captured at pH 6. Upon pH raise to pH 7, both NTHis and NT$_2$-Brichos) were released again and could be detected on SDS-PAGE. The addition of 300 mM NaCl decreased capture at pH 6.

B) Film:

Films of NT-REP$_4$-CT (SEQ ID NO 20) and REP$_O$-CT (SEQ ID NO 2, control) were prepared by casting 50 µl of a protein solution of 3 mg/ml in a plastic well and left to dry over night. The next day, 100 µl solution of 5 mg/ml soluble NTHis (SEQ ID NO 32) at pH 8 was added to wells with film, and left for 10 minutes. The pH was then decreased to 6 by addition of 400 µl NaP and incubated for 10 minutes to allow assembly of soluble NT to the film. The films were then washed twice with 500 µl of NaP at pH 6. For release of soluble NTHis, 500 µl of NaP at pH 7 was added and incubated for 10 minutes. The same was done in presence of 300 mM NaCl in all pH 6 NaP buffers. Samples from the different solutions were analysed on SDS-PAGE.

Analysis on SDS-PAGE showed that a NT-REP$_4$-CT film allowed NTHis to be captured at pH 6 and released again upon raise of the pH to 7.

Example 16

NT for pH-dependent, Reversible Assembly of Fusion Proteins

Purpose: Use NT as a reversible tag that allows analysis of interaction between protein moieties, e.g. analyse the interaction of Brichos with targets with beta sheet structures e.g. surfactant protein C(SP-C).

NT$_2$-Brichos (SEQ ID NO 34) is mixed with either NT$_2$-MetSP-C33Leu (SEQ ID NO 28) or NTHis (SEQ ID NO 32) to a total volume of 100 µl at pH 8. NaP buffer (400 µl) is added to give a final pH of 6, and the mixture is incubated for 20 minutes to allow NT assembly. The pH is then raised again to pH 7 to allow reversal of NT assembly. Samples from the different solutions are analysed on native gel and size exclusion chromatography (SEC).

Example 17

Cleavage of NT-MetSP-C33Leu and Isolation of SP-C33Leu

About 58 mg of lyophilized HisNT-MetSP-C33Leu (SEQ ID NOS: 26) obtained in Example 1 was dissolved in 3 ml of 70% aqueous formic acid by vortexing and sonication. To this solution, 200 µl of 5 M CNBr in acetonitrile was added, and the mixture was incubated at room temperature for 24 h. Thereafter solvents were evaporated under a stream of nitrogen, and the residue was washed three times by solubilisation in 70% aqueous formic acid and drying under nitrogen.

To the dried residue was then added 4.56 ml of chloroform/methanol/water (8:4:3, by vol), after which the mixture was vortexed and centrifuged. The upper phase was removed, and 1 ml of chloroform/methanol/water (8:4:3, by vol) was added to the lower phase, and vortexing, centrifugation and removal of upper phase were repeated. The two upper phases were combined and dried under vacuum. The lower phase was dried under nitrogen.

Figure 4:
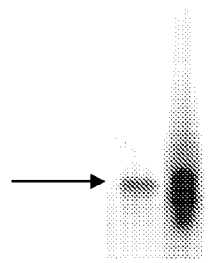
FIG. 4 shows an electrophoresis gel of a SP-C33Leu protein obtained from a fusion protein.

The contents of the lower (left lane) and upper (right lane) phases were analyzed by SDS-PAGE (FIG. 4). This showed that the lower phase contains one major band with an estimated molecular mass that agrees well with that of SP-C33Leu. The identity of SP-C33Leu was confirmed by ESI mass spectrometry and amino acid sequencing, which showed a monoisotopic mass of 3594.6 Da (calculated 3594.4 Da) and the expected amino acid sequence.

Example 18

Analysis of Surface Activity of Sp-C33Leu/Phospholipid Mixture 1,2-Dipalmitoyl-sn-glycero-3-phosphocholine (DPPC)/1-palmitoyl-2-oleoyl-sn-glycero-3-phosphoglycerol (POPG) (68:31, w/w) was dissolved in chloroform:methanol (1:1, v/v) and mixed with SP-C33Leu (obtained in Example 17) in the same solvent. The peptide content in the preparations was 2% in relation to the phospholipid weight. The solvents were evaporated with nitrogen, and the preparations were resuspended in saline to a final phospholipid concentration of 10 mg/ml by slow rotation at 37° C.

Surface tension was measured in triplicates in an alveolus by a captive bubble surfactometer (CBS) (Schurch S et al., J. Appl. Physiol. 67: 2389-2396, 1989). In the CBS, surfactant and an air-bubble representing the lung alveolus are present in an air-tight enclosed chamber. To evaluate surface activity under dynamic circumstances, the chamber is compressed and surface tension can be calculated by studying the shape and height/width ratio of the bubble.

In the experiment, 2 µl of the SP-C33Leu surfactant preparation (10 mg/ml) was inserted into the sucrose-filled test chamber. After insertion, an air-bubble was created and surface tension was measured during five minutes of adsorption. In the following quasi-static cycling experiments, the bubble was compressed stepwise from the initial volume until a surface tension less than 5 mN/m was reached, alternatively to a maximum area compression of 50% and then expanded during five cycles.

Figure 5:
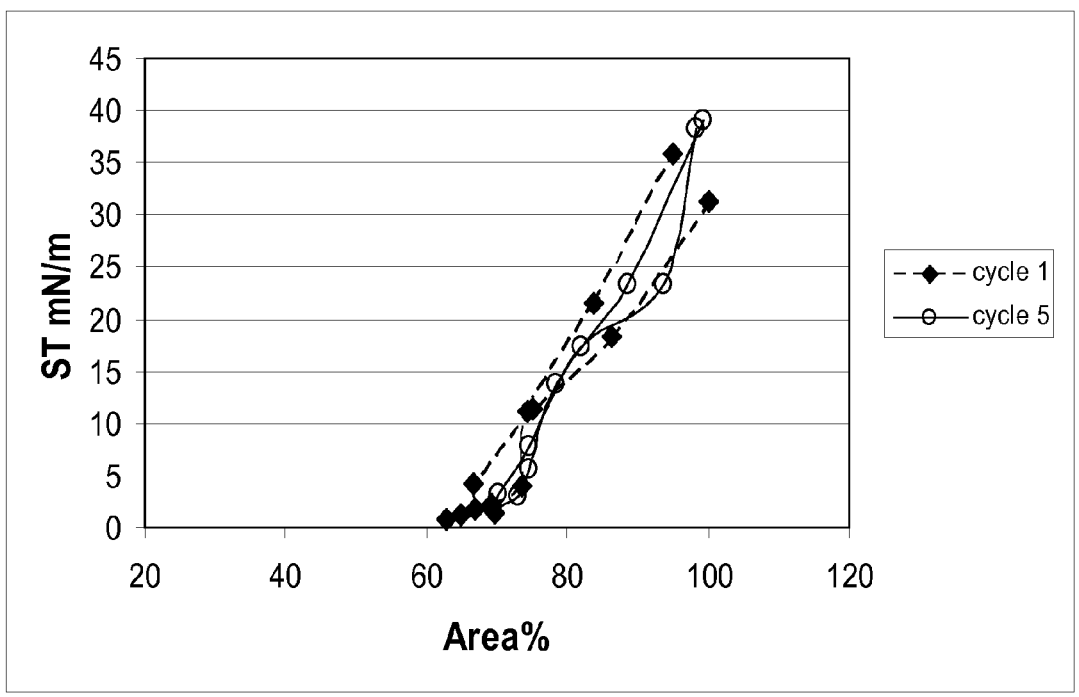
FIG. 5 shows in vitro surface activity of surfactant suspensions comprising SP-C33Leu obtained from a fusion protein.

The results are illustrated in FIG. 5, where the first and fifth cycle from one representative example out of three measurements are shown. The surface activity of the SP-C33Leu/DPPC/POPG mixture (FIG. 5) was very similar to that of synthetic SP-C33 in the same phospholipid mixture, see e.g. Johansson et al, J. Appl. Physiol, 95: 2055-2063 (2003).

Example 19

Production of an SP-C33Leu Fusion Protein

A) Without NT (Comparative Example)

An expression vector was constructed comprising a gene encoding Thioredoxin (TRX)-SP-C33Leu as a fusion to 2×His$_6$ (SEQ ID NOS: 35-36). The vector was used to transform *Escherichia coli* BL21(DE3) cells (Merck Biosciences) that were grown at 30° C. in Luria-Bertani medium containing kanamycin to an OD$_{600}$ of 0.9-1, induced with IPTG and further incubated for 3 hours at 25° C. The cells were harvested and resuspended in 20 mM Tris-HCl (pH 8.0).

Lysozyme was added, and the cells were incubated for 30 min on ice. Tween was added to a final concentration of 0.7%. The cells were disrupted by sonication on ice for 5 min, alternating 2 sec on and 2 sec off. The cell lysate was centrifuged at 20 000×g for 30 min. The supernatants were loaded onto a column packed with Ni-Sepharose (GE Healthcare, Uppsala, Sweden), equilibrated with 20 mM Tris-HCl (pH 8.0)+0.7% Tween. The column was washed extensively before bound proteins were eluted with a 300 mM imidazole+0.7% Tween.

The target protein was eluted with 300 mM imidazole+ 0.7% Tween and analyzed by SDS-PAGE (FIG. 6A). The eluate contained a small and impure amount of target protein.

B) With NT

An expression vector was constructed comprising a gene encoding TRX-NT-SP-C33Leu as a fusion to 2×His6 (SEQ ID NOS:37-38). The vector was used to transform *Escherichia coli* BL21(DE3) cells (Merck Biosciences) that were grown at 30° C. in Luria-Bertani medium containing kanamycin to an $OD_{600}$ of 0.9-1, induced with IPTG, and further incubated for 3 hours at 25° C. The cells were harvested and resuspended in 20 mM Tris-HCl (pH 8.0).

Lysozyme was added, and the cells were incubated for 30 min on ice. Tween was added to a final concentration of 0.7%. The cells were disrupted by sonication on ice for 5 min, alternating 2 sec on and 2 sec off. The cell lysate was centrifuged at 20 000×g for 30 min. The supernatants were loaded onto a column packed with Ni-Sepharose (GE Healthcare, Uppsala, Sweden), equilibrated with 20 mM Tris-HCl (pH 8.0)+0.7% Tween. The column was washed extensively before bound proteins were eluted with a 300 mM imidazole+0.7% Tween. Fractions containing the fusion proteins were pooled and dialyzed against deionized water.

The eluate was subjected to SDS-PAGE on a 12% Tris-Glycine gel under reducing conditions. A major band corresponding to the protein is indicated by the arrow in FIG. 6B. The yield was determined by mg purified protein from 1 liter shake flask culture grown to an $OD_{600}$ of 1. The yield was 30 mg/l.

Example 20

Production of Brichos

An expression vector was constructed comprising a gene encoding $NT_2$-Brichos (i.e. NTNT-Brichos) as a fusion to $His_6LinkHis_6$ (SEQ ID NOS:39-40). The vector was used to transform *Escherichia coli* BL21(DE3) cells (Merck Biosciences) that were grown at 30° C. in Luria-Bertani medium containing kanamycin to an $OD_{600}$ of 0.9-1, induced with IPTG, and further incubated for 3 hours at 25° C. The cells were harvested and resuspended in 20 mM Tris-HCl (pH 8.0).

Lysozyme was added, and the cells were incubated for 30 min on ice. The cells were disrupted by sonication on ice for 5 min, alternating 2 sec on and 2 sec off. The cell lysate was centrifuged at 20 000×g for 30 min. The supernatants were loaded onto a column packed with Ni-Sepharose (GE Healthcare, Uppsala, Sweden). The column was washed extensively before bound proteins were eluted with a 300 mM imidazole. Fractions containing the fusion proteins were pooled and dialyzed against 20 mM Tris-HCl (pH 8.0).

The eluate was subjected to SDS-PAGE on a 12% Tris-Glycine gel under reducing conditions. A major band corresponding to the fusion protein is indicated by the arrow in FIG. 7. The yield was determined by mg purified protein from 1 liter shake flask culture grown to an $OD_{600}$ of 1. The yield was 28 mg/l of the fusion protein.

The Brichos protein (SEQ ID NO: 41) is released from the 2H is$_6$NT$_2$ tags by proteolytic cleavage using a protease 3C:fusion protein ratio of 1:100 (w/w) at 4° C. To remove the released 2H is$_6$NT$_2$ tag, the cleavage mixture is loaded onto a second Ni-Sepharose, and the flow through is collected.

Example 21

Production of Green Fluorescent Protein (GFP)

The GFP utilized in this example is a S147P variant, see Kimata, Y et al., Biochem. Biophys. Res. Commun. 232: 69-73 (1997).

A) With NT

An expression vector was constructed comprising a gene encoding $NT_2$-GFP (i.e. NTNT-GFP) as a fusion to $His_6LinkHis_6$ (SEQ ID NOS:42-43). The vector was used to transform *Escherichia coli* BL21(DE3) cells (Merck Biosciences) that were grown at 30° C. in Luria-Bertani medium containing kanamycin to an $OD_{600}$ of 0.9-1, induced with IPTG, and further incubated for 3 hours at 25° C. The cells were harvested and resuspended in 20 mM Tris-HCl (pH 8.0).

Lysozyme was added, and the cells were incubated for 30 min on ice. The cells were disrupted by sonication on ice for 5 min, alternating 2 sec on and 2 sec off. The cell lysate was centrifuged at 20 000×g for 30 min. The supernatants were loaded onto a column packed with Ni-Sepharose (GE Healthcare, Uppsala, Sweden). The column was washed extensively before bound proteins were eluted with a 300 mM imidazole. Fractions containing the fusion proteins were pooled and dialyzed against 20 mM Tris-HCl (pH 8.0). The GFP protein (SEQ ID NO: 44) was released from the 2H is$_6$NT$_2$ tags by proteolytic cleavage using a protease 3C:fusion protein ratio of 1:100 (w/w) at 4° C. To remove the released 2H is$_6$NT$_2$ tag, the cleavage mixture was loaded onto a second Ni-Sepharose, and the flow through was collected.

The eluates were subjected to SDS-PAGE on a 12% Tris-Glycine gel under reducing conditions (FIG. 8). Major bands corresponding to the fusion protein (first eluate, left lane) and the target protein (second eluate, right lane) are indicated by the arrows in FIG. 8. The yield was determined by mg purified protein from 1 liter shake flask culture grown to an $OD_{600}$ of 1. The yield was 44 mg/l of the fusion protein and 16 mg/l of the target protein.

The purified GFP was highly fluorescent, confirming the right fold (beta barrel with linking alpha helix) that is obligate for autocatalytic formation of the chromophore.

B) With Other Purification Tags: Zb and His$_6$ABP (Comparative Example)

BL21(DE3) cells harboring the vectors (pT7ZbGFP, pT7His6ABPGFP) were grown over night at 37° C. in tryptic soy broth media supplemented with kanamycin. On the following morning, the cultures were inoculated into 100 ml fresh media in 1 liter shake flasks and grown until an $OD_{600}$ of 1 was reached. Protein production was then induced by addition of IPTG to a final concentration of 1 mM, and production continued for 18 h. The cells were harvested and resuspended in 50 mM sodium phosphate buffer (pH 7.5). The cells were disrupted by sonication on ice for 3 min, alternating 1 sec on and 1 sec off. The cell lysate was centrifuged at 10 000×g for 20 min. The supernatants were loaded onto columns.

The ZbGFP (SEQ ID NO: 45) fusion protein was purified on 1 ml HiTrap S HP columns in 50 mM sodium phosphate pH 7.5 and eluted with the same buffer supplemented with 160 mM NaCl.

The His₆ABPGFP (SEQ ID NO: 46) fusion protein was purified on 1 ml Talon columns in 50 mM sodium phosphate pH 8 and eluted with the same buffer supplemented with 30 mM acetic acid and 70 mM sodium acetate, which gives a pH of 5.0.

The eluates were subjected to SDS-PAGE on a 10-20% gradient gel under reducing conditions. The yield was determined by mg purified protein/1 liter shake flask culture grown to an $OD_{600}$ of 1. The yield was 10 mg/l for ZbGFP and 7 mg/l for His₆ABPGFP.

Example 22

Production of Neuroserpin

An expression vector was constructed comprising a gene encoding NT₂-Neuroserpin (i.e. NTNT-Neuroserpin) as a fusion to His₆LinkHis₆ (SEQ ID NOS:47-48). The vector was used to transform *Escherichia coli* BL21(DE3) cells (Merck Biosciences) that were grown at 30° C. in Luria-Bertani medium containing kanamycin to an $OD_{600}$ of 0.9-1, induced with IPTG, and further incubated for 3 hours at 25° C. The cells were harvested and resuspended in 20 mM Tris-HCl (pH 8.0).

Lysozyme was added, and the cells were incubated for 30 min on ice. The cells were disrupted by sonication on ice for 5 min, alternating 2 sec on and 2 sec off. The cell lysate was centrifuged at 20 000×g for 30 min. The supernatants were loaded onto a column packed with Ni-Sepharose (GE Healthcare, Uppsala, Sweden). The column was washed extensively before bound proteins were eluted with 300 mM imidazole. Fractions containing the fusion proteins were pooled and dialyzed against 20 mM Tris-HCl (pH 8.0).

The neuroserpin protein (SEQ ID NO: 49) was released from the 2H is₆NT₂ tags by proteolytic cleavage using a protease 3C:fusion protein ratio of 1:100 (w/w) at 4° C. To remove the released 2H is₆NT₂ tag, the cleavage mixture was loaded onto a second Ni-Sepharose, and the flow through was collected.

The eluates were subjected to SDS-PAGE on a 12% Tris-Glycine gel under reducing conditions (FIG. 9). Major bands corresponding to the fusion protein (first eluate, left lane) and the target protein (second eluate, right lane) are indicated by the arrows in FIG. 9. The yield was determined by mg purified protein from 1 liter shake flask culture grown to an $OD_{600}$ of 1. The yield was 8 mg/l of the fusionprotein and 4 mg/l of the target protein. As a comparison, the expression yield of neuroserpin with His₆ tag was 1.7 mg/l (Belorgey et al. Eur J. Biochem. 271(16):3360-3367 (2004).

The inhibition rate of tPa (tissue plasminogen activator) by the expressed neuroserpin was determined to be the same as published earlier (Belorgey et al. J. Biol. Chem. 277, 17367-17373 (2002).

Example 23

Production of a Protease 3C Fusion Proteins

Expression vectors are constructed comprising a gene encoding His₆NT-3C and His₆LinkHis₆NTNT3C, respectively (Gräslund T. et al., Protein Expr Purif 9(1): 125-132 (1997); Cordingley M G. et al., J. Virol. 63(12): 5037-5045 (1989)). The vectors are used to transform *Escherichia coli* BL21(DE3) cells (Merck Biosciences), which are grown at 30° C. in Luria-Bertani medium containing kanamycin to an $OD_{600}$ of 0.9-1, induced with IPTG, and further incubated for 3 h at 25° C. The cells are harvested and resuspended in 20 mM Tris-HCl (pH 8.0).

Lysozyme and DNase are added, and the cells are incubated for 30 min on ice. The cells are further disrupted by sonication on ice for 3 min, alternating 1 sec on and 1 sec off. The cell lysate is centrifuged at 15 000×g for 30 min. The supernatants are loaded onto a column packed with Ni-Sepharose (GE Healthcare, Uppsala, Sweden), equilibrated with 20 mM Tris-HCl (pH 8.0). The column is washed extensively before bound proteins are eluted with 300 mM imidazole. Fractions containing the fusion proteins are pooled and dialyzed against deionized water. The eluate is subjected to SDS-PAGE under reducing conditions. The yield is determined by mg purified protein from 1 liter shake flask culture grown to an $OD_{600}$ of 1.

The invention claimed is:

1. A fusion protein comprising
   (i) at least one solubility-enhancing moiety, wherein each solubility-enhancing moiety has at least 90% identity to the amino acid sequence of SEQ ID NO:6; and
   (ii) at least one moiety which is a desired non-spidroin protein or a desired non-spidroin polypeptide, wherein the desired non-spidroin protein or the desired non-spidroin polypeptide is selected from the group consisting of amyloid-forming proteins, amyloid-forming polypeptides, surfactant protein B (SP-B), variants of SP-B containing disulphide, apolipoproteins, membrane proteins, membrane polypeptides, protein drugs, polypeptide drugs, aggregation-prone proteins, aggregation-prone polypeptides, and proteases,
   wherein the desired non-spidroin protein or the desired non-spidroin polypeptide has less than 30% identity to any of the amino acid sequences of SEQ ID NO: 6-10,
   wherein each solubility-enhancing moiety is linked directly or indirectly to the desired non-spidroin protein or the desired non-spidroin polypeptide moiety, and
   wherein the desired non-spidroin protein or the desired non-spidroin polypeptide excludes thioredoxin.

2. The fusion protein according to claim 1, wherein each solubility-enhancing moiety contains from 130 to 160 amino acid residues.

3. The fusion protein according to claim 1, wherein the fusion protein comprises at least two solubility-enhancing moieties, each being defined as in claim 1.

4. The fusion protein according to claim 1, wherein the fusion protein comprises at least two consecutive solubility-enhancing moieties, each being defined as in claim 1.

5. The fusion protein according to claim 1, wherein at least one solubility-enhancing moiety is linked directly or indirectly, with intervening sequences selected from linker peptides and/or further solubility-enhancing moieties, to the amino-terminal or the carboxy-terminal end of the at least one desired non-spidroin protein or desired non-spidroin polypeptide moiety.

6. The fusion protein according to claim 5, wherein at least one solubility-enhancing moiety is linked directly or indirectly, with intervening sequences selected from linker peptides and/or further solubility-enhancing moieties, to the amino-terminal end of the at least one desired non-spidroin protein or desired non-spidroin polypeptide moiety.

7. The fusion protein according to claim 5, wherein at least one solubility-enhancing moiety constitutes the amino-terminal and/or the carboxy-terminal end of the fusion protein.

8. The fusion protein according to claim 1, further comprising
(iii) at least one cleavage site arranged between the at least one desired non-spidroin protein or desired non-spidroin polypeptide moiety and the at least one solubility-enhancing moiety.

9. The fusion protein according to claim 1, comprising a linker which constitutes a handle for identification and purification of the fusion protein.

10. The fusion protein according to claim 1, wherein the desired non-spidroin protein or the desired non-spidroin polypeptide is selected from the group consisting of amyloid beta peptide (Aβ-peptide), islet amyloid polypeptide (IAPP), prion protein (PrP), α-synuclein, calcitonin, prolactin, cystatin, atrial natriuretic factor (ATF) and actin; surface protein B (SP-B), mini-BLeu, α-defensins and β-defensins; class A-H apolipoproteins; (LL-37), surfactant protein C (SP-C), SP-C33, SP-C33Leu, Brichos, GFP, neuroserpin; hormones, including erythropoietin (EPO) and growth hormone (GH), and growth factors, including insulin-like growth factor I (IGF-I) and insulin-like growth factor II (IGF-II); avidin and streptavidin; and protease 3C.

11. The fusion protein according to claim 1, wherein the desired non-spidroin protein or the desired non-spidroin polypeptide is selected from SP-B, mini-B, mini-BLeu, 1a AA, 1b AA, 1a LL and 1b LL, and SP-C, SP-C(Leu), SP-C33, SP-C30, SP-C33(Leu) and KL4.

12. The fusion protein according to claim 11, wherein the desired non-spidroin protein or the desired non-spidroin polypeptide is mini-BLeu.

13. The fusion protein according to claim 11, wherein the desired non-spidroin protein or the desired non-spidroin polypeptide is SP-C33Leu.

14. The fusion protein according to claim 1, selected from the group consisting of the amino acid sequences of SEQ ID NOS 26, 28, 30, 34, 37, 39, 42 and 47; and proteins having at least 95% identity to any one of said amino acid sequences.

15. The fusion protein according to claim 1, wherein the desired non-spidroin protein or the desired non-spidroin polypeptide is selected from the group consisting of amyloid-forming proteins, amyloid-forming polypeptides, surfactant protein B (SP-B), apolipoproteins, membrane proteins, membrane polypeptides, and proteases.

16. The fusion protein according to claim 1, wherein the desired non-spidroin protein or the desired non-spidroin polypeptide is selected from the group consisting of aggregation-prone proteins and aggregation-prone polypeptides, wherein the desired non-spidroin protein or the desired non-spidroin polypeptide excludes thioredoxin.

17. The fusion protein according to claim 1, wherein the desired non-spidroin protein or the desired non-spidroin polypeptide is selected from the group consisting of amyloid beta peptide (Aβ-peptide), islet amyloid polypeptide (IAPP), prion protein (PrP), α-synuclein, calcitonin, prolactin, cystatin, atrial natriuretic factor (ATF) and actin; SP-B, mini-Bleu, α-defensins and β-defensins; class A-H apolipoproteins; (LL-37), surfactant protein C (SP-C), SP-C33, SP-C33Leu, Brichos, GFP, neuroserpin; hormone, insulin-like growth factor I (IGF-I) and insulin-like growth factor II (IGF-II); avidin and streptavidin; and protease 3C.

18. The fusion protein according to claim 17, wherein the hormone is erythropoietin (EPO) or growth hormone (GH).

* * * * *

SEQUENCE LISTING

```
<160> NUMBER OF SEQ ID NOS: 120

<210> SEQ ID NO 1
<211> LENGTH: 149
<212> TYPE: PRT
<213> ORGANISM: Euprosthenops australis

<400> SEQUENCE: 1

Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Ala Gly Gly Gln Gly Gly Gln Gly Gln
        35                  40                  45

Gly Gly Tyr Gly Gln Gly Ser Gly Gly Ser Ala Ala Ala Ala Ala Ala
    50                  55                  60

Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala Ala
                85                  90                  95
```

```
Ala Ala Ala Ala Gly Gln Gly Gly Gln Gly Gly Tyr Gly Arg Gln
            100             105             110

Ser Gln Gly Ala Gly Ser Ala Ala Ala Ala Ala Ala Ala Ala
        115             120             125

Ala Ala Ala Ala Gly Ser Gly Gln Gly Gly Tyr Gly Gln Gly Gln Gly
    130             135             140

Gly Tyr Gly Gln Ser
145
```

```
<210> SEQ ID NO 2
<211> LENGTH: 265
<212> TYPE: PRT
<213> ORGANISM: Euprosthenops australis
<220> FEATURE:
<221> NAME/KEY: DOMAIN
<222> LOCATION: (1)..(167)
<223> OTHER INFORMATION: REP fragment
<220> FEATURE:
<221> NAME/KEY: DOMAIN
<222> LOCATION: (168)..(265)
<223> OTHER INFORMATION: CT fragment

<400> SEQUENCE: 2
```

```
Gly Ser Gly Asn Ser Gly Ile Gln Gly Gln Gly Gly Tyr Gly Gly Leu
1               5                   10                  15

Gly Gln Gly Gly Tyr Gly Gln Gly Ala Gly Ser Ser Ala Ala Ala Ala
            20                  25                  30

Ala Ala Ala Ala Ala Ala Ala Gly Gly Gln Gly Gly Gln Gly Gln
            35                  40                  45

Gly Gly Tyr Gly Gln Gly Ser Gly Gly Ser Ala Ala Ala Ala Ala
    50                  55                  60

Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala
            85                  90                  95

Ala Ala Ala Ala Ala Gly Gln Gly Gly Gln Gly Gly Tyr Gly Arg Gln
            100             105             110

Ser Gln Gly Ala Gly Ser Ala Ala Ala Ala Ala Ala Ala Ala
        115             120             125

Ala Ala Ala Ala Gly Ser Gly Gln Gly Gly Tyr Gly Gln Gly Gln Gly
    130             135             140

Gly Tyr Gly Gln Ser Ser Ala Ser Ala Ser Ala Ala Ser Ala Ala
145                 150                 155             160

Ser Thr Val Ala Asn Ser Val Ser Arg Leu Ser Ser Pro Ser Ala Val
                165                 170                 175

Ser Arg Val Ser Ser Ala Val Ser Ser Leu Val Ser Asn Gly Gln Val
            180                 185                 190

Asn Met Ala Ala Leu Pro Asn Ile Ile Ser Asn Ile Ser Ser Val
        195                 200                 205

Ser Ala Ser Ala Pro Gly Ala Ser Gly Cys Glu Val Ile Val Gln Ala
    210                 215                 220

Leu Leu Glu Val Ile Thr Ala Leu Val Gln Ile Val Ser Ser Ser Ser
225                 230                 235                 240

Val Gly Tyr Ile Asn Pro Ser Ala Val Asn Gln Ile Thr Asn Val Val
                245                 250                 255

Ala Asn Ala Met Ala Gln Val Met Gly
            260                 265
```

<210> SEQ ID NO 3
<211> LENGTH: 296
<212> TYPE: PRT
<213> ORGANISM: Euprosthenops australis
<220> FEATURE:
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(296)
<223> OTHER INFORMATION: REP fragment

<400> SEQUENCE: 3

```
Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
        115                 120                 125

Gln Ala Gly Met Asn Asp Val Ser Ala Ser Ala Ser Ala Gly Ala Ser
    130                 135                 140

Ala Ala Ala Ser Ala Gly Ala Ala Ser Gly Gln Gly Gly Tyr Gly Gly
145                 150                 155                 160

Leu Gly Gln Gly Gly Tyr Gly Gln Gly Gly Ala Gly Ser Ser Ala Ala Ala
                165                 170                 175

Ala Ala Ala Ala Ala Ala Ala Ala Gly Gly Gln Gly Gly Gln Gly
            180                 185                 190

Gln Gly Gly Tyr Gly Gln Gly Ser Gly Gly Ser Ala Ala Ala Ala
        195                 200                 205

Ala Ala Ala Ala Ala Ala Ala Ala Gly Arg Gly Gln Gly Gly
    210                 215                 220

Tyr Gly Gln Gly Ser Gly Gly Asn Ala Ala Ala Ala Ala Ala Ala Ala
225                 230                 235                 240

Ala Ala Ala Ala Ala Ala Gly Gln Gly Gly Gln Gly Gly Tyr Gly
                245                 250                 255

Arg Gln Ser Gln Gly Ala Gly Ser Ala Ala Ala Ala Ala Ala Ala
            260                 265                 270

Ala Ala Ala Ala Ala Gly Ser Gly Gln Gly Gly Tyr Gly Gly Gln
        275                 280                 285

Gly Gln Gly Gly Tyr Gly Gln Ser
    290                 295
```

<210> SEQ ID NO 4
<211> LENGTH: 340
<212> TYPE: PRT
<213> ORGANISM: Euprosthenops australis
<220> FEATURE:

```
<221> NAME/KEY: DOMAIN
<222> LOCATION: (1)..(137)
<223> OTHER INFORMATION: NT fragment
<220> FEATURE:
<221> NAME/KEY: DOMAIN
<222> LOCATION: (138)..(340)
<223> OTHER INFORMATION: REP fragment

<400> SEQUENCE: 4

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
50                  55                  60

Lys Leu Gln Ala Leu Asn Met Ala Phe Ala Ser Ser Met Ala Glu Ile
65                  70                  75                  80

Ala Ala Ser Glu Glu Gly Gly Ser Leu Ser Thr Lys Thr Ser Ser
                85                  90                  95

Ile Ala Ser Ala Met Ser Asn Ala Phe Leu Gln Thr Thr Gly Val Val
            100                 105                 110

Asn Gln Pro Phe Ile Asn Glu Ile Thr Gln Leu Val Ser Met Phe Ala
            115                 120                 125

Gln Ala Gly Met Asn Asp Val Ser Ala Ser Ala Gly Ala Ser
130                 135                 140

Ala Ala Ala Ser Ala Gly Ala Pro Gly Tyr Ser Pro Ala Pro Ser Tyr
145                 150                 155                 160

Ser Ser Gly Gly Tyr Ala Ser Ser Ala Ala Ser Ala Ala Ala Ala
            165                 170                 175

Gly Gln Gly Gly Pro Gly Gly Tyr Gly Pro Ala Pro Asn Gln Gly Ala
            180                 185                 190

Ser Ser Ala Ala Ala Ala Ala Ala Gly Ser Gly Gln Gly Pro Ser Gly
            195                 200                 205

Pro Tyr Gly Thr Ser Tyr Gln Ile Ser Thr Gln Tyr Thr Gln Thr Thr
    210                 215                 220

Thr Ser Gln Gly Gln Gly Tyr Gly Ser Ser Ala Gly Ala Ala Ala
225                 230                 235                 240

Ala Gly Ala Ala Gly Ala Gly Gln Gly Tyr Gly Gly Gln Gly Gln
                245                 250                 255

Gly Gly Tyr Gly Gln Gly Ala Gly Gly Ala Ala Ala Ala Ala Ala
            260                 265                 270

Ala Ala Ala Ala Ala Ala Ala Gly Gln Gly Gly Gln Gly Gly
            275                 280                 285

Gly Tyr Gly Gln Gly Gly Gln Gly Gly Gln Gly Gly Gln Gly Gln Gly
    290                 295                 300

Gly Tyr Gly Gln Gly Ala Gly Ser Ser Ala Ala Ala Ala Ala Ala
305                 310                 315                 320

Ala Ala Ala Ala Ala Ala Ala Gly Arg Gly Gln Gly Gly Tyr Gly Pro
            325                 330                 335

Gly Ser Gly Gly
            340

<210> SEQ ID NO 5
<211> LENGTH: 424
```

<212> TYPE: PRT
<213> ORGANISM: Euprosthenops australis
<220> FEATURE:
<221> NAME/KEY: DOMAIN
<222> LOCATION: (1)..(136)
<223> OTHER INFORMATION: NT fragment
<220> FEATURE:
<221> NAME/KEY: DOMAIN
<222> LOCATION: (137)..(313)
<223> OTHER INFORMATION: REP fragment
<220> FEATURE:
<221> NAME/KEY: DOMAIN
<222> LOCATION: (314)..(411)
<223> OTHER INFORMATION: CT fragment
<220> FEATURE:
<221> NAME/KEY: DOMAIN
<222> LOCATION: (412)..(424)
<223> OTHER INFORMATION: His tag

<400> SEQUENCE: 5

Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
            20                  25                  30

Thr Ala Ser Gln Leu Asp Asp Met Ser Thr Ile Ala Gln Ser Met Val
        35                  40                  45

Gln Ser Ile Gln Ser Leu Ala Ala Gln Gly Arg Thr Ser Pro Asn Lys
    50                  55                  60

Leu Gln Ala Leu Asn Met Ala Phe Ala Ser Ser Met Ala Glu Ile Ala
65                  70                  75                  80

Ala Ser Glu Glu Gly Gly Gly Ser Leu Ser Thr Lys Thr Ser Ser Ile
                85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
        115                 120                 125

Ala Gly Met Asn Asp Val Ser Ala Ser Ala Ser Ala Gly Ala Ser Ala
    130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala Ala
                165                 170                 175

Ala Ala Ala Ala Ala Ala Ala Gly Gly Gln Gly Gln Gly Gly Gln Gln
            180                 185                 190

Gly Gly Tyr Gly Gln Gly Ser Gly Gly Ser Ala Ala Ala Ala Ala Ala
        195                 200                 205

Ala Ala Ala Ala Ala Ala Ala Ala Gly Arg Gly Gln Gly Gly Tyr
    210                 215                 220

Gly Gln Gly Ser Gly Gly Asn Ala Ala Ala Ala Ala Ala Ala Ala Ala
225                 230                 235                 240

Ala Ala Ala Ala Ala Ala Gly Gln Gly Gln Gly Gly Tyr Gly Arg
                245                 250                 255

Gln Ser Gln Gly Ala Gly Ser Ala Ala Ala Ala Ala Ala Ala Ala Ala
            260                 265                 270

Ala Ala Ala Ala Gly Ser Gly Gln Gly Gly Tyr Gly Gly Gln Gly
        275                 280                 285

Gln Gly Gly Tyr Gly Gln Ser Ser Ala Ser Ala Ser Ala Ala Ala Ser
    290                 295                 300

Ala Ala Ser Thr Val Ala Asn Ser Val Ser Arg Leu Ser Ser Pro Ser

```
              305                 310                 315                 320
Ala Val Ser Arg Val Ser Ser Ala Val Ser Ser Leu Val Ser Asn Gly
                325                 330                 335
Gln Val Asn Met Ala Ala Leu Pro Asn Ile Ile Ser Asn Ile Ser Ser
                340                 345                 350
Ser Val Ser Ala Ser Ala Pro Gly Ala Ser Gly Cys Glu Val Ile Val
                355                 360                 365
Gln Ala Leu Leu Glu Val Ile Thr Ala Leu Val Gln Ile Val Ser Ser
                370                 375                 380
Ser Ser Val Gly Tyr Ile Asn Pro Ser Ala Val Asn Gln Ile Thr Asn
385                 390                 395                 400
Val Val Ala Asn Ala Met Ala Gln Val Met Gly Lys Leu Ala Ala Ala
                405                 410                 415
Leu Glu His His His His His His
                420

<210> SEQ ID NO 6
<211> LENGTH: 137
<212> TYPE: PRT
<213> ORGANISM: Euprosthenops australis
<220> FEATURE:
<221> NAME/KEY: VARIANT
<222> LOCATION: (6)..(6)
<223> OTHER INFORMATION: deletion (deltaHis)

<400> SEQUENCE: 6

Gly Ser Gly Asn Ser His Thr Thr Pro Trp Thr Asn Pro Gly Leu Ala
1               5                   10                  15
Glu Asn Phe Met Asn Ser Phe Met Gln Gly Leu Ser Ser Met Pro Gly
                20                  25                  30
Phe Thr Ala Ser Gln Leu Asp Asp Met Ser Thr Ile Ala Gln Ser Met
                35                  40                  45
Val Gln Ser Ile Gln Ser Leu Ala Ala Gln Gly Arg Thr Ser Pro Asn
            50                  55                  60
Lys Leu Gln Ala Leu Asn Met Ala Phe Ala Ser Ser Met Ala Glu Ile
65                  70                  75                  80
Ala Ala Ser Glu Glu Gly Gly Gly Ser Leu Ser Thr Lys Thr Ser Ser
                85                  90                  95
Ile Ala Ser Ala Met Ser Asn Ala Phe Leu Gln Thr Thr Gly Val Val
                100                 105                 110
Asn Gln Pro Phe Ile Asn Glu Ile Thr Gln Leu Val Ser Met Phe Ala
            115                 120                 125
Gln Ala Gly Met Asn Asp Val Ser Ala
        130                 135

<210> SEQ ID NO 7
<211> LENGTH: 98
<212> TYPE: PRT
<213> ORGANISM: Euprosthenops australis

<400> SEQUENCE: 7

Ser Arg Leu Ser Ser Pro Ser Ala Val Ser Arg Val Ser Ser Ala Val
1               5                   10                  15
Ser Ser Leu Val Ser Asn Gly Gln Val Asn Met Ala Ala Leu Pro Asn
                20                  25                  30
Ile Ile Ser Asn Ile Ser Ser Val Ser Ala Ser Ala Pro Gly Ala
                35                  40                  45
```

-continued

```
Ser Gly Cys Glu Val Ile Val Gln Ala Leu Leu Glu Val Ile Thr Ala
 50                  55                  60

Leu Val Gln Ile Val Ser Ser Ser Val Gly Tyr Ile Asn Pro Ser
 65                  70                  75                  80

Ala Val Asn Gln Ile Thr Asn Val Val Ala Asn Ala Met Ala Gln Val
                 85                  90                  95

Met Gly

<210> SEQ ID NO 8
<211> LENGTH: 131
<212> TYPE: PRT
<213> ORGANISM: Artificial Sequence
<220> FEATURE:
<223> OTHER INFORMATION: Consensus sequence derived from spidroin NT
      fragments
<220> FEATURE:
<221> NAME/KEY: VARIANT
<222> LOCATION: (20)..(20)
<223> OTHER INFORMATION: Leu
<220> FEATURE:
<221> NAME/KEY: VARIANT
<222> LOCATION: (42)..(42)
<223> OTHER INFORMATION: Asn
<220> FEATURE:
<221> NAME/KEY: VARIANT
<222> LOCATION: (42)..(42)
<223> OTHER INFORMATION: Gln
<220> FEATURE:
<221> NAME/KEY: VARIANT
<222> LOCATION: (50)..(50)
<223> OTHER INFORMATION: Ser
<220> FEATURE:
<221> NAME/KEY: VARIANT
<222> LOCATION: (50)..(50)
<223> OTHER INFORMATION: Lys
<220> FEATURE:
<221> NAME/KEY: VARIANT
<222> LOCATION: (56)..(56)
<223> OTHER INFORMATION: Arg
<220> FEATURE:
<221> NAME/KEY: VARIANT
<222> LOCATION: (84)..(84)
<223> OTHER INFORMATION: Leu
<220> FEATURE:
<221> NAME/KEY: VARIANT
<222> LOCATION: (114)..(114)
<223> OTHER INFORMATION: Ser
<220> FEATURE:
<221> NAME/KEY: VARIANT
<222> LOCATION: (121)..(121)
<223> OTHER INFORMATION: Asn
<220> FEATURE:
<221> NAME/KEY: VARIANT
<222> LOCATION: (123)..(123)
<223> OTHER INFORMATION: Leu
<220> FEATURE:
<221> NAME/KEY: VARIANT
<222> LOCATION: (124)..(124)
<223> OTHER INFORMATION: Ser

<400> SEQUENCE: 8

Gln Ala Asn Thr Pro Trp Ser Ser Pro Asn Leu Ala Asp Ala Phe Ile
 1                   5                  10                  15

Asn Ser Phe Met Ser Ala Ala Ser Ser Ser Gly Ala Phe Ser Ala Asp
                 20                  25                  30

Gln Leu Asp Asp Met Ser Thr Ile Gly Asp Thr Leu Met Ser Ala Met
                 35                  40                  45

Asp Asn Met Gly Arg Ser Gly Lys Ser Thr Lys Ser Lys Leu Gln Ala
 50                  55                  60

Leu Asn Met Ala Phe Ala Ser Ser Met Ala Glu Ile Ala Ala Ala Glu
```

```
                65                  70                  75                  80
Ser Gly Gly Gly Ser Val Gly Val Lys Thr Asn Ala Ile Ser Asp Ala
                    85                  90                  95

Leu Ser Ser Ala Phe Tyr Gln Thr Thr Gly Ser Val Asn Pro Gln Phe
                100                 105                 110

Val Asn Glu Ile Arg Ser Leu Ile Gly Met Phe Ala Gln Ala Ser Ala
            115                 120                 125

Asn Glu Val
        130

<210> SEQ ID NO 9
<211> LENGTH: 100
<212> TYPE: PRT
<213> ORGANISM: Artificial Sequence
<220> FEATURE:
<223> OTHER INFORMATION: Consensus sequence derived from known MaSp1 and
      MaSp2 proteins
<220> FEATURE:
<221> NAME/KEY: MISC_FEATURE
<222> LOCATION: (1)..(71)
<223> OTHER INFORMATION: Sequence length present in known species
      variants
<220> FEATURE:
<221> NAME/KEY: VARIANT
<222> LOCATION: (7)..(7)
<223> OTHER INFORMATION: Glu

<400> SEQUENCE: 9

Ser Arg Leu Ser Ser Pro Gln Ala Ser Ser Arg Val Ser Ser Ala Val
1               5                   10                  15

Ser Asn Leu Val Ser Ser Gly Pro Thr Asn Ser Ala Ala Leu Ser Asn
                20                  25                  30

Thr Ile Ser Asn Val Val Ser Gln Ile Ser Ala Ser Asn Pro Gly Leu
            35                  40                  45

Ser Gly Cys Asp Val Leu Val Gln Ala Leu Leu Glu Val Val Ser Ala
        50                  55                  60

Leu Val His Ile Leu Gly Ser Ser Ser Ile Gly Gln Val Asn Tyr Gly
65                  70                  75                  80

Ser Ala Gly Gln Ala Thr Gln Ile Val Gly Gln Ser Val Ala Gln Ala
                85                  90                  95

Leu Gly Glu Phe
        100

<210> SEQ ID NO 10
<211> LENGTH: 1110
<212> TYPE: PRT
<213> ORGANISM: Euprosthenops australis
<220> FEATURE:
<221> NAME/KEY: REPEAT
<222> LOCATION: (7)..(19)
<220> FEATURE:
<221> NAME/KEY: REPEAT
<222> LOCATION: (20)..(42)
<220> FEATURE:
<221> NAME/KEY: REPEAT
<222> LOCATION: (43)..(56)
<220> FEATURE:
<221> NAME/KEY: REPEAT
<222> LOCATION: (57)..(70)
<220> FEATURE:
<221> NAME/KEY: REPEAT
<222> LOCATION: (71)..(83)
<220> FEATURE:
<221> NAME/KEY: REPEAT
<222> LOCATION: (84)..(106)
<220> FEATURE:
```

```
<221> NAME/KEY: REPEAT
<222> LOCATION: (107)..(120)
<220> FEATURE:
<221> NAME/KEY: REPEAT
<222> LOCATION: (121)..(134)
<220> FEATURE:
<221> NAME/KEY: REPEAT
<222> LOCATION: (135)..(147)
<220> FEATURE:
<221> NAME/KEY: REPEAT
<222> LOCATION: (148)..(170)
<220> FEATURE:
<221> NAME/KEY: REPEAT
<222> LOCATION: (171)..(183)
<220> FEATURE:
<221> NAME/KEY: REPEAT
<222> LOCATION: (184)..(197)
<220> FEATURE:
<221> NAME/KEY: REPEAT
<222> LOCATION: (198)..(211)
<220> FEATURE:
<221> NAME/KEY: REPEAT
<222> LOCATION: (212)..(234)
<220> FEATURE:
<221> NAME/KEY: REPEAT
<222> LOCATION: (235)..(248)
<220> FEATURE:
<221> NAME/KEY: REPEAT
<222> LOCATION: (249)..(265)
<220> FEATURE:
<221> NAME/KEY: REPEAT
<222> LOCATION: (266)..(279)
<220> FEATURE:
<221> NAME/KEY: REPEAT
<222> LOCATION: (280)..(293)
<220> FEATURE:
<221> NAME/KEY: REPEAT
<222> LOCATION: (294)..(306)
<220> FEATURE:
<221> NAME/KEY: REPEAT
<222> LOCATION: (307)..(329)
<220> FEATURE:
<221> NAME/KEY: REPEAT
<222> LOCATION: (330)..(342)
<220> FEATURE:
<221> NAME/KEY: REPEAT
<222> LOCATION: (343)..(356)
<220> FEATURE:
<221> NAME/KEY: REPEAT
<222> LOCATION: (357)..(370)
<220> FEATURE:
<221> NAME/KEY: REPEAT
<222> LOCATION: (371)..(393)
<220> FEATURE:
<221> NAME/KEY: REPEAT
<222> LOCATION: (394)..(406)
<220> FEATURE:
<221> NAME/KEY: REPEAT
<222> LOCATION: (407)..(420)
<220> FEATURE:
<221> NAME/KEY: REPEAT
<222> LOCATION: (421)..(434)
<220> FEATURE:
<221> NAME/KEY: REPEAT
<222> LOCATION: (435)..(457)
<220> FEATURE:
<221> NAME/KEY: REPEAT
<222> LOCATION: (458)..(470)
<220> FEATURE:
<221> NAME/KEY: REPEAT
<222> LOCATION: (471)..(488)
<220> FEATURE:
<221> NAME/KEY: REPEAT
<222> LOCATION: (489)..(502)
<220> FEATURE:
<221> NAME/KEY: REPEAT
<222> LOCATION: (503)..(516)
<220> FEATURE:
<221> NAME/KEY: REPEAT
```

```
-continued

<222> LOCATION: (517)..(529)
<220> FEATURE:
<221> NAME/KEY: REPEAT
<222> LOCATION: (530)..(552)
<220> FEATURE:
<221> NAME/KEY: REPEAT
<222> LOCATION: (553)..(566)
<220> FEATURE:
<221> NAME/KEY: REPEAT
<222> LOCATION: (567)..(580)
<220> FEATURE:
<221> NAME/KEY: REPEAT
<222> LOCATION: (581)..(594)
<220> FEATURE:
<221> NAME/KEY: REPEAT
<222> LOCATION: (595)..(617)
<220> FEATURE:
<221> NAME/KEY: REPEAT
<222> LOCATION: (618)..(630)
<220> FEATURE:
<221> NAME/KEY: REPEAT
<222> LOCATION: (631)..(647)
<220> FEATURE:
<221> NAME/KEY: REPEAT
<222> LOCATION: (648)..(661)
<220> FEATURE:
<221> NAME/KEY: REPEAT
<222> LOCATION: (662)..(675)
<220> FEATURE:
<221> NAME/KEY: REPEAT
<222> LOCATION: (676)..(688)
<220> FEATURE:
<221> NAME/KEY: REPEAT
<222> LOCATION: (689)..(711)
<220> FEATURE:
<221> NAME/KEY: REPEAT
<222> LOCATION: (712)..(725)
<220> FEATURE:
<221> NAME/KEY: REPEAT
<222> LOCATION: (726)..(739)
<220> FEATURE:
<221> NAME/KEY: REPEAT
<222> LOCATION: (740)..(752)
<220> FEATURE:
<221> NAME/KEY: REPEAT
<222> LOCATION: (753)..(775)
<220> FEATURE:
<221> NAME/KEY: REPEAT
<222> LOCATION: (776)..(789)
<220> FEATURE:
<221> NAME/KEY: REPEAT
<222> LOCATION: (790)..(803)
<220> FEATURE:
<221> NAME/KEY: REPEAT
<222> LOCATION: (804)..(816)
<220> FEATURE:
<221> NAME/KEY: REPEAT
<222> LOCATION: (817)..(839)
<220> FEATURE:
<221> NAME/KEY: REPEAT
<222> LOCATION: (840)..(853)
<220> FEATURE:
<221> NAME/KEY: REPEAT
<222> LOCATION: (854)..(867)
<220> FEATURE:
<221> NAME/KEY: REPEAT
<222> LOCATION: (868)..(880)
<220> FEATURE:
<221> NAME/KEY: REPEAT
<222> LOCATION: (881)..(903)
<220> FEATURE:
<221> NAME/KEY: REPEAT
<222> LOCATION: (904)..(917)
<220> FEATURE:
<221> NAME/KEY: REPEAT
<222> LOCATION: (918)..(931)
<220> FEATURE:
<221> NAME/KEY: REPEAT
<222> LOCATION: (932)..(945)
```

-continued

```
<220> FEATURE:
<221> NAME/KEY: REPEAT
<222> LOCATION: (946)..(968)
<220> FEATURE:
<221> NAME/KEY: REPEAT
<222> LOCATION: (969)..(981)
<220> FEATURE:
<221> NAME/KEY: REPEAT
<222> LOCATION: (982)..(998)
<220> FEATURE:
<221> NAME/KEY: REPEAT
<222> LOCATION: (999)..(1013)
<220> FEATURE:
<221> NAME/KEY: REPEAT
<222> LOCATION: (1014)..(1027)
<220> FEATURE:
<221> NAME/KEY: REPEAT
<222> LOCATION: (1028)..(1042)
<220> FEATURE:
<221> NAME/KEY: REPEAT
<222> LOCATION: (1043)..(1059)
<220> FEATURE:
<221> NAME/KEY: REPEAT
<222> LOCATION: (1060)..(1073)
<220> FEATURE:
<221> NAME/KEY: REPEAT
<222> LOCATION: (1074)..(1092)

<400> SEQUENCE: 10
```

Gln Gly Ala Gly Gly Asn Ala Ala Ala Ala Ala Ala Ala Ala Ala
1               5                   10                  15

Ala Ala Ala Gly Gln Gly Gly Gln Gly Gly Tyr Gly Gly Leu Gly Gln
            20                  25                  30

Gly Gly Tyr Gly Gln Gly Ala Gly Ser Ser Ala Ala Ala Ala Ala
            35                  40                  45

Ala Ala Ala Ala Ala Ala Ala Ala Gly Arg Gly Gln Gly Gly Tyr Gly
            50                  55                  60

Gln Gly Ser Gly Gly Asn Ala Ala Ala Ala Ala Ala Ala Ala Ala
65                  70                  75                  80

Ala Ala Ser Gly Gln Gly Gly Gln Gly Gly Gln Gly Gly Gln Gly Gln
            85                  90                  95

Gly Gly Tyr Gly Gln Gly Ala Gly Ser Ser Ala Ala Ala Ala Ala
            100                 105                 110

Ala Ala Ala Ala Ala Ala Ala Ala Gly Gln Gly Gln Gly Arg Tyr Gly
            115                 120                 125

Gln Gly Ala Gly Gly Asn Ala Ala Ala Ala Ala Ala Ala Ala Ala
            130                 135                 140

Ala Ala Ala Gly Gln Gly Gly Gln Gly Gly Gln Gly Gly Leu Gly Gln
145                 150                 155                 160

Gly Gly Tyr Gly Gln Gly Ala Gly Ser Ser Ala Ala Ala Ala Ala
            165                 170                 175

Ser Ala Ala Ala Ala Ala Ala Gly Arg Gly Gln Gly Gly Tyr Gly Gln
            180                 185                 190

Gly Ala Gly Gly Asn Ala Ala Ala Ala Ala Ala Ala Ala Ala
            195                 200                 205

Ala Ala Ala Gly Gln Gly Gly Gln Gly Gly Tyr Gly Gly Leu Gly Gln
            210                 215                 220

Gly Gly Tyr Gly Gln Gly Ala Gly Ser Ser Ala Ala Ala Ala Ala
225                 230                 235                 240

Ala Ala Ala Ala Ala Ala Ala Gly Gly Gln Gly Gly Gln Gly Gln Gly
            245                 250                 255

Arg Tyr Gly Gln Gly Ala Gly Ser Ser Ala Ala Ala Ala Ala Ala

```
                    260             265             270
Ala Ala Ala Ala Ala Ala Gly Gln Gly Gln Gly Gly Tyr Gly Gln
            275             280             285
Gly Ala Gly Gly Asn Ala Ala Ala Ala Ala Ala Ala Ala Ala Ala
            290             295             300
Ala Ala Gly Gln Gly Gly Gln Gly Gly Gln Gly Gly Leu Gly Gln Gly
305             310             315             320
Gly Tyr Gly Gln Gly Ala Gly Ser Ser Ala Ala Ala Ala Ala Ala
            325             330             335
Ala Ala Ala Ala Ala Ala Gly Arg Gly Gln Gly Gly Tyr Gly Gln Gly
            340             345             350
Ala Gly Gly Asn Ala Ala Ala Ala Ala Ala Ala Ala Glu Ala Ala
            355             360             365
Ala Ala Gly Gln Gly Gly Gln Gly Gly Tyr Gly Gly Leu Gly Gln Gly
            370             375             380
Gly Tyr Gly Gln Gly Ala Gly Ser Ser Ala Ala Ala Ala Ala Ala
385             390             395             400
Ala Ala Ala Ala Ala Ala Gly Arg Gly Gln Gly Gly Tyr Gly Gln Gly
            405             410             415
Ala Gly Gly Asn Ala Ala Ala Ala Ala Ala Ala Ala Ala Ala Ala
            420             425             430
Ala Ala Gly Gln Gly Gly Gln Gly Gly Tyr Gly Gly Leu Gly Gln Gly
            435             440             445
Gly Tyr Gly Gln Gly Ala Gly Ser Ser Ala Ala Ala Ala Ala Ala
450             455             460
Ala Ala Ala Ala Ala Ala Gly Gly Gln Gly Gly Gln Gly Gly Arg
465             470             475             480
Tyr Gly Gln Gly Ala Gly Ser Ser Ala Ala Ala Ala Ala Ala Ala
            485             490             495
Ala Ala Ala Ala Ala Ala Gly Arg Gly Gln Gly Gly Tyr Gly Gln Gly
            500             505             510
Ser Gly Gly Asn Ala Ala Ala Ala Ala Ala Ala Ala Ala Ala Ala
            515             520             525
Ser Gly Gln Gly Ser Gln Gly Gly Gln Gly Gly Gln Gly Gly
            530             535             540
Tyr Gly Gln Gly Ala Gly Ser Ser Ala Ala Ala Ala Ala Ala Ala
545             550             555             560
Ala Ala Ala Ala Ala Ser Gly Arg Gly Gln Gly Gly Tyr Gly Gln Gly
            565             570             575
Ala Gly Gly Asn Ala Ala Ala Ala Ala Ala Ala Ala Ala Ala Ala
            580             585             590
Ala Ala Gly Gln Gly Gly Gln Gly Gly Tyr Gly Gly Leu Gly Gln Gly
            595             600             605
Gly Tyr Gly Gln Gly Ala Gly Ser Ser Ala Ala Ala Ala Ala Ala
            610             615             620
Ala Ala Ala Ala Ala Gly Gly Gln Gly Gly Gln Gly Gln Gly Gly Tyr
625             630             635             640
Gly Gln Gly Ala Gly Ser Ser Ala Ala Ala Ala Ala Ala Ala Ala
            645             650             655
Ala Ala Ala Ala Ala Gly Arg Gly Gln Gly Gly Tyr Gly Gln Gly Ser
            660             665             670
Gly Gly Asn Ala Ala Ala Ala Ala Ala Ala Ala Ala Ala Ala Ser
            675             680             685
```

Gly Gln Gly Gly Gln Gly Gly Gln Gly Gly Gln Gly Gly Tyr
        690                 695                 700

Gly Gln Gly Ala Gly Ser Ser Ala Ala Ala Ala Ala Ala Ala Ala
705                 710                 715                 720

Ala Ala Ala Ala Ala Gly Gln Gly Gln Gly Gly Tyr Gly Gln Gly Ala
                725                 730                 735

Gly Gly Asn Ala Ala Ala Ala Ala Ala Ala Ala Ala Ala Ala
            740                 745                 750

Gly Gln Gly Gly Gln Gly Gly Gln Gly Gly Leu Gly Gln Gly Gly Tyr
            755                 760                 765

Gly Gln Gly Ala Gly Ser Ser Ala Ala Ala Ala Ala Ala Ala Ala
        770                 775                 780

Ala Ala Ala Ala Ala Gly Arg Gly Gln Gly Gly Tyr Gly Gln Gly Val
785                 790                 795                 800

Gly Gly Asn Ala Ala Ala Ala Ala Ala Ala Ala Ala Ala Ala
            805                 810                 815

Gly Gln Gly Gly Gln Gly Gly Gln Gly Gly Leu Gly Gln Gly Gly Tyr
            820                 825                 830

Gly Gln Gly Ala Gly Ser Ser Ala Ala Ala Ala Ala Ala Ala Ala
        835                 840                 845

Ala Ala Ala Ala Ala Gly Arg Gly Gln Gly Gly Tyr Gly Gln Gly Ser
850                 855                 860

Gly Gly Asn Ala Ala Ala Ala Ala Ala Ala Ala Ala Ala Ser
865                 870                 875                 880

Gly Gln Gly Ser Gln Gly Gly Gln Gly Gly Gln Gly Gly Tyr
            885                 890                 895

Gly Gln Gly Ala Gly Ser Ser Ala Ala Ala Ala Ala Ala Ala Ala
            900                 905                 910

Ala Ala Ala Ala Ser Gly Arg Gly Gln Gly Gly Tyr Gly Gln Gly Ala
        915                 920                 925

Gly Gly Asn Ala Ala Ala Ala Ala Ala Ala Ala Ala Ala Ala
        930                 935                 940

Ala Gly Gln Gly Gly Gln Gly Gly Tyr Gly Gly Leu Gly Gln Gly Gly
945                 950                 955                 960

Tyr Gly Gln Gly Ala Gly Ser Ser Ala Ala Ala Ala Ala Ala Ala
                965                 970                 975

Ala Ala Ala Ala Gly Gly Gln Gly Gly Gln Gly Gln Gly Gly Tyr Gly
            980                 985                 990

Gln Gly Ser Gly Gly Ser Ala Ala Ala Ala Ala Ala Ala Ala Ala
        995                 1000                1005

Ala Ala Ala Ala Ala Gly Arg Gly Gln Gly Gly Tyr Gly Gln Gly
    1010                1015                1020

Ser Gly Gly Asn Ala Ala Ala Ala Ala Ala Ala Ala Ala Ala
    1025                1030                1035

Ala Ala Ala Ala Gly Gln Gly Gly Gln Gly Gly Tyr Gly Arg Gln
    1040                1045                1050

Ser Gln Gly Ala Gly Ser Ala Ala Ala Ala Ala Ala Ala Ala
    1055                1060                1065

Ala Ala Ala Ala Ala Gly Ser Gly Gln Gly Gly Tyr Gly Gly Gln
    1070                1075                1080

Gly Gln Gly Gly Tyr Gly Gln Ser Ser Ala Ser Ala Ser Ala Ala
    1085                1090                1095

-continued

Ala Ser Ala Ala Ser Thr Val Ala Asn Ser Val Ser
         1100            1105            1110

<210> SEQ ID NO 11
<211> LENGTH: 23
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (4)..(4)
<223> OTHER INFORMATION: Ser
<220> FEATURE:
<221> NAME/KEY: VARIANT
<222> LOCATION: (8)..(8)
<223> OTHER INFORMATION: Tyr
<220> FEATURE:
<221> NAME/KEY: VARIANT
<222> LOCATION: (11)..(11)
<223> OTHER INFORMATION: Gln

<400> SEQUENCE: 11

Gly Gln Gly Gly Gln Gly Gly Gln Gly Gly Leu Gly Gln Gly Gly Tyr
1               5                   10                  15

Gly Gln Gly Ala Gly Ser Ser
            20

<210> SEQ ID NO 12
<211> LENGTH: 17
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (9)..(9)
<223> OTHER INFORMATION: Arg
<220> FEATURE:
<221> NAME/KEY: VARIANT
<222> LOCATION: (14)..(14)
<223> OTHER INFORMATION: Ser
<220> FEATURE:
<221> NAME/KEY: VARIANT
<222> LOCATION: (16)..(16)
<223> OTHER INFORMATION: Gly

<400> SEQUENCE: 12

Gly Gln Gly Gly Gln Gly Gln Gly Gly Tyr Gly Gln Gly Ala Gly Ser
1               5                   10                  15

Ser

<210> SEQ ID NO 13
<211> LENGTH: 14
<212> TYPE: PRT
<213> ORGANISM: Artificial Sequence
<220> FEATURE:
<223> OTHER INFORMATION: Consensus sequence derived from internal
      repeats of Euprosthenops australis MaSp1
<220> FEATURE:
<221> NAME/KEY: VARIANT
<222> LOCATION: (2)..(2)
<223> OTHER INFORMATION: Gln
<220> FEATURE:
<221> NAME/KEY: VARIANT
<222> LOCATION: (6)..(6)
<223> OTHER INFORMATION: Arg
<220> FEATURE:
<221> NAME/KEY: VARIANT
<222> LOCATION: (11)..(11)

<223> OTHER INFORMATION: Ser
<220> FEATURE:
<221> NAME/KEY: VARIANT
<222> LOCATION: (11)..(11)
<223> OTHER INFORMATION: Val

<400> SEQUENCE: 13

Gly Arg Gly Gln Gly Gly Tyr Gly Gln Gly Ala Gly Gly Asn
1               5                   10

<210> SEQ ID NO 14
<211> LENGTH: 888
<212> TYPE: DNA
<213> ORGANISM: Euprosthenops australis

<400> SEQUENCE: 14

```
ggttctggga attcacacac tacaccatgg acaaacccag gactcgcaga aaacttcatg      60
aacagtttca tgcaaggcct gagctcgatg ccaggtttca cggcaagcca attggatgat    120
atgtcaacca tcgcacaatc catggtacag tcaatacaat ccttggcggc acaaggcagg    180
acatcaccga ataagctgca ggcccttaac atggcttttg catcttcgat ggcagaaatc    240
gcggcatccg aagaaggagg gggaagcctt tccaccaaaa ctagctctat agccagtgca    300
atgtccaacg cgtttctgca aacaactgga gtggtaaacc aaccgttcat aaatgaaata    360
actcagctcg ttagcatgtt tgctcaagca ggtatgaatg atgtcagtgc ttccgcatca    420
gcaggagcat ccgcagcagc atccgcagga gcggctagcg gtcaaggtgg atatggtgga    480
ctaggtcaag gaggatatgg acaaggtgca ggaagttctg cagccgctgc cgccgccgca    540
gcagccgccg cagcaggtgg acaaggtgga caaggtcaag gaggatatgg acaaggttca    600
ggaggttctg cagccgccgc cgccgccgca gcagcagcag cagctgcagc agctggacga    660
ggtcaaggag gatatggtca aggttctgga ggtaatgctg ctgccgcagc cgctgccgcc    720
gccgccgccg ctgcagcagc cggacaggga ggtcaaggtg gatatggtag acaaagccaa    780
ggtgctggtt ccgctgctgc tgctgctgct gctgctgccg ctgctgctgc tgcaggatct    840
ggacaaggtg gatacggtgg acaaggtcaa ggaggttatg gtcagagt               888
```

<210> SEQ ID NO 15
<211> LENGTH: 1272
<212> TYPE: DNA
<213> ORGANISM: Euprosthenops australis

<400> SEQUENCE: 15

```
atgaaagcat cacacactac accatggaca aacccaggac tcgcagaaaa cttcatgaac      60
agtttcatgc aaggcctgag ctcgatgcca ggtttcacgg caagccaatt ggatgatatg    120
tcaaccatcg cacaatccat ggtacagtca atacaatcct ggcggcaca aggcaggaca    180
tcaccgaata agctgcaggc ccttaacatg gcttttgcat cttcgatggc agaaatcgcg    240
gcatccgaag aaggaggggg aagcctttcc accaaaacta gctctatagc cagtgcaatg    300
tccaacgcgt ttctgcaaac aactggagtg gtaaaccaac cgttcataaa tgaaataact    360
cagctcgtta gcatgtttgc tcaagcaggt atgaatgatg tcagtgcttc cgcatcagca    420
ggagcatccg cagcagcatc cgcaggagcg ctagcggtc aaggtggata tggtggacta    480
ggtcaaggag gatatggaca aggtgcagga agttctgcag ccgctgccgc cgccgcagca    540
gccgccgcag caggtggaca aggtggacaa ggtcaaggag gatatggaca aggttcagga    600
ggttctgcag ccgccgccgc cgccgcagca gcagcagcag ctgcagcagc tggacgaggt    660
```

| | |
|---|---|
| caaggaggat atggtcaagg ttctggaggt aatgctgctg ccgcagccgc tgccgccgcc | 720 |
| gccgccgctg cagcagccgg acagggaggt caaggtggat atggtagaca aagccaaggt | 780 |
| gctggttccg ctgctgctgc tgctgctgct gctgccgctg ctgctgctgc aggatctgga | 840 |
| caaggtggat acggtggaca aggtcaagga ggttatggtc agagtagtgc ttctgcttca | 900 |
| gctgctgcgt cagctgctag tactgtagct aattcggtga gtcgcctctc atcgccttcc | 960 |
| gcagtatctc gagtttcttc agcagtttct agcttggttt caaatggtca agtgaatatg | 1020 |
| gcagcgttac ctaatatcat ttccaacatt tcttcttctg tcagtgcatc tgctcctggt | 1080 |
| gcttctggat gtgaggtcat agtgcaagct ctactcgaag tcatcactgc tcttgttcaa | 1140 |
| atcgttagtt cttctagtgt tggatatatt aatccatctg ctgtgaacca aattactaat | 1200 |
| gttgttgcta atgccatggc tcaagtaatg ggcaagcttg cggccgcact cgagcaccac | 1260 |
| caccaccacc ac | 1272 |

<210> SEQ ID NO 16
<211> LENGTH: 1020
<212> TYPE: DNA
<213> ORGANISM: Euprosthenops australis

<400> SEQUENCE: 16

| | |
|---|---|
| ggttctggga attcacacac tacaccatgg acaaacccag gactcgcaga aaacttcatg | 60 |
| aacagtttca tgcaaggcct gagctcgatg ccaggtttca cggcaagcca attggatgat | 120 |
| atgtcaacca tcgcacaatc catggtacag tcaatacaat ccttggcggc acaaggcagg | 180 |
| acatcaccga ataagctgca ggcccttaac atggcttttg catcttcgat ggcagaaatc | 240 |
| gcggcatccg aagaaggagg gggaagccrt tccaccaaaa ctagctctat agccagtgca | 300 |
| atgtccaacg cgtttctgca aacaactgga gtggtaaacc aaccgttcat aaatgaaata | 360 |
| actcagctcg ttagcatgtt tgctcaagca ggtatgaatg atgtcagtgc ttccgcatca | 420 |
| gcaggagcat ccgcagcagc atccgcagga gcgccaggtt acagtcctgc accaagctac | 480 |
| agttcgggag gttatgcttc aagtgctgcc tcagcagccg ctgcagcagg acaaggagga | 540 |
| cctgggggat acggtccagc acctaaccaa ggagcttcat ctgccgctgc tgcagccgca | 600 |
| ggatcaggac aaggaccatc aggaccgtac ggtacatctt accagataag tacacaatat | 660 |
| actcaaacaa cgacttcaca gggacaagga tatgggtcaa gtagcgctgg agccgcagct | 720 |
| gcaggcgctg caggtgctgg acaaggggc tacggaggtc aaggtcaagg aggatatggt | 780 |
| caaggagccg gaggtgctgc cgcagcagcc gccgctgccg cagccgctgc cgccgcagcc | 840 |
| ggacaaggtg gacaaggtgg aggaggatat ggacaaggag gacaaggagg acaaggagga | 900 |
| caaggtcaag gaggatatgg acaaggtgca ggaagttctg cagccgccgc cgccgcagca | 960 |
| gcagcagccg ccgcagcagc aggacgaggt caaggaggat atggtccagg ttctggaggt | 1020 |

<210> SEQ ID NO 17
<211> LENGTH: 422
<212> TYPE: PRT
<213> ORGANISM: Euprosthenops australis

<400> SEQUENCE: 17

Met Lys Ala Ser His Thr Thr Pro Trp Thr Asn Pro Gly Leu Ala Glu
1               5                   10                  15

Asn Phe Met Asn Ser Phe Met Gln Gly Leu Ser Ser Met Pro Gly Phe
            20                  25                  30

Thr Ala Ser Gln Leu Asp Asp Met Ser Thr Ile Ala Gln Ser Met Val

-continued

```
                     35                  40                  45
Gln Ser Ile Gln Ser Leu Ala Ala Gln Gly Arg Thr Ser Pro Asn Lys
 50                  55                  60

Leu Gln Ala Leu Asn Met Ala Phe Ala Ser Ser Met Ala Glu Ile Ala
 65                  70                  75                  80

Ala Ser Glu Glu Gly Gly Ser Leu Ser Thr Lys Thr Ser Ser Ile
                 85                  90                  95

Ala Ser Ala Met Ser Asn Ala Phe Leu Gln Thr Thr Gly Val Val Asn
                100                 105                 110

Gln Pro Phe Ile Asn Glu Ile Thr Gln Leu Val Ser Met Phe Ala Gln
                115                 120                 125

Ala Gly Met Asn Asp Val Ser Ala Ser Ala Ser Ala Gly Ala Ser Ala
                130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala Ala
                165                 170                 175

Ala Ala Ala Ala Ala Ala Ala Gly Gly Gln Gly Gly Gln Gly Gln
                180                 185                 190

Gly Gly Tyr Gly Gln Gly Ser Gly Gly Ser Ala Ala Ala Ala Ala Ala
                195                 200                 205

Ala Ala Ala Ala Ala Ala Ala Ala Gly Arg Gly Gln Gly Gly Tyr
210                 215                 220

Gly Gln Gly Ser Gly Gly Asn Ala Ala Ala Ala Ala Ala Ala Ala
225                 230                 235                 240

Ala Ala Ala Ala Ala Ala Gly Gln Gly Gly Gln Gly Tyr Gly Arg
                245                 250                 255

Gln Ser Gln Gly Ala Gly Ser Ala Ala Ala Ala Ala Ala Ala Ala
                260                 265                 270

Ala Ala Ala Ala Ala Gly Ser Gly Gln Gly Gly Tyr Gly Gly Gln Gly
                275                 280                 285

Gln Gly Gly Tyr Gly Gln Ser Ser Ala Ser Ala Ser Ala Ala Ala Ser
                290                 295                 300

Ala Ala Ser Thr Val Ala Asn Ser Val Ser Arg Leu Ser Ser Pro Ser
305                 310                 315                 320

Ala Val Ser Arg Val Ser Ser Ala Val Ser Ser Leu Val Ser Asn Gly
                325                 330                 335

Gln Val Asn Met Ala Ala Leu Pro Asn Ile Ile Ser Asn Ile Ser Ser
                340                 345                 350

Ser Val Ser Ala Ser Ala Pro Gly Ala Ser Gly Cys Glu Val Ile Val
                355                 360                 365

Gln Ala Leu Leu Glu Val Ile Thr Ala Leu Val Gln Ile Val Ser Ser
                370                 375                 380

Ser Ser Val Gly Tyr Ile Asn Pro Ser Ala Val Asn Gln Ile Thr Asn
385                 390                 395                 400

Val Val Ala Asn Ala Met Ala Gln Val Met Gly Ala Ala Ala Leu Glu
                405                 410                 415

His His His His His His
                420
```

<210> SEQ ID NO 18
<211> LENGTH: 1266
<212> TYPE: DNA
<213> ORGANISM: Euprosthenops australis -continued

<400> SEQUENCE: 18

```
atgaaagcat cacacactac accatggaca aacccaggac tcgcagaaaa cttcatgaac      60
agtttcatgc aaggcctgag ctcgatgcca ggtttcacgg caagccaatt ggatgatatg     120
tcaaccatcg cacaatccat ggtacagtca atacaatcct ggcggcaca aggcaggaca      180
tcaccgaata agctgcaggc ccttaacatg gcttttgcat cttcgatggc agaaatcgcg     240
gcatccgaag aaggaggggg aagcctttcc accaaaacta gctctatagc cagtgcaatg     300
tccaacgcgt ttctgcaaac aactggagtg gtaaaccaac cgttcataaa tgaaataact     360
cagctcgtta gcatgtttgc tcaagcaggt atgaatgatg tcagtgcttc cgcatcagca     420
ggagcatccg cagcagcatc cgcaggagcg gctagcggtc aaggtggata tggtggacta     480
ggtcaaggag atatggaca aggtgcagga agttctgcag ccgctgccgc cgccgcagca      540
gccgccgcag caggtggaca aggtggacaa ggtcaaggag atatggaca aggttcagga      600
ggttctgcag ccgccgccgc cgccgcagca gcagcagcag ctgcagcagc tggacgaggt     660
caaggaggat atggtcaagg ttctggaggt aatgctgctg ccgcagccgc tgccgccgcc     720
gccgccgctg cagcagccgg acagggaggt caaggtggat atggtagaca aagccaaggt     780
gctggttccg ctgctgctgc tgctgctgct gctgccgctg ctgctgctgc aggatctgga     840
caaggtggat acggtggaca aggtcaagga ggttatggtc agagtagtgc ttctgcttca     900
gctgctgcgt cagctgctag tactgtagct aattcggtga gtcgcctctc atcgccttcc     960
gcagtatctc gagtttcttc agcagtttct agcttggttt caaatggtca agtgaatatg    1020
gcagcgttac ctaatatcat ttccaacatt tcttcttctg tcagtgcatc tgctcctggt    1080
gcttctggat gtgaggtcat agtgcaagct ctactcgaag tcatcactgc tcttgttcaa    1140
atcgttagtt cttctagtgt tggatatatt aatccatctg ctgtgaacca aattactaat    1200
gttgttgcta atgccatggc tcaagtaatg ggcgcggccg cactcgagca ccaccaccac    1260
caccac                                                              1266
```

<210> SEQ ID NO 19
<211> LENGTH: 491
<212> TYPE: PRT
<213> ORGANISM: Euprosthenops australis

<400> SEQUENCE: 19

```
Met Ala Ser Met Thr Gly Gly Gln Gln Met Gly Arg Gly Ser Val Asp
1               5                   10                  15

Asn Lys Phe Asn Lys Glu Arg Arg Ala Arg Arg Glu Ile Arg His
            20                  25                  30

Leu Pro Asn Leu Asn Arg Glu Gln Arg Arg Ala Phe Ile Arg Ser Leu
        35                  40                  45

Arg Asp Asp Pro Ser Gln Ser Ala Asn Leu Leu Ala Glu Ala Lys Lys
    50                  55                  60

Leu Asn Asp Ala Gln Ala Pro Lys Pro Asn Leu Glu Ala Leu Phe Gln
65                  70                  75                  80

Gly Pro Asn Ser His Thr Thr Pro Trp Thr Asn Pro Gly Leu Ala Glu
                85                  90                  95

Asn Phe Met Asn Ser Phe Met Gln Gly Leu Ser Ser Met Pro Gly Phe
            100                 105                 110

Thr Ala Ser Gln Leu Asp Asp Met Ser Thr Ile Ala Gln Ser Met Val
        115                 120                 125
```

```
Gln Ser Ile Gln Ser Leu Ala Ala Gln Gly Arg Thr Ser Pro Asn Lys
    130                 135                 140

Leu Gln Ala Leu Asn Met Ala Phe Ala Ser Ser Met Ala Glu Ile Ala
145                 150                 155                 160

Ala Ser Glu Glu Gly Gly Ser Leu Ser Thr Lys Thr Ser Ser Ile
                165                 170                 175

Ala Ser Ala Met Ser Asn Ala Phe Leu Gln Thr Thr Gly Val Val Asn
                180                 185                 190

Gln Pro Phe Ile Asn Glu Ile Thr Gln Leu Val Ser Met Phe Ala Gln
            195                 200                 205

Ala Gly Met Asn Asp Val Ser Ala Ser Ala Ser Ala Gly Ala Ser Ala
        210                 215                 220

Ala Ala Ser Ala Gly Ala Ala Ser Gly Gln Gly Gly Tyr Gly Gly Leu
225                 230                 235                 240

Gly Gln Gly Gly Tyr Gly Gln Gly Ala Gly Ser Ser Ala Ala Ala Ala
                245                 250                 255

Ala Ala Ala Ala Ala Ala Ala Gly Gly Gln Gly Gly Gln Gly Gln
            260                 265                 270

Gly Gly Tyr Gly Gln Gly Ser Gly Gly Ser Ala Ala Ala Ala Ala
        275                 280                 285

Ala Ala Ala Ala Ala Ala Ala Gly Arg Gly Gln Gly Gly Tyr
        290                 295                 300

Gly Gln Gly Ser Gly Gly Asn Ala Ala Ala Ala Ala Ala Ala Ala
305                 310                 315                 320

Ala Ala Ala Ala Ala Ala Gly Gln Gly Gln Gly Gly Tyr Gly Arg
                325                 330                 335

Gln Ser Gln Gly Ala Gly Ser Ala Ala Ala Ala Ala Ala Ala Ala
            340                 345                 350

Ala Ala Ala Ala Ala Gly Ser Gly Gln Gly Gly Tyr Gly Gly Gln Gly
            355                 360                 365

Gln Gly Gly Tyr Gly Gln Ser Ser Ala Ser Ala Ser Ala Ala Ala Ser
        370                 375                 380

Ala Ala Ser Thr Val Ala Asn Ser Val Ser Arg Leu Ser Ser Pro Ser
385                 390                 395                 400

Ala Val Ser Arg Val Ser Ser Ala Val Ser Ser Leu Val Ser Asn Gly
                405                 410                 415

Gln Val Asn Met Ala Ala Leu Pro Asn Ile Ile Ser Asn Ile Ser Ser
            420                 425                 430

Ser Val Ser Ala Ser Ala Pro Gly Ala Ser Gly Cys Glu Val Ile Val
        435                 440                 445

Gln Ala Leu Leu Glu Val Ile Thr Ala Leu Val Gln Ile Val Ser Ser
    450                 455                 460

Ser Ser Val Gly Tyr Ile Asn Pro Ser Ala Val Asn Gln Ile Thr Asn
465                 470                 475                 480

Val Val Ala Asn Ala Met Ala Gln Val Met Gly
                485                 490

<210> SEQ ID NO 20
<211> LENGTH: 411
<212> TYPE: PRT
<213> ORGANISM: Euprosthenops australis

<400> SEQUENCE: 20

Gly Pro Asn Ser His Thr Thr Pro Trp Thr Asn Pro Gly Leu Ala Glu
1               5                   10                  15
```

```
Asn Phe Met Asn Ser Phe Met Gln Gly Leu Ser Ser Met Pro Gly Phe
             20                  25                  30

Thr Ala Ser Gln Leu Asp Asp Met Ser Thr Ile Ala Gln Ser Met Val
         35                  40                  45

Gln Ser Ile Gln Ser Leu Ala Ala Gln Gly Arg Thr Ser Pro Asn Lys
 50                  55                  60

Leu Gln Ala Leu Asn Met Ala Phe Ala Ser Ser Met Ala Glu Ile Ala
 65                  70                  75                  80

Ala Ser Glu Glu Gly Gly Ser Leu Ser Thr Lys Thr Ser Ser Ile
                 85                  90                  95

Ala Ser Ala Met Ser Asn Ala Phe Leu Gln Thr Thr Gly Val Val Asn
            100                 105                 110

Gln Pro Phe Ile Asn Glu Ile Thr Gln Leu Val Ser Met Phe Ala Gln
            115                 120                 125

Ala Gly Met Asn Asp Val Ser Ala Ser Ala Gly Ala Ser Ala
130                 135                 140

Ala Ala Ser Ala Gly Ala Ala Ser Gly Gln Gly Gly Tyr Gly Gly Leu
145                 150                 155                 160

Gly Gln Gly Gly Tyr Gly Gln Gly Ala Gly Ser Ser Ala Ala Ala Ala
                165                 170                 175

Ala Ala Ala Ala Ala Ala Ala Gly Gly Gln Gly Gly Gln Gly Gln
            180                 185                 190

Gly Gly Tyr Gly Gln Gly Ser Gly Gly Ser Ala Ala Ala Ala Ala
            195                 200                 205

Ala Ala Ala Ala Ala Ala Ala Gly Arg Gly Gln Gly Gly Tyr
210                 215                 220

Gly Gln Gly Ser Gly Gly Asn Ala Ala Ala Ala Ala Ala Ala Ala
225                 230                 235                 240

Ala Ala Ala Ala Ala Ala Gly Gln Gly Gly Gln Gly Gly Tyr Gly Arg
            245                 250                 255

Gln Ser Gln Gly Ala Gly Ser Ala Ala Ala Ala Ala Ala Ala
            260                 265                 270

Ala Ala Ala Ala Ala Gly Ser Gly Gln Gly Gly Tyr Gly Gly Gln Gly
            275                 280                 285

Gln Gly Gly Tyr Gly Gln Ser Ala Ser Ala Ser Ala Ala Ala Ser
            290                 295                 300

Ala Ala Ser Thr Val Ala Asn Ser Val Ser Arg Leu Ser Ser Pro Ser
305                 310                 315                 320

Ala Val Ser Arg Val Ser Ser Ala Val Ser Ser Leu Val Ser Asn Gly
                325                 330                 335

Gln Val Asn Met Ala Ala Leu Pro Asn Ile Ile Ser Asn Ile Ser Ser
            340                 345                 350

Ser Val Ser Ala Ser Ala Pro Gly Ala Ser Gly Cys Glu Val Ile Val
            355                 360                 365

Gln Ala Leu Leu Glu Val Ile Thr Ala Leu Val Gln Ile Val Ser Ser
            370                 375                 380

Ser Ser Val Gly Tyr Ile Asn Pro Ser Ala Val Asn Gln Ile Thr Asn
385                 390                 395                 400

Val Val Ala Asn Ala Met Ala Gln Val Met Gly
            405                 410

<210> SEQ ID NO 21
<211> LENGTH: 551
```

<212> TYPE: PRT
<213> ORGANISM: Euprosthenops australis

<400> SEQUENCE: 21

```
Met Gly His His His His His His Met Ala Ser Ser Asp Lys Ile Ile
1               5                   10                  15

His Leu Thr Asp Asp Ser Phe Asp Thr Asp Val Leu Lys Ala Asp Gly
            20                  25                  30

Ala Ile Leu Val Asp Phe Trp Ala Glu Trp Cys Gly Pro Cys Lys Met
        35                  40                  45

Ile Ala Pro Ile Leu Asp Glu Ile Ala Asp Glu Tyr Gln Gly Lys Leu
    50                  55                  60

Thr Val Ala Lys Leu Asn Ile Asp Gln Asn Pro Gly Thr Ala Pro Lys
65              70                  75                  80

Tyr Gly Ile Arg Gly Ile Pro Thr Leu Leu Leu Phe Lys Asn Gly Glu
                85                  90                  95

Val Ala Ala Thr Lys Val Gly Ala Leu Ser Lys Gly Gln Leu Lys Glu
            100                 105                 110

Phe Leu Asp Ala Asn Leu Ala Gly Ser Gly Ser Gly His Met His His
        115                 120                 125

His His His Ser Ser Gly Leu Val Pro Arg Gly Ser Gly Asn Ser
    130                 135                 140

His Thr Thr Pro Trp Thr Asn Pro Gly Leu Ala Glu Asn Phe Met Asn
145             150                 155                 160

Ser Phe Met Gln Gly Leu Ser Ser Met Pro Gly Phe Thr Ala Ser Gln
                165                 170                 175

Leu Asp Asp Met Ser Thr Ile Ala Gln Ser Met Val Gln Ser Ile Gln
            180                 185                 190

Ser Leu Ala Ala Gln Gly Arg Thr Ser Pro Asn Lys Leu Gln Ala Leu
        195                 200                 205

Asn Met Ala Phe Ala Ser Ser Met Ala Glu Ile Ala Ala Ser Glu Glu
    210                 215                 220

Gly Gly Gly Ser Leu Ser Thr Lys Thr Ser Ser Ile Ala Ser Ala Met
225             230                 235                 240

Ser Asn Ala Phe Leu Gln Thr Thr Gly Val Val Asn Gln Pro Phe Ile
                245                 250                 255

Asn Glu Ile Thr Gln Leu Val Ser Met Phe Ala Gln Ala Gly Met Asn
            260                 265                 270

Asp Val Ser Ala Ser Ala Ser Ala Gly Ala Ser Ala Ala Ala Ser Ala
        275                 280                 285

Gly Ala Ala Ser Gly Gln Gly Gly Tyr Gly Gly Leu Gly Gln Gly Gly
    290                 295                 300

Tyr Gly Gln Gly Ala Gly Ser Ser Ala Ala Ala Ala Ala Ala Ala Ala
305                 310                 315                 320

Ala Ala Ala Ala Gly Gly Gln Gly Gly Gln Gly Gln Gly Gly Tyr Gly
                325                 330                 335

Gln Gly Ser Gly Gly Ser Ala Ala Ala Ala Ala Ala Ala Ala Ala Ala
            340                 345                 350

Ala Ala Ala Ala Ala Gly Arg Gly Gln Gly Gly Tyr Gly Gln Gly Ser
        355                 360                 365

Gly Gly Asn Ala Ala Ala Ala Ala Ala Ala Ala Ala Ala Ala Ala Ala
    370                 375                 380

Ala Ala Gly Gln Gly Gly Gln Gly Gly Tyr Gly Arg Gln Ser Gln Gly
385                 390                 395                 400
```

```
Ala Gly Ser Ala Ala Ala Ala Ala Ala Ala Ala Ala Ala
            405                 410                 415

Ala Gly Ser Gly Gln Gly Gly Tyr Gly Gly Gln Gly Gly Tyr
            420                 425                 430

Gly Gln Ser Ser Ala Ser Ala Ser Ala Ala Ser Ala Ala Ser Thr
            435                 440                 445

Val Ala Asn Ser Val Ser Arg Leu Ser Ser Pro Ser Ala Val Ser Arg
450                 455                 460

Val Ser Ser Ala Val Ser Ser Leu Val Ser Asn Gly Gln Val Asn Met
465                 470                 475                 480

Ala Ala Leu Pro Asn Ile Ile Ser Asn Ile Ser Ser Val Ser Ala
                485                 490                 495

Ser Ala Pro Gly Ala Ser Gly Cys Glu Val Ile Val Gln Ala Leu Leu
                500                 505                 510

Glu Val Ile Thr Ala Leu Val Gln Ile Val Ser Ser Ser Val Gly
                515                 520                 525

Tyr Ile Asn Pro Ser Ala Val Asn Gln Ile Thr Asn Val Val Ala Asn
            530                 535                 540

Ala Met Ala Gln Val Met Gly
545                 550

<210> SEQ ID NO 22
<211> LENGTH: 412
<212> TYPE: PRT
<213> ORGANISM: Euprosthenops australis

<400> SEQUENCE: 22

Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
                20                  25                  30

Phe Thr Ala Ser Gln Leu Asp Asp Met Ser Thr Ile Ala Gln Ser Met
            35                  40                  45

Val Gln Ser Ile Gln Ser Leu Ala Ala Gln Gly Arg Thr Ser Pro Asn
50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
                100                 105                 110

Asn Gln Pro Phe Ile Asn Glu Ile Thr Gln Leu Val Ser Met Phe Ala
            115                 120                 125

Gln Ala Gly Met Asn Asp Val Ser Ala Ser Ala Ser Ala Gly Ala Ser
            130                 135                 140

Ala Ala Ala Ser Ala Gly Ala Ser Gly Gln Gly Gly Tyr Gly Gly
145                 150                 155                 160

Leu Gly Gln Gly Gly Tyr Gly Gln Gly Ala Gly Ser Ser Ala Ala Ala
                165                 170                 175

Ala Ala Ala Ala Ala Ala Ala Gly Gly Gln Gly Gly Gln Gly
            180                 185                 190

Gln Gly Gly Tyr Gly Gln Gly Ser Gly Ser Ala Ala Ala Ala
            195                 200                 205

Ala Ala Ala Ala Ala Ala Ala Ala Ala Ala Gly Arg Gly Gln Gly Gly
```

```
            210                 215                 220
Tyr Gly Gln Gly Ser Gly Gly Asn Ala Ala Ala Ala Ala Ala Ala
225                 230                 235                 240

Ala Ala Ala Ala Ala Ala Gly Gln Gly Gly Gln Gly Gly Tyr Gly
                245                 250                 255

Arg Gln Ser Gln Gly Ala Gly Ser Ala Ala Ala Ala Ala Ala Ala
                260                 265                 270

Ala Ala Ala Ala Ala Gly Ser Gly Gln Gly Gly Tyr Gly Gly Gln
            275                 280                 285

Gly Gln Gly Gly Tyr Gly Gln Ser Ser Ala Ser Ala Ser Ala Ala
            290                 295                 300

Ser Ala Ala Ser Thr Val Ala Asn Ser Val Ser Arg Leu Ser Ser Pro
305                 310                 315                 320

Ser Ala Val Ser Arg Val Ser Ser Ala Val Ser Ser Leu Val Ser Asn
                325                 330                 335

Gly Gln Val Asn Met Ala Ala Leu Pro Asn Ile Ile Ser Asn Ile Ser
                340                 345                 350

Ser Ser Val Ser Ala Ser Ala Pro Gly Ala Ser Gly Cys Glu Val Ile
            355                 360                 365

Val Gln Ala Leu Leu Glu Val Ile Thr Ala Leu Val Gln Ile Val Ser
370                 375                 380

Ser Ser Ser Val Gly Tyr Ile Asn Pro Ser Ala Val Asn Gln Ile Thr
385                 390                 395                 400

Asn Val Val Ala Asn Ala Met Ala Gln Val Met Gly
                405                 410

<210> SEQ ID NO 23
<211> LENGTH: 534
<212> TYPE: PRT
<213> ORGANISM: Euprosthenops australis

<400> SEQUENCE: 23

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
                20                  25                  30

Ser Ser Met Pro Gly Phe Thr Ala Ser Gln Leu Asp Asp Met Ser Thr
            35                  40                  45

Ile Ala Gln Ser Met Val Gln Ser Ile Gln Ser Leu Ala Ala Gln Gly
        50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
                100                 105                 110

Thr Thr Gly Val Val Asn Gln Pro Phe Ile Asn Glu Ile Thr Gln Leu
            115                 120                 125

Val Ser Met Phe Ala Gln Ala Gly Met Asn Asp Gly Gly Gly Thr Pro
        130                 135                 140

Trp Thr Asn Pro Gly Leu Ala Glu Asn Phe Met Asn Ser Phe Met Gln
145                 150                 155                 160

Gly Leu Ser Ser Met Pro Gly Phe Thr Ala Ser Gln Leu Asp Asp Met
                165                 170                 175
```

```
Ser Thr Ile Ala Gln Ser Met Val Gln Ser Ile Gln Ser Leu Ala Ala
                180                 185                 190

Gln Gly Arg Thr Ser Pro Asn Lys Leu Gln Ala Leu Asn Met Ala Phe
            195                 200                 205

Ala Ser Ser Met Ala Glu Ile Ala Ala Ser Glu Glu Gly Gly Gly Ser
        210                 215                 220

Leu Ser Thr Lys Thr Ser Ser Ile Ala Ser Ala Met Ser Asn Ala Phe
225                 230                 235                 240

Leu Gln Thr Thr Gly Val Val Asn Gln Pro Phe Ile Asn Glu Ile Thr
                245                 250                 255

Gln Leu Val Ser Met Phe Ala Gln Ala Gly Met Asn Asp Val Ser Ala
            260                 265                 270

Gly Asn Ser Gly Gln Gly Gly Tyr Gly Gly Leu Gly Gln Gly Gly Tyr
        275                 280                 285

Gly Gln Gly Ala Gly Ser Ser Ala Ala Ala Ala Ala Ala Ala Ala Ala
290                 295                 300

Ala Ala Ala Gly Gly Gln Gly Gly Gln Gly Gly Tyr Gly Gln Gly Gln
305                 310                 315                 320

Gly Ser Gly Gly Ser Ala Ala Ala Ala Ala Ala Ala Ala Ala Ala Ala
            325                 330                 335

Ala Ala Ala Ala Gly Arg Gly Gln Gly Gly Tyr Gly Gln Gly Ser Gly
        340                 345                 350

Gly Asn Ala Ala Ala Ala Ala Ala Ala Ala Ala Ala Ala Ala Ala Ala
        355                 360                 365

Ala Gly Gln Gly Gly Gln Gly Gly Tyr Gly Arg Gln Ser Gln Gly Ala
    370                 375                 380

Gly Ser Ala Ala Ala Ala Ala Ala Ala Ala Ala Ala Ala Ala Ala Ala
385                 390                 395                 400

Gly Ser Gly Gln Gly Gly Tyr Gly Gly Gln Gly Gln Gly Gly Tyr Gly
                405                 410                 415

Gln Ser Ser Ala Ser Ala Ser Ala Ala Ser Ala Ala Ser Thr Val
            420                 425                 430

Ala Asn Ser Val Ser Arg Leu Ser Ser Pro Ser Ala Val Ser Arg Val
        435                 440                 445

Ser Ser Ala Val Ser Ser Leu Val Ser Asn Gly Gln Val Asn Met Ala
450                 455                 460

Ala Leu Pro Asn Ile Ile Ser Asn Ile Ser Ser Ser Val Ser Ala Ser
465                 470                 475                 480

Ala Pro Gly Ala Ser Gly Cys Glu Val Ile Val Gln Ala Leu Leu Glu
            485                 490                 495

Val Ile Thr Ala Leu Val Gln Ile Val Ser Ser Ser Val Gly Tyr
        500                 505                 510

Ile Asn Pro Ser Ala Val Asn Gln Ile Thr Asn Val Val Ala Asn Ala
        515                 520                 525

Met Ala Gln Val Met Gly
        530

<210> SEQ ID NO 24
<211> LENGTH: 1602
<212> TYPE: DNA
<213> ORGANISM: Euprosthenops australis

<400> SEQUENCE: 24
atgggccatc atcatcatca tcatatgagc cataccaccc cgtggaccaa cccgggcctg     60
```

```
gcggaaaact ttatgaacag ctttatgcag ggcctgagca gcatgccggg ctttaccgcg    120
agccagctgg atgatatgag caccattgcg cagagcatgg tgcagagcat tcagagcctg    180
gcggcgcagg gccgtaccag cccgaacaaa ctgcaggcgc tgaacatggc gtttgcgagc    240
agcatggcgg aaattgcggc gagcgaagaa ggcggcggca gcctgagcac caaaaccagc    300
agcattgcga gcgcgatgag caacgcgttt ctgcagacca ccggcgtggt gaaccagccg    360
tttattaacg aaattaccca gctggtgagc atgtttgcgc aggccggtat gaatgacggc    420
ggcggcaccc cgtggaccaa cccgggcctg gcggaaaact ttatgaacag ctttatgcag    480
ggcctgagca gcatgccggg ctttaccgcg agccagctgg atgatatgag caccattgcg    540
cagagcatgg tgcagagcat tcagagcctg gcggcgcagg gccgtaccag cccgaacaaa    600
ctgcaggcgc tgaacatggc gtttgcgagc agcatggcgg aaattgcggc gagcgaagaa    660
ggcggcggca gcctgagcac caaaaccagc agcattgcga gcgcgatgag caacgcgttt    720
ctgcagacca ccggcgtggt gaaccagccg tttattaacg aaattaccca gctggtgagc    780
atgtttgcgc aggcgggcat gaacgatgtg agcgcgggga attcaggtca aggtggatat    840
ggtggactag gtcaaggagg atatggacaa ggtgcaggaa gttctgcagc cgctgccgcc    900
gccgcagcag ccgccgcagc aggtggacaa ggtggacaag gtcaaggagg atatggacaa    960
ggttcaggag ttctgcagc cgccgccgcc gccgcagcag cagcagcagc tgcagcagct    1020
ggacgaggtc aaggaggata tggtcaaggt tctggaggta atgctgctgc cgcagccgct    1080
gccgccgccg ccgccgctgc agcagccgga cagggaggtc aaggtggata tggtagacaa    1140
agccaaggtg ctggttccgc tgctgctgct gctgctgctg ctgccgctgc tgctgctgca    1200
ggatctggac aaggtggata cggtggacaa ggtcaaggag gttatggtca gagtagtgct    1260
tctgcttcag ctgctgcgtc agctgctagt actgtagcta attcggtgag tcgcctctca    1320
tcgccttccg cagtatctcg agtttcttca gcagtttcta gcttggtttc aaatggtcaa    1380
gtgaatatgg cagcgttacc taatatcatt tccaacattt cttcttctgt cagtgcatct    1440
gctcctggtg cttctggatg tgaggtcata gtgcaagctc tactcgaagt catcactgct    1500
cttgttcaaa tcgttagttc ttctagtgtt ggatatatta atccatctgc tgtgaaccaa    1560
attactaatg ttgttgctaa tgccatggct caagtaatgg gc                      1602
```

<210> SEQ ID NO 25
<211> LENGTH: 514
<212> TYPE: PRT
<213> ORGANISM: Euprosthenops australis

<400> SEQUENCE: 25

```
Gly Ser Gly Asn Ser His Thr Thr Pro Trp Thr Asn Pro Gly Leu Ala
1               5                   10                  15

Glu Asn Phe Met Asn Ser Phe Met Gln Gly Leu Ser Ser Met Pro Gly
            20                  25                  30

Phe Thr Ala Ser Gln Leu Asp Asp Met Ser Thr Ile Ala Gln Ser Met
        35                  40                  45

Val Gln Ser Ile Gln Ser Leu Ala Ala Gln Gly Arg Thr Ser Pro Asn
    50                  55                  60

Lys Leu Gln Ala Leu Asn Met Ala Phe Ala Ser Ser Met Ala Glu Ile
65                  70                  75                  80

Ala Ala Ser Glu Glu Gly Gly Gly Ser Leu Ser Thr Lys Thr Ser Ser
                85                  90                  95

Ile Ala Ser Ala Met Ser Asn Ala Phe Leu Gln Thr Thr Gly Val Val
```

-continued

```
                100                 105                 110
Asn Gln Pro Phe Ile Asn Glu Ile Thr Gln Leu Val Ser Met Phe Ala
            115                 120                 125
Gln Ala Gly Met Asn Asp Val Ser Ala Gly Tyr Gly Gln Gly Ala Gly
        130                 135                 140
Ser Ser Ala Ala Ala Ala Ala Ala Ala Ala Ala Ala Ala Ala Ala Ala
145                 150                 155                 160
Gly Arg Gly Gln Gly Gly Tyr Gly Gln Gly Ser Gly Gly Asn Ala Ala
                165                 170                 175
Ala Ala Ala Ala Ala Ala Ala Ala Ala Ser Gly Gln Gly Ser Gln
            180                 185                 190
Gly Gly Gln Gly Gly Gln Gly Gly Tyr Gly Gln Gly Ala Gly
        195                 200                 205
Ser Ser Ala Ala Ala Ala Ala Ala Ala Ala Ala Ala Ala Ala Ala Ser
        210                 215                 220
Gly Arg Gly Gln Gly Gly Tyr Gly Gln Gly Ala Gly Gly Asn Ala Ala
225                 230                 235                 240
Ala Ala Ala Ala Ala Ala Ala Ala Ala Ala Gly Gln Gly Gly
                245                 250                 255
Gln Gly Gly Tyr Gly Gly Leu Gly Gln Gly Gly Tyr Gly Gln Gly Ala
            260                 265                 270
Gly Ser Ser Ala Ala Ala Ala Ala Ala Ala Ala Ala Ala Ala Ala Gly
        275                 280                 285
Gly Gln Gly Gly Gln Gly Gln Gly Gly Tyr Gly Gln Gly Ser Gly Gly
        290                 295                 300
Ser Ala Ala Ala Ala Ala Ala Ala Ala Ala Ala Ala Ala Ala Ala Ala
305                 310                 315                 320
Gly Arg Gly Gln Gly Gly Tyr Gly Gln Gly Ser Gly Gly Asn Ala Ala
                325                 330                 335
Ala Ala Ala Ala Ala Ala Ala Ala Ala Ala Ala Gly Gln Gly
            340                 345                 350
Gly Gln Gly Gly Tyr Gly Arg Gln Ser Gln Gly Ala Gly Ser Ala Ala
        355                 360                 365
Ala Ala Ala Ala Ala Ala Ala Ala Ala Ala Ala Ala Gly Ser Gly Gln
        370                 375                 380
Gly Gly Tyr Gly Gly Gln Gly Gln Gly Gly Tyr Gly Gln Ser Ser Ala
385                 390                 395                 400
Ser Ala Ser Ala Ala Ser Ala Ala Ser Thr Val Ala Asn Ser Val
            405                 410                 415
Ser Arg Leu Ser Ser Pro Ser Ala Val Ser Arg Val Ser Ser Ala Val
            420                 425                 430
Ser Ser Leu Val Ser Asn Gly Gln Val Asn Met Ala Ala Leu Pro Asn
            435                 440                 445
Ile Ile Ser Asn Ile Ser Ser Val Ser Ala Ser Ala Pro Gly Ala
            450                 455                 460
Ser Gly Cys Glu Val Ile Val Gln Ala Leu Leu Glu Val Ile Thr Ala
465                 470                 475                 480
Leu Val Gln Ile Val Ser Ser Ser Val Gly Tyr Ile Asn Pro Ser
            485                 490                 495
Ala Val Asn Gln Ile Thr Asn Val Val Ala Asn Ala Met Ala Gln Val
            500                 505                 510
Met Gly
```

<210> SEQ ID NO 26
<211> LENGTH: 176
<212> TYPE: PRT
<213> ORGANISM: Artificial Sequence
<220> FEATURE:
<223> OTHER INFORMATION: Fusion protein

<400> SEQUENCE: 26

```
Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Val Ser Ala Met Ile
    130                 135                 140

Pro Ser Ser Pro Val His Leu Lys Arg Leu Lys Leu Leu Leu Leu Leu
145                 150                 155                 160

Leu Leu Leu Ile Leu Leu Leu Ile Leu Gly Ala Leu Leu Leu Gly Leu
                165                 170                 175
```

<210> SEQ ID NO 27
<211> LENGTH: 528
<212> TYPE: DNA
<213> ORGANISM: Artificial Sequence
<220> FEATURE:
<223> OTHER INFORMATION: Fusion protein

<400> SEQUENCE: 27

```
atgggccatc atcatcatca tcatatgagc cataccaccc cgtggaccaa cccgggcctg      60
gcggaaaact ttatgaacag ctttatgcag ggcctgagca gcatgccggg ctttaccgcg     120
agccagctgg atgatatgag caccattgcg cagagcatgg tgcagagcat tcagagcctg     180
gcggcgcagg gccgtaccag cccgaacaaa ctgcaggcgc tgaacatggc gtttgcgagc     240
agcatggcgg aaattgcggc gagcgaagaa ggcggcggca gcctgagcac caaaaccagc     300
agcattgcga gcgcgatgag caacgcgttt ctgcagacca ccggcgtggt gaaccagccg     360
tttattaacg aaattaccca gctggtgagc atgtttgcgc aggcgggcat gaacgatgtg     420
agcgcgatga ttccgagcag cccggtgcat ctgaaacgcc tgaaactgct gctgctgctg     480
ctgctgctga ttctgctgct gattctgggc gcgctgctgc tgggcctg                 528
```

<210> SEQ ID NO 28
<211> LENGTH: 309
<212> TYPE: PRT
<213> ORGANISM: Artificial Sequence
<220> FEATURE:
<223> OTHER INFORMATION: Fusion protein

<400> SEQUENCE: 28

| | | | | | | | | | | | | | | |
|---|---|---|---|---|---|---|---|---|---|---|---|---|---|---|
| Met | Gly | His | His | His | His | His | Met | Ser | His | Thr | Thr | Pro | Trp | Thr |
| 1 | | | 5 | | | | | 10 | | | | | 15 | |
| Asn | Pro | Gly | Leu | Ala | Glu | Asn | Phe | Met | Asn | Ser | Phe | Met | Gln | Gly | Leu |
| | | | 20 | | | | | 25 | | | | | 30 | | |
| Ser | Ser | Met | Pro | Gly | Phe | Thr | Ala | Ser | Gln | Leu | Asp | Asp | Met | Ser | Thr |
| | | 35 | | | | | 40 | | | | | 45 | | | |
| Ile | Ala | Gln | Ser | Met | Val | Gln | Ser | Ile | Gln | Ser | Leu | Ala | Ala | Gln | Gly |
| | 50 | | | | | 55 | | | | | 60 | | | | |
| Arg | Thr | Ser | Pro | Asn | Lys | Leu | Gln | Ala | Leu | Asn | Met | Ala | Phe | Ala | Ser |
| 65 | | | | | 70 | | | | | 75 | | | | | 80 |
| Ser | Met | Ala | Glu | Ile | Ala | Ala | Ser | Glu | Glu | Gly | Gly | Ser | Leu | Ser |
| | | | | 85 | | | | | 90 | | | | | 95 |
| Thr | Lys | Thr | Ser | Ser | Ile | Ala | Ser | Ala | Met | Ser | Asn | Ala | Phe | Leu | Gln |
| | | | 100 | | | | | 105 | | | | | 110 | | |
| Thr | Thr | Gly | Val | Val | Asn | Gln | Pro | Phe | Ile | Asn | Glu | Ile | Thr | Gln | Leu |
| | | 115 | | | | | 120 | | | | | 125 | | | |
| Val | Ser | Met | Phe | Ala | Gln | Ala | Gly | Met | Asn | Asp | Gly | Gly | Thr | Pro |
| 130 | | | | | 135 | | | | | 140 | | | | | |
| Trp | Thr | Asn | Pro | Gly | Leu | Ala | Glu | Asn | Phe | Met | Asn | Ser | Phe | Met | Gln |
| 145 | | | | | 150 | | | | | 155 | | | | | 160 |
| Gly | Leu | Ser | Ser | Met | Pro | Gly | Phe | Thr | Ala | Ser | Gln | Leu | Asp | Asp | Met |
| | | | | 165 | | | | | 170 | | | | | 175 | |
| Ser | Thr | Ile | Ala | Gln | Ser | Met | Val | Gln | Ser | Ile | Gln | Ser | Leu | Ala | Ala |
| | | | 180 | | | | | 185 | | | | | 190 | | |
| Gln | Gly | Arg | Thr | Ser | Pro | Asn | Lys | Leu | Gln | Ala | Leu | Asn | Met | Ala | Phe |
| | | 195 | | | | | 200 | | | | | 205 | | | |
| Ala | Ser | Ser | Met | Ala | Glu | Ile | Ala | Ala | Ser | Glu | Glu | Gly | Gly | Ser |
| | 210 | | | | | 215 | | | | | 220 | | | | |
| Leu | Ser | Thr | Lys | Thr | Ser | Ser | Ile | Ala | Ser | Ala | Met | Ser | Asn | Ala | Phe |
| 225 | | | | | 230 | | | | | 235 | | | | | 240 |
| Leu | Gln | Thr | Thr | Gly | Val | Val | Asn | Gln | Pro | Phe | Ile | Asn | Glu | Ile | Thr |
| | | | | 245 | | | | | 250 | | | | | 255 | |
| Gln | Leu | Val | Ser | Met | Phe | Ala | Gln | Ala | Gly | Met | Asn | Asp | Val | Ser | Ala |
| | | | 260 | | | | | 265 | | | | | 270 | | |
| Gly | Asn | Ser | Met | Ile | Pro | Ser | Ser | Pro | Val | His | Leu | Lys | Arg | Leu | Lys |
| | | 275 | | | | | 280 | | | | | 285 | | | |
| Leu | Leu | Leu | Leu | Leu | Leu | Leu | Leu | Ile | Leu | Leu | Leu | Ile | Leu | Gly | Ala |
| | 290 | | | | | 295 | | | | | 300 | | | | |
| Leu | Leu | Leu | Gly | Leu |
| 305 | | | | |

<210> SEQ ID NO 29
<211> LENGTH: 927
<212> TYPE: DNA
<213> ORGANISM: Artificial Sequence
<220> FEATURE:
<223> OTHER INFORMATION: Fusion protein

<400> SEQUENCE: 29

```
atgggccatc atcatcatca tcatatgagc cataccaccc cgtggaccaa cccgggcctg     60 gcggaaaaact ttatgaacag ctttatgcag ggcctgagca gcatgccggg ctttaccgcg    120
agccagctgg atgatatgag caccattgcg cagagcatgg tgcagagcat tcagagcctg    180
gcggcgcagg gccgtaccag cccgaacaaa ctgcaggcgc tgaacatggc gtttgcgagc    240
```

```
agcatggcgg aaattgcggc gagcgaagaa ggcggcggca gcctgagcac caaaaccagc    300
agcattgcga gcgcgatgag caacgcgttt ctgcagacca ccggcgtggt gaaccagccg    360
tttattaacg aaattaccca gctggtgagc atgtttgcgc aggccggtat gaatgacggc    420
ggcggcaccc cgtggaccaa cccgggcctg gcggaaaact ttatgaacag ctttatgcag    480
ggcctgagca gcatgccggg ctttaccgcg agccagctgg atgatatgag caccattgcg    540
cagagcatgg tgcagagcat tcagagcctg gcggcgcagg gccgtaccag cccgaacaaa    600
ctgcaggcgc tgaacatggc gtttgcgagc agcatggcgg aaattgcggc gagcgaagaa    660
ggcggcggca gcctgagcac caaaaccagc agcattgcga gcgcgatgag caacgcgttt    720
ctgcagacca ccggcgtggt gaaccagccg tttattaacg aaattaccca gctggtgagc    780
atgtttgcgc aggcgggcat gaacgatgtg agcgcgggga attctatgat tccgagcagc    840
ccggtgcatc tgaaacgcct gaaactgctg ctgctgctgc tgctgctgat tctgctgctg    900
attctgggcg cgctgctgct gggcctg                                       927

<210> SEQ ID NO 30
<211> LENGTH: 313
<212> TYPE: PRT
<213> ORGANISM: Artificial Sequence
<220> FEATURE:
<223> OTHER INFORMATION: Fusion protein

<400> SEQUENCE: 30

Met Gly His His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
    50                  55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Gly Gly Thr Pro
    130                 135                 140

Trp Thr Asn Pro Gly Leu Ala Glu Asn Phe Met Asn Ser Phe Met Gln
145                 150                 155                 160

Gly Leu Ser Ser Met Pro Gly Phe Thr Ala Ser Gln Leu Asp Asp Met
                165                 170                 175

Ser Thr Ile Ala Gln Ser Met Val Gln Ser Ile Gln Ser Leu Ala Ala
            180                 185                 190

Gln Gly Arg Thr Ser Pro Asn Lys Leu Gln Ala Leu Asn Met Ala Phe
        195                 200                 205

Ala Ser Ser Met Ala Glu Ile Ala Ala Ser Glu Glu Gly Gly Gly Ser
    210                 215                 220

Leu Ser Thr Lys Thr Ser Ser Ile Ala Ser Ala Met Ser Asn Ala Phe
225                 230                 235                 240
```

```
Leu Gln Thr Thr Gly Val Val Asn Gln Pro Phe Ile Asn Glu Ile Thr
                245                 250                 255

Gln Leu Val Ser Met Phe Ala Gln Ala Gly Met Asn Asp Val Ser Ala
            260                 265                 270

Gly Asn Ser Met Leu Leu Gly Asp Phe Phe Arg Lys Ser Lys Glu Lys
        275                 280                 285

Ile Gly Lys Glu Phe Lys Arg Ile Val Gln Arg Ile Lys Asp Phe Leu
    290                 295                 300

Arg Asn Leu Val Pro Arg Thr Glu Ser
305                 310
```

<210> SEQ ID NO 31
<211> LENGTH: 939
<212> TYPE: DNA
<213> ORGANISM: Artificial Sequence
<220> FEATURE:
<223> OTHER INFORMATION: Fusion protein

<400> SEQUENCE: 31

```
atgggccatc atcatcatca tcatatgagc ataccaccc cgtggaccaa cccgggcctg      60
gcggaaaact ttatgaacag ctttatgcag ggcctgagca gcatgccggg ctttaccgcg     120
agccagctgg atgatatgag caccattgcg cagagcatgg tgcagagcat tcagagcctg    180
gcggcgcagg gccgtaccag cccgaacaaa ctgcaggcgc tgaacatggc gtttgcgagc    240
agcatggcgg aaattgcggc gagcgaagaa ggcggcggca gcctgagcac caaaaccagc    300
agcattgcga gcgcgatgag caacgcgttt ctgcagacca ccggcgtggt gaaccagccg    360
tttattaacg aaattaccca gctggtgagc atgtttgcgc aggccggtat gaatgacggc    420
ggcggcaccc cgtggaccaa cccgggcctg gcggaaaact ttatgaacag ctttatgcag    480
ggcctgagca gcatgccggg ctttaccgcg agccagctgg atgatatgag caccattgcg    540
cagagcatgg tgcagagcat tcagagcctg gcggcgcagg gccgtaccag cccgaacaaa    600
ctgcaggcgc tgaacatggc gtttgcgagc agcatggcgg aaattgcggc gagcgaagaa    660
ggcggcggca gcctgagcac caaaaccagc agcattgcga gcgcgatgag caacgcgttt    720
ctgcagacca ccggcgtggt gaaccagccg tttattaacg aaattaccca gctggtgagc    780
atgtttgcgc aggcgggcat gaacgatgtg agcgcgggga attctatgct gctgggtgat    840
ttcttccgca aatctaaaga gaagattggc aaagagttta aagaattgt ccagagaatc     900
aaggattttt tgcggaatct tgtacccagg acagagtcc                          939
```

<210> SEQ ID NO 32
<211> LENGTH: 158
<212> TYPE: PRT
<213> ORGANISM: Euprosthenops australis

<400> SEQUENCE: 32

```
Met Ser His Thr Thr Pro Trp Thr Asn Pro Gly Leu Ala Glu Asn Phe
1               5                   10                  15

Met Asn Ser Phe Met Gln Gly Leu Ser Ser Met Pro Gly Phe Thr Ala
            20                  25                  30

Ser Gln Leu Asp Asp Met Ser Thr Ile Ala Gln Ser Met Val Gln Ser
        35                  40                  45

Ile Gln Ser Leu Ala Ala Gln Gly Arg Thr Ser Pro Asn Lys Leu Gln
    50                  55                  60

Ala Leu Asn Met Ala Phe Ala Ser Ser Met Ala Glu Ile Ala Ala Ser
```

```
                65                  70                  75                  80
Glu Glu Gly Gly Gly Ser Leu Ser Thr Lys Thr Ser Ser Ile Ala Ser
                    85                  90                  95

Ala Met Ser Asn Ala Phe Leu Gln Thr Thr Gly Val Val Asn Gln Pro
                    100                 105                 110

Phe Ile Asn Glu Ile Thr Gln Leu Val Ser Met Phe Ala Gln Ala Gly
                    115                 120                 125

Met Asn Asp Val Ser Ala Ser Ala Ser Ala Gly Ala Ser Ala Ala Ala
                130                 135                 140

Ser Ala Gly Ala Ala Ala Leu Glu His His His His His His
145                 150                 155

<210> SEQ ID NO 33
<211> LENGTH: 646
<212> TYPE: PRT
<213> ORGANISM: Euprosthenops australis

<400> SEQUENCE: 33

His His His His His Ser His Thr Thr Pro Trp Thr Asn Pro Gly
1               5                   10                  15

Leu Ala Glu Asn Phe Met Asn Ser Phe Met Gln Gly Leu Ser Ser Met
                20                  25                  30

Pro Gly Phe Thr Ala Ser Gln Leu Asp Asp Met Ser Thr Ile Ala Gln
                35                  40                  45

Ser Met Val Gln Ser Ile Gln Ser Leu Ala Ala Gln Gly Arg Thr Ser
        50                  55                  60

Pro Asn Lys Leu Gln Ala Leu Asn Met Ala Phe Ala Ser Ser Met Ala
65                  70                  75                  80

Glu Ile Ala Ala Ser Glu Glu Gly Gly Gly Ser Leu Ser Thr Lys Thr
                85                  90                  95

Ser Ser Ile Ala Ser Ala Met Ser Asn Ala Phe Leu Gln Thr Thr Gly
                100                 105                 110

Val Val Asn Gln Pro Phe Ile Asn Glu Ile Thr Gln Leu Val Ser Met
                115                 120                 125

Phe Ala Gln Ala Gly Met Asn Asp Gly Gly Gly Thr Pro Trp Thr Asn
            130                 135                 140

Pro Gly Leu Ala Glu Asn Phe Met Asn Ser Phe Met Gln Gly Leu Ser
145                 150                 155                 160

Ser Met Pro Gly Phe Thr Ala Ser Gln Leu Asp Asp Met Ser Thr Ile
                165                 170                 175

Ala Gln Ser Met Val Gln Ser Ile Gln Ser Leu Ala Ala Gln Gly Arg
                180                 185                 190

Thr Ser Pro Asn Lys Leu Gln Ala Leu Asn Met Ala Phe Ala Ser Ser
            195                 200                 205

Met Ala Glu Ile Ala Ala Ser Glu Glu Gly Gly Gly Ser Leu Ser Thr
        210                 215                 220

Lys Thr Ser Ser Ile Ala Ser Ala Met Ser Asn Ala Phe Leu Gln Thr
225                 230                 235                 240

Thr Gly Val Val Asn Gln Pro Phe Ile Asn Glu Ile Thr Gln Leu Val
                245                 250                 255

Ser Met Phe Ala Gln Ala Gly Met Asn Asp Val Ser Ala Gly Tyr Gly
                260                 265                 270

Gln Gly Ala Gly Ser Ser Ala Ala Ala Ala Ala Ala Ala Ala
            275                 280                 285
```

Ala Ala Ala Gly Arg Gly Gln Gly Gly Tyr Gly Gln Gly Ser Gly
290                 295                 300

Gly Asn Ala Ala Ala Ala Ala Ala Ala Ala Ala Ala Ala Ser Gly
305                 310                 315                 320

Gln Gly Ser Gln Gly Gly Gln Gly Gly Gln Gly Gly Gly Tyr Gly
            325                 330                 335

Gln Gly Ala Gly Ser Ala Ala Ala Ala Ala Ala Ala Ala Ala Ala
            340                 345                 350

Ala Ala Ala Ser Gly Arg Gly Gln Gly Gly Tyr Gly Gln Gly Ala Gly
        355                 360                 365

Gly Asn Ala Ala Ala Ala Ala Ala Ala Ala Ala Ala Ala Ala
370                 375                 380

Gly Gln Gly Gly Gln Gly Gly Tyr Gly Gly Leu Gly Gln Gly Gly Tyr
385                 390                 395                 400

Gly Gln Gly Ala Gly Ser Ser Ala Ala Ala Ala Ala Ala Ala Ala
                405                 410                 415

Ala Ala Ala Gly Gly Gln Gly Gly Gln Gly Gly Gly Tyr Gly Gln
            420                 425                 430

Gly Ser Gly Gly Ser Ala Ala Ala Ala Ala Ala Ala Ala Ala Ala
        435                 440                 445

Ala Ala Ala Ala Gly Arg Gly Gln Gly Gly Tyr Gly Gln Gly Ser Gly
450                 455                 460

Gly Asn Ala Ala Ala Ala Ala Ala Ala Ala Ala Ala Ala Ala Ala
465                 470                 475                 480

Ala Gly Gln Gly Gly Gln Gly Gly Tyr Gly Arg Gln Ser Gln Gly Ala
                485                 490                 495

Gly Ser Ala Ala Ala Ala Ala Ala Ala Ala Ala Ala Ala Ala
        500                 505                 510

Gly Ser Gly Gln Gly Gly Tyr Gly Gly Gln Gly Gln Gly Gly Tyr Gly
            515                 520                 525

Gln Ser Ser Ala Ser Ala Ser Ala Ala Ser Ala Ala Ser Thr Val
        530                 535                 540

Ala Asn Ser Val Ser Arg Leu Ser Ser Pro Ser Ala Val Ser Arg Val
545                 550                 555                 560

Ser Ser Ala Val Ser Ser Leu Val Ser Asn Gly Gln Val Asn Met Ala
                565                 570                 575

Ala Leu Pro Asn Ile Ile Ser Asn Ile Ser Ser Val Ser Ala Ser
            580                 585                 590

Ala Pro Gly Ala Ser Gly Cys Glu Val Ile Val Gln Ala Leu Leu Glu
        595                 600                 605

Val Ile Thr Ala Leu Val Gln Ile Val Ser Ser Ser Val Gly Tyr
610                 615                 620

Ile Asn Pro Ser Ala Val Asn Gln Ile Thr Asn Val Val Ala Asn Ala
625                 630                 635                 640

Met Ala Gln Val Met Gly
            645

<210> SEQ ID NO 34
<211> LENGTH: 387
<212> TYPE: PRT
<213> ORGANISM: Artificial Sequence
<220> FEATURE:
<223> OTHER INFORMATION: Fusion protein

<400> SEQUENCE: 34

```
Met Gly His His His His His Met Ser His Thr Thr Pro Trp Thr
1               5                   10                  15

Asn Pro Gly Leu Ala Glu Asn Phe Met Asn Ser Phe Met Gln Gly Leu
            20                  25                  30

Ser Ser Met Pro Gly Phe Thr Ala Ser Gln Leu Asp Asp Met Ser Thr
        35                  40                  45

Ile Ala Gln Ser Met Val Gln Ser Ile Gln Ser Leu Ala Ala Gln Gly
50              55                  60

Arg Thr Ser Pro Asn Lys Leu Gln Ala Leu Asn Met Ala Phe Ala Ser
65                  70                  75                  80

Ser Met Ala Glu Ile Ala Ala Ser Glu Glu Gly Gly Gly Ser Leu Ser
                85                  90                  95

Thr Lys Thr Ser Ser Ile Ala Ser Ala Met Ser Asn Ala Phe Leu Gln
            100                 105                 110

Thr Thr Gly Val Val Asn Gln Pro Phe Ile Asn Glu Ile Thr Gln Leu
        115                 120                 125

Val Ser Met Phe Ala Gln Ala Gly Met Asn Asp Gly Gly Thr Pro
    130                 135                 140

Trp Thr Asn Pro Gly Leu Ala Glu Asn Phe Met Asn Ser Phe Met Gln
145                 150                 155                 160

Gly Leu Ser Ser Met Pro Gly Phe Thr Ala Ser Gln Leu Asp Asp Met
                165                 170                 175

Ser Thr Ile Ala Gln Ser Met Val Gln Ser Ile Gln Ser Leu Ala Ala
            180                 185                 190

Gln Gly Arg Thr Ser Pro Asn Lys Leu Gln Ala Leu Asn Met Ala Phe
        195                 200                 205

Ala Ser Ser Met Ala Glu Ile Ala Ala Ser Glu Glu Gly Gly Gly Ser
    210                 215                 220

Leu Ser Thr Lys Thr Ser Ser Ile Ala Ser Ala Met Ser Asn Ala Phe
225                 230                 235                 240

Leu Gln Thr Thr Gly Val Val Asn Gln Pro Phe Ile Asn Glu Ile Thr
                245                 250                 255

Gln Leu Val Ser Met Phe Ala Gln Ala Gly Met Asn Asp Val Ser Ala
            260                 265                 270

Gly Asn Ser Glu His Leu Val Thr Thr Ala Thr Phe Ser Ile Gly Ser
        275                 280                 285

Thr Gly Leu Val Val Tyr Asp Tyr Gln Gln Leu Leu Ile Ala Tyr Lys
    290                 295                 300

Pro Ala Pro Gly Thr Cys Cys Tyr Ile Met Lys Ile Ala Pro Glu Ser
305                 310                 315                 320

Ile Pro Ser Leu Glu Ala Leu Thr Arg Lys Val His Asn Phe Gln Met
                325                 330                 335

Glu Cys Ser Leu Gln Ala Lys Pro Ala Val Pro Thr Ser Lys Leu Gly
            340                 345                 350

Gln Ala Glu Gly Arg Asp Ala Gly Ser Ala Pro Ser Gly Gly Asp Pro
        355                 360                 365

Ala Phe Leu Gly Met Ala Val Ser Thr Leu Cys Gly Glu Val Pro Leu
    370                 375                 380

Tyr Tyr Ile
385

<210> SEQ ID NO 35
<211> LENGTH: 178
<212> TYPE: PRT
```

```
<213> ORGANISM: Artificial Sequence
<220> FEATURE:
<223> OTHER INFORMATION: Fusion protein

<400> SEQUENCE: 35

Met Gly His His His His His His Met Ala Ser Ser Asp Lys Ile Ile
1               5                   10                  15

His Leu Thr Asp Asp Ser Phe Asp Thr Asp Val Leu Lys Ala Asp Gly
            20                  25                  30

Ala Ile Leu Val Asp Phe Trp Ala Glu Trp Cys Gly Pro Cys Lys Met
        35                  40                  45

Ile Ala Pro Ile Leu Asp Glu Ile Ala Asp Glu Tyr Gln Gly Lys Leu
    50                  55                  60

Thr Val Ala Lys Leu Asn Ile Asp Gln Asn Pro Gly Thr Ala Pro Lys
65                  70                  75                  80

Tyr Gly Ile Arg Gly Ile Pro Thr Leu Leu Leu Phe Lys Asn Gly Glu
                85                  90                  95

Val Ala Ala Thr Lys Val Gly Ala Leu Ser Lys Gly Gln Leu Lys Glu
            100                 105                 110

Phe Leu Asp Ala Asn Leu Ala Gly Ser Gly Ser Gly His Met His His
        115                 120                 125

His His His His Ser Ser Gly Leu Val Pro Arg Gly Ser Gly Asn Ser
    130                 135                 140

Met Ile Pro Ser Ser Pro Val His Leu Lys Arg Leu Lys Leu Leu Leu
145                 150                 155                 160

Leu Leu Leu Leu Leu Ile Leu Leu Leu Ile Leu Gly Ala Leu Leu Leu
                165                 170                 175

Gly Leu

<210> SEQ ID NO 36
<211> LENGTH: 537
<212> TYPE: DNA
<213> ORGANISM: Artificial Sequence
<220> FEATURE:
<223> OTHER INFORMATION: Fusion protein

<400> SEQUENCE: 36
atgggccatc atcatcatca tcatatggct agcagcgata aaattattca cctgactgac      60
gacagttttg acacggatgt actcaaagcg gacggggcga tcctcgtcga tttctgggca     120
gagtggtgcg gtccgtgcaa aatgatcgcc ccgattctgg atgaaatcgc tgacgaatat     180
cagggcaaac tgaccgttgc aaaactgaac atcgatcaaa accctggcac tgcgccgaaa     240
tatggcatcc gtggtatccc gactctgctg ctgttcaaaa acggtgaagt ggcggcaacc     300
aaagtgggtg cactgtctaa aggtcagttg aaagagttcc tcgacgctaa cctggccggt     360
tctggttctg gccatatgca ccatcatcat catcattctt ctggtctggt gccacgcggt     420
tctgggaatt ctatgattcc gagcagcccg gtgcatctga aacgcctgaa actgctgctg     480
ctgctgctgc tgctgattct gctgctgatt ctgggcgcgc tgctgctggg cctgtaa       537

<210> SEQ ID NO 37
<211> LENGTH: 313
<212> TYPE: PRT
<213> ORGANISM: Artificial Sequence
<220> FEATURE:
<223> OTHER INFORMATION: Fusion protein

<400> SEQUENCE: 37
```

```
Met Gly His His His His His Met Ala Ser Ser Asp Lys Ile Ile
1               5                   10                  15

His Leu Thr Asp Asp Ser Phe Asp Thr Asp Val Leu Lys Ala Asp Gly
            20                  25                  30

Ala Ile Leu Val Asp Phe Trp Ala Glu Trp Cys Gly Pro Cys Lys Met
                35                  40                  45

Ile Ala Pro Ile Leu Asp Glu Ile Ala Asp Glu Tyr Gln Gly Lys Leu
            50                  55                  60

Thr Val Ala Lys Leu Asn Ile Asp Gln Asn Pro Gly Thr Ala Pro Lys
65                  70                  75                  80

Tyr Gly Ile Arg Gly Ile Pro Thr Leu Leu Phe Lys Asn Gly Glu
                85                  90                  95

Val Ala Ala Thr Lys Val Gly Ala Leu Ser Lys Gly Gln Leu Lys Glu
            100                 105                 110

Phe Leu Asp Ala Asn Leu Ala Gly Ser Gly Ser Gly His Met His His
            115                 120                 125

His His His His Ser Ser Gly Leu Val Pro Arg Gly Ser Gly Asn Ser
            130                 135                 140

His Met Ser His Thr Thr Pro Trp Thr Asn Pro Gly Leu Ala Glu Asn
145                 150                 155                 160

Phe Met Asn Ser Phe Met Gln Gly Leu Ser Ser Met Pro Gly Phe Thr
                165                 170                 175

Ala Ser Gln Leu Asp Asp Met Ser Thr Ile Ala Gln Ser Met Val Gln
            180                 185                 190

Ser Ile Gln Ser Leu Ala Ala Gln Gly Arg Thr Ser Pro Asn Lys Leu
            195                 200                 205

Gln Ala Leu Asn Met Ala Phe Ala Ser Ser Met Ala Glu Ile Ala Ala
            210                 215                 220

Ser Glu Glu Gly Gly Gly Ser Leu Ser Thr Lys Thr Ser Ser Ile Ala
225                 230                 235                 240

Ser Ala Met Ser Asn Ala Phe Leu Gln Thr Thr Gly Val Val Asn Gln
                245                 250                 255

Pro Phe Ile Asn Glu Ile Thr Gln Leu Val Ser Met Phe Ala Gln Ala
            260                 265                 270

Gly Met Asn Asp Val Ser Ala Met Ile Pro Ser Ser Pro Val His Leu
            275                 280                 285

Lys Arg Leu Lys Leu Leu Leu Leu Leu Leu Leu Ile Leu Leu Leu
            290                 295                 300

Ile Leu Gly Ala Leu Leu Leu Gly Leu
305                 310
```

<210> SEQ ID NO 38
<211> LENGTH: 939
<212> TYPE: DNA
<213> ORGANISM: Artificial Sequence
<220> FEATURE:
<223> OTHER INFORMATION: Fusion protein

<400> SEQUENCE: 38

```
atgggccatc atcatcatca tcatatggct agcagcgata aaattattca cctgactgac    60
gacagttttg acacggatgt actcaaagcg acggggcgat cctcgtcga tttctgggca   120 gagtggtgcg gtccgtgcaa aatgatcgcc ccgattctgg atgaaatcgc tgacgaatat   180
cagggcaaac tgaccgttgc aaaactgaac atcgatcaaa accctggcac tgcgccgaaa   240
tatggcatcc gtggtatccc gactctgctg ctgttcaaaa acggtgaagt ggcggcaacc   300
```

```
aaagtgggtg cactgtctaa aggtcagttg aaagagttcc tcgacgctaa cctggccggt    360
tctggttctg gccatatgca ccatcatcat catcattctt ctggtctggt gccacgcggt    420
tctgggaatt cccatatgag ccataccacc ccgtggacca acccgggcct ggcggaaaac    480
tttatgaaca gctttatgca gggcctgagc agcatgccgg gctttaccgc gagccagctg    540
gatgatatga gcaccattgc gcagagcatg gtgcagagca ttcagagcct ggcggcgcag    600
ggccgcacca gcccgaacaa actgcaggcg ctgaacatgg cgtttgcgag cagcatggcg    660
gaaattgcgg cgagcgaaga aggcggcggc agcctgagca ccaaaaccag cagcattgcg    720
agcgcgatga gcaacgcgtt tctgcagacc accggcgtgg tgaaccagcc gtttattaac    780
gaaattaccc agctggtgag catgtttgcg caggcgggca tgaacgatgt gagcgcgatg    840
attccgagca gcccggtgca tctgaaacgc ctgaaattgc tgctgctgtt actgctgctg    900
attctgcttc tgattctggg cgcgctgctg ctgggcctg                          939
```

<210> SEQ ID NO 39
<211> LENGTH: 410
<212> TYPE: PRT
<213> ORGANISM: Artificial Sequence
<220> FEATURE:
<223> OTHER INFORMATION: Fusion protein

<400> SEQUENCE: 39

```
Met Gly His His His His His His Gly Gly Gly Ser Gly Gly Gly
 1               5                  10                  15

Gly Ser His His His His His His Met Ser His Thr Thr Pro Trp Thr
                20                  25                  30

Asn Pro Gly Leu Ala Glu Asn Phe Met Asn Ser Phe Met Gln Gly Leu
            35                  40                  45

Ser Ser Met Pro Gly Phe Thr Ala Ser Gln Leu Asp Asp Met Ser Thr
    50                  55                  60

Ile Ala Gln Ser Met Val Gln Ser Ile Gln Ser Leu Ala Ala Gln Gly
65                  70                  75                  80

Arg Thr Ser Pro Asn Lys Leu Gln Ala Leu Asn Met Ala Phe Ala Ser
                85                  90                  95

Ser Met Ala Glu Ile Ala Ala Ser Glu Glu Gly Gly Gly Ser Leu Ser
            100                 105                 110

Thr Lys Thr Ser Ser Ile Ala Ser Ala Met Ser Asn Ala Phe Leu Gln
        115                 120                 125

Thr Thr Gly Val Val Asn Gln Pro Phe Ile Asn Glu Ile Thr Gln Leu
    130                 135                 140

Val Ser Met Phe Ala Gln Ala Gly Met Asn Asp Gly Gly Gly Thr Pro
145                 150                 155                 160

Trp Thr Asn Pro Gly Leu Ala Glu Asn Phe Met Asn Ser Phe Met Gln
                165                 170                 175

Gly Leu Ser Ser Met Pro Gly Phe Thr Ala Ser Gln Leu Asp Asp Met
            180                 185                 190

Ser Thr Ile Ala Gln Ser Met Val Gln Ser Ile Gln Ser Leu Ala Ala
        195                 200                 205

Gln Gly Arg Thr Ser Pro Asn Lys Leu Gln Ala Leu Asn Met Ala Phe
    210                 215                 220

Ala Ser Ser Met Ala Glu Ile Ala Ala Ser Glu Glu Gly Gly Gly Ser
225                 230                 235                 240

Leu Ser Thr Lys Thr Ser Ser Ile Ala Ser Ala Met Ser Asn Ala Phe
```

```
                    245                 250                 255
Leu Gln Thr Thr Gly Val Val Asn Gln Pro Phe Ile Asn Glu Ile Thr
            260                 265                 270

Gln Leu Val Ser Met Phe Ala Gln Ala Gly Met Asn Asp Val Ser Ala
        275                 280                 285

Leu Glu Ala Leu Phe Gln Gly Pro Asn Ser Glu His Leu Val Thr Thr
    290                 295                 300

Ala Thr Phe Ser Ile Gly Ser Thr Gly Leu Val Val Tyr Asp Tyr Gln
305                 310                 315                 320

Gln Leu Leu Ile Ala Tyr Lys Pro Ala Pro Gly Thr Cys Cys Tyr Ile
                325                 330                 335

Met Lys Ile Ala Pro Glu Ser Ile Pro Ser Leu Glu Ala Leu Thr Arg
            340                 345                 350

Lys Val His Asn Phe Gln Met Glu Cys Ser Leu Gln Ala Lys Pro Ala
        355                 360                 365

Val Pro Thr Ser Lys Leu Gly Gln Ala Glu Arg Asp Ala Gly Ser
    370                 375                 380

Ala Pro Ser Gly Gly Asp Pro Ala Phe Leu Gly Met Ala Val Ser Thr
385                 390                 395                 400

Leu Cys Gly Glu Val Pro Leu Tyr Tyr Ile
                405                 410

<210> SEQ ID NO 40
<211> LENGTH: 1233
<212> TYPE: DNA
<213> ORGANISM: Artificial Sequence
<220> FEATURE:
<223> OTHER INFORMATION: Fusion protein

<400> SEQUENCE: 40
atgggccatc atcatcatca tcatggcggc ggtggtagcg gtggcggtgg cagccatcat     60
catcatcatc atatgagcca taccaccccg tggaccaacc cgggcctggc ggaaaacttt    120
atgaacagct ttatgcaggg cctgagcagc atgccgggct ttaccgcgag ccagctggat    180
gatatgagca ccattgcgca gagcatggtg cagagcattc agagcctggc ggcgcagggc    240
cgtaccagcc cgaacaaact gcaggcgctg aacatggcgt ttgcgagcag catggcggaa    300
attgcggcga gcaagaaggc ggcggcagc ctgagcacca aaaccagcag cattgcgagc    360
gcgatgagca acgcgtttct gcagaccacc ggcgtggtga ccagccgtt tattaacgaa    420 attcccagc tggtgagcat gtttgcgcag gcgggcatga cgatggcgg cggcacccccg    480 tggaccaacc cgggcctggc ggaaaacttt atgaacagct ttatgcaggg cctgagcagc    540
atgccgggct ttaccgcgag ccagctggat gatatgagca ccattgcgca gagcatggtg    600
cagagcattc agagcctggc ggcgcagggc cgtaccagcc cgaacaaact gcaggcgctg    660
aacatggcgt ttgcgagcag catggcggaa attgcggcga gcaagaaggc ggcggcagc    720 ctgagcacca aaaccagcag cattgcgagc gcgatgagca acgcgtttct gcagaccacc    780
ggcgtggtga ccagccgtt tattaacgaa attcccagc tggtgagcat gtttgcgcag    840
gcgggcatga cgatgtgag cgcgctgaa gcgctgttcc agggcccgaa ttcagagcac    900
ctggttacca ctgccacctt ctccatcggc tccactggcc tcgtggtgta tgactaccag    960
cagctgctga tcgcctacaa gccagcccct ggcacctgct gctacatcat gaagatagct   1020
ccagagagca tccccagtct tgaggctctc actagaaaag tccacaactt ccagatggaa   1080
tgctctctgc aggccaagcc cgcagtgcct acgtctaagc tgggccaggc agaggggcga   1140
```

```
gatgcaggct cagcaccctc cggaggggac ccggccttcc tgggcatggc cgtgagcacc    1200
ctgtgtggcg aggtgccgct ctactacatc tag                                 1233
```

<210> SEQ ID NO 41
<211> LENGTH: 116
<212> TYPE: PRT
<213> ORGANISM: Homo sapiens

<400> SEQUENCE: 41

```
Gly Pro Asn Ser Glu His Leu Val Thr Thr Ala Thr Phe Ser Ile Gly
1               5                   10                  15

Ser Thr Gly Leu Val Val Tyr Asp Tyr Gln Gln Leu Leu Ile Ala Tyr
                20                  25                  30

Lys Pro Ala Pro Gly Thr Cys Cys Tyr Ile Met Lys Ile Ala Pro Glu
            35                  40                  45

Ser Ile Pro Ser Leu Glu Ala Leu Thr Arg Lys Val His Asn Phe Gln
        50                  55                  60

Met Glu Cys Ser Leu Gln Ala Lys Pro Ala Val Pro Thr Ser Lys Leu
65                  70                  75                  80

Gly Gln Ala Glu Gly Arg Asp Ala Gly Ser Ala Pro Gly Gly Asp
                85                  90                  95

Pro Ala Phe Leu Gly Met Ala Val Ser Thr Leu Cys Gly Glu Val Pro
            100                 105                 110

Leu Tyr Tyr Ile
        115
```

<210> SEQ ID NO 42
<211> LENGTH: 537
<212> TYPE: PRT
<213> ORGANISM: Artificial Sequence
<220> FEATURE:
<223> OTHER INFORMATION: Fusion protein

<400> SEQUENCE: 42

```
Met Gly His His His His His Gly Gly Gly Gly Ser Gly Gly Gly
1               5                   10                  15

Gly Ser His His His His His Met Ser His Thr Thr Pro Trp Thr
                20                  25                  30

Asn Pro Gly Leu Ala Glu Asn Phe Met Asn Ser Phe Met Gln Gly Leu
            35                  40                  45

Ser Ser Met Pro Gly Phe Thr Ala Ser Gln Leu Asp Asp Met Ser Thr
        50                  55                  60

Ile Ala Gln Ser Met Val Gln Ser Ile Gln Ser Leu Ala Ala Gln Gly
65                  70                  75                  80

Arg Thr Ser Pro Asn Lys Leu Gln Ala Leu Asn Met Ala Phe Ala Ser
                85                  90                  95

Ser Met Ala Glu Ile Ala Ala Ser Glu Glu Gly Gly Gly Ser Leu Ser
            100                 105                 110

Thr Lys Thr Ser Ser Ile Ala Ser Ala Met Ser Asn Ala Phe Leu Gln
        115                 120                 125

Thr Thr Gly Val Val Asn Gln Pro Phe Ile Asn Glu Ile Thr Gln Leu
    130                 135                 140

Val Ser Met Phe Ala Gln Ala Gly Met Asn Asp Gly Gly Gly Thr Pro
145                 150                 155                 160

Trp Thr Asn Pro Gly Leu Ala Glu Asn Phe Met Asn Ser Phe Met Gln
                165                 170                 175
```

Gly Leu Ser Ser Met Pro Gly Phe Thr Ala Ser Gln Leu Asp Asp Met
            180                 185                 190

Ser Thr Ile Ala Gln Ser Met Val Gln Ser Ile Gln Ser Leu Ala Ala
            195                 200                 205

Gln Gly Arg Thr Ser Pro Asn Lys Leu Gln Ala Leu Asn Met Ala Phe
210                 215                 220

Ala Ser Ser Met Ala Glu Ile Ala Ala Ser Glu Glu Gly Gly Gly Ser
225                 230                 235                 240

Leu Ser Thr Lys Thr Ser Ser Ile Ala Ser Ala Met Ser Asn Ala Phe
            245                 250                 255

Leu Gln Thr Thr Gly Val Val Asn Gln Pro Phe Ile Asn Glu Ile Thr
            260                 265                 270

Gln Leu Val Ser Met Phe Ala Gln Ala Gly Met Asn Asp Val Ser Ala
            275                 280                 285

Leu Glu Ala Leu Phe Gln Gly Pro Asn Ser Lys Gly Glu Glu Leu Phe
290                 295                 300

Thr Gly Val Val Pro Ile Leu Val Glu Leu Asp Gly Asp Val Asn Gly
305                 310                 315                 320

His Lys Phe Ser Val Ser Gly Glu Gly Glu Gly Asp Ala Thr Tyr Gly
            325                 330                 335

Lys Leu Thr Leu Lys Phe Ile Cys Thr Thr Gly Lys Leu Pro Val Pro
            340                 345                 350

Trp Pro Thr Leu Val Thr Thr Leu Thr Tyr Gly Val Gln Cys Phe Ser
            355                 360                 365

Arg Tyr Pro Asp His Met Lys Gln His Asp Phe Phe Lys Ser Ala Met
            370                 375                 380

Pro Glu Gly Tyr Val Gln Glu Arg Thr Ile Phe Phe Lys Asp Asp Gly
385                 390                 395                 400

Asn Tyr Lys Thr Arg Ala Glu Val Lys Phe Glu Gly Asp Thr Leu Val
            405                 410                 415

Asn Arg Ile Glu Leu Lys Gly Ile Asp Phe Lys Glu Asp Gly Asn Ile
            420                 425                 430

Leu Gly His Lys Leu Glu Tyr Asn Tyr Asn Ser His Asn Val Tyr Ile
            435                 440                 445

Met Ala Asp Lys Gln Lys Asn Gly Ile Lys Val Asn Phe Lys Ile Arg
450                 455                 460

His Asn Ile Glu Asp Gly Ser Val Gln Leu Ala Asp His Tyr Gln Gln
465                 470                 475                 480

Asn Thr Pro Ile Gly Asp Gly Pro Val Leu Leu Pro Asp Asn His Tyr
            485                 490                 495

Leu Ser Thr Gln Ser Ala Leu Ser Lys Asp Pro Asn Glu Lys Arg Asp
            500                 505                 510

His Met Val Leu Leu Glu Phe Val Thr Ala Ala Gly Ile Thr Leu Gly
            515                 520                 525

Met Asp Glu Leu Tyr Lys Leu Ile Asn
530                 535

<210> SEQ ID NO 43
<211> LENGTH: 1620
<212> TYPE: DNA
<213> ORGANISM: Artificial Sequence
<220> FEATURE:
<223> OTHER INFORMATION: Fusion protein

<400> SEQUENCE: 43

```
atgggccatc atcatcatca tcatggcggc ggtggtagcg gtggcggtgg cagccatcat      60
catcatcatc atatgagcca taccaccccg tggaccaacc cgggcctggc ggaaaacttt     120
atgaacagct ttatgcaggg cctgagcagc atgccgggct taccgcgag ccagctggat     180
gatatgagca ccattgcgca gagcatggtg cagagcattc agagcctggc ggcgcagggc     240
cgtaccagcc cgaacaaact gcaggcgctg aacatggcgt tgcgagcag catggcggaa     300
attgcggcga gcgaagaagg cggcggcagc ctgagcacca aaaccagcag cattgcgagc     360
gcgatgagca acgcgtttct gcagaccacc ggcgtggtga accagccgtt tattaacgaa     420
attacccagc tggtgagcat gtttgcgcag gcgggcatga cgatggcgg cggcaccccg     480
tggaccaacc cgggcctggc ggaaaacttt atgaacagct ttatgcaggg cctgagcagc     540
atgccgggct taccgcgag ccagctggat gatatgagca ccattgcgca gagcatggtg     600
cagagcattc agagcctggc ggcgcagggc cgtaccagcc cgaacaaact gcaggcgctg     660
aacatggcgt tgcgagcag catggcggaa attgcggcga gcgaagaagg cggcggcagc     720
ctgagcacca aaaccagcag cattgcgagc gcgatgagca acgcgtttct gcagaccacc     780
ggcgtggtga accagccgtt tattaacgaa attacccagc tggtgagcat gtttgcgcag     840
gcgggcatga cgatgtgag cgcgctggaa gcgctgttcc agggcccgaa ttcaaagggc     900
gaggagctgt tcaccgggt ggtgcccatc ctggtcgagc tggacggcga cgtaaacggc     960
cacaagttca gcgtgtccgg cgagggcgag ggcgatgcca cctacggcaa gctgaccctg    1020
aagttcatct gcaccaccgg caagctgccc gtgccctggc ccaccctcgt gaccaccctg    1080
acctacggcg tgcagtgctt cagccgctac cccgaccaca tgaagcagca cgacttcttc    1140
aagtccgcca tgcccgaagg ctacgtccag gagcgcacca tcttcttcaa ggacgacggc    1200
aactacaaga cccgcgccga ggtgaagttc gagggcgaca ccctggtgaa ccgcatcgag    1260
ctgaagggca tcgacttcaa ggaggacggc aacatcctgg gcacaagct ggagtacaac    1320
tacaacagcc acaacgtcta tatcatggcc gacaagcaga agaacggcat caaggtgaac    1380
ttcaagatcc gccacaacat cgaggacggc agcgtgcagc tcgccgacca ctaccagcag    1440
aacacccca tcggcgacgg ccccgtgctg ctgcccgaca ccactacct gagcacccag    1500
tccgccctga gcaaagaccc caacgagaag cgcgatcaca tggtcctgct ggagttcgtg    1560
accgccgccg ggatcactct cggcatggac gagctgtaca agttaattaa ctaatgataa    1620
```

<210> SEQ ID NO 44
<211> LENGTH: 243
<212> TYPE: PRT
<213> ORGANISM: Aequorea victoria

<400> SEQUENCE: 44

Gly Pro Asn Ser Lys Gly Glu Glu Leu Phe Thr Gly Val Val Pro Ile
1               5                   10                  15

Leu Val Glu Leu Asp Gly Asp Val Asn Gly His Lys Phe Ser Val Ser
            20                  25                  30

Gly Glu Gly Glu Gly Asp Ala Thr Tyr Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln

```
                    85                  90                  95

Glu Arg Thr Ile Phe Phe Lys Asp Asp Gly Asn Tyr Lys Thr Arg Ala
                100                 105                 110

Glu Val Lys Phe Glu Gly Asp Thr Leu Val Asn Arg Ile Glu Leu Lys
            115                 120                 125

Gly Ile Asp Phe Lys Glu Asp Gly Asn Ile Leu Gly His Lys Leu Glu
        130                 135                 140

Tyr Asn Tyr Asn Ser His Asn Val Tyr Ile Met Ala Asp Lys Gln Lys
145                 150                 155                 160

Asn Gly Ile Lys Val Asn Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
210                 215                 220

Phe Val Thr Ala Ala Gly Ile Thr Leu Gly Met Asp Glu Leu Tyr Lys
225                 230                 235                 240

Leu Ile Asn

<210> SEQ ID NO 45
<211> LENGTH: 307
<212> TYPE: PRT
<213> ORGANISM: Artificial Sequence
<220> FEATURE:
<223> OTHER INFORMATION: Fusion protein

<400> SEQUENCE: 45

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys Leu Glu Ala Leu Phe Gln
        50                  55                  60

Gly Pro Asn Ser Lys Gly Glu Glu Leu Phe Thr Gly Val Val Pro Ile
65                  70                  75                  80

Leu Val Glu Leu Asp Gly Asp Val Asn Gly His Lys Phe Ser Val Ser
                85                  90                  95

Gly Glu Gly Glu Gly Asp Ala Thr Tyr Gly Lys Leu Thr Leu Lys Phe
            100                 105                 110

Ile Cys Thr Thr Gly Lys Leu Pro Val Pro Trp Pro Thr Leu Val Thr
        115                 120                 125

Thr Leu Thr Tyr Gly Val Gln Cys Phe Ser Arg Tyr Pro Asp His Met
        130                 135                 140

Lys Gln His Asp Phe Phe Lys Ser Ala Met Pro Glu Gly Tyr Val Gln
145                 150                 155                 160

Glu Arg Thr Ile Phe Phe Lys Asp Asp Gly Asn Tyr Lys Thr Arg Ala
                165                 170                 175

Glu Val Lys Phe Glu Gly Asp Thr Leu Val Asn Arg Ile Glu Leu Lys
            180                 185                 190

Gly Ile Asp Phe Lys Glu Asp Gly Asn Ile Leu Gly His Lys Leu Glu
        195                 200                 205
```

```
Tyr Asn Tyr Asn Ser His Asn Val Tyr Ile Met Ala Asp Lys Gln Lys
            210                 215                 220

Asn Gly Ile Lys Val Asn Phe Lys Ile Arg His Asn Ile Glu Asp Gly
225                 230                 235                 240

Ser Val Gln Leu Ala Asp His Tyr Gln Gln Asn Thr Pro Ile Gly Asp
            245                 250                 255

Gly Pro Val Leu Leu Pro Asp Asn His Tyr Leu Ser Thr Gln Ser Ala
            260                 265                 270

Leu Ser Lys Asp Pro Asn Glu Lys Arg Asp His Met Val Leu Leu Glu
            275                 280                 285

Phe Val Thr Ala Ala Gly Ile Thr Leu Gly Met Asp Glu Leu Tyr Lys
            290                 295                 300

Leu Ile Asn
305

<210> SEQ ID NO 46
<211> LENGTH: 368
<212> TYPE: PRT
<213> ORGANISM: Artificial Sequence
<220> FEATURE:
<223> OTHER INFORMATION: Fusion protein

<400> SEQUENCE: 46

His His His His His His Leu Ala Glu Ala Lys Val Leu Ala Asn Arg
1               5                   10                  15

Glu Leu Asp Lys Tyr Gly Val Ser Asp Tyr His Lys Asn Leu Ile Asn
            20                  25                  30

Asn Ala Lys Thr Val Glu Gly Val Lys Asp Leu Gln Ala Gln Val Val
            35                  40                  45

Glu Ser Ala Lys Lys Ala Arg Ile Ser Glu Ala Thr Asp Gly Leu Ser
50                  55                  60

Asp Phe Leu Lys Ser Gln Thr Pro Ala Glu Asp Thr Val Lys Ser Ile
65                  70                  75                  80

Glu Leu Ala Glu Ala Lys Val Leu Ala Asn Arg Glu Leu Asp Lys Tyr
            85                  90                  95

Gly Val Ser Asp Tyr Tyr Lys Asn Leu Ile Asn Asn Ala Lys Thr Val
            100                 105                 110

Glu Gly Val Lys Ala Leu Ile Asp Glu Ile Leu Ala Ala Leu Pro Asn
            115                 120                 125

Ser Lys Gly Glu Glu Leu Phe Thr Gly Val Val Pro Ile Leu Val Glu
130                 135                 140

Leu Asp Gly Asp Val Asn Gly His Lys Phe Ser Val Ser Gly Glu Gly
145                 150                 155                 160

Glu Gly Asp Ala Thr Tyr Gly Lys Leu Thr Leu Lys Phe Ile Cys Thr
            165                 170                 175

Thr Gly Lys Leu Pro Val Pro Trp Pro Thr Leu Val Thr Thr Leu Thr
            180                 185                 190

Tyr Gly Val Gln Cys Phe Ser Arg Tyr Pro Asp His Met Lys Gln His
            195                 200                 205

Asp Phe Phe Lys Ser Ala Met Pro Glu Gly Tyr Val Gln Glu Arg Thr
            210                 215                 220

Ile Phe Phe Lys Asp Asp Gly Asn Tyr Lys Thr Arg Ala Glu Val Lys
225                 230                 235                 240

Phe Glu Gly Asp Thr Leu Val Asn Arg Ile Glu Leu Lys Gly Ile Asp
            245                 250                 255
```

```
Phe Lys Glu Asp Gly Asn Ile Leu Gly His Lys Leu Glu Tyr Asn Tyr
            260                 265                 270

Asn Ser His Asn Val Tyr Ile Met Ala Asp Lys Gln Lys Asn Gly Ile
        275                 280                 285

Lys Val Asn Phe Lys Ile Arg His Asn Ile Glu Asp Gly Ser Val Gln
    290                 295                 300

Leu Ala Asp His Tyr Gln Gln Asn Thr Pro Ile Gly Asp Gly Pro Val
305                 310                 315                 320

Leu Leu Pro Asp Asn His Tyr Leu Ser Thr Gln Ser Ala Leu Ser Lys
                325                 330                 335

Asp Pro Asn Glu Lys Arg Asp His Met Val Leu Leu Glu Phe Val Thr
                340                 345                 350

Ala Ala Gly Ile Thr Leu Gly Met Asp Glu Leu Tyr Lys Leu Ile Asn
            355                 360                 365
```

<210> SEQ ID NO 47
<211> LENGTH: 692
<212> TYPE: PRT
<213> ORGANISM: Artificial Sequence
<220> FEATURE:
<223> OTHER INFORMATION: Fusion protein

<400> SEQUENCE: 47

```
Met Gly His His His His His Gly Gly Gly Ser Gly Gly Gly
1               5                   10                  15

Gly Ser His His His His His Met Ser His Thr Thr Pro Trp Thr
            20                  25                  30

Asn Pro Gly Leu Ala Glu Asn Phe Met Asn Ser Phe Met Gln Gly Leu
        35                  40                  45

Ser Ser Met Pro Gly Phe Thr Ala Ser Gln Leu Asp Asp Met Ser Thr
    50                  55                  60

Ile Ala Gln Ser Met Val Gln Ser Ile Gln Ser Leu Ala Ala Gln Gly
65                  70                  75                  80

Arg Thr Ser Pro Asn Lys Leu Gln Ala Leu Asn Met Ala Phe Ala Ser
                85                  90                  95

Ser Met Ala Glu Ile Ala Ala Ser Glu Glu Gly Gly Gly Ser Leu Ser
            100                 105                 110

Thr Lys Thr Ser Ser Ile Ala Ser Ala Met Ser Asn Ala Phe Leu Gln
        115                 120                 125

Thr Thr Gly Val Val Asn Gln Pro Phe Ile Asn Glu Ile Thr Gln Leu
    130                 135                 140

Val Ser Met Phe Ala Gln Ala Gly Met Asn Asp Gly Gly Gly Thr Pro
145                 150                 155                 160

Trp Thr Asn Pro Gly Leu Ala Glu Asn Phe Met Asn Ser Phe Met Gln
                165                 170                 175

Gly Leu Ser Ser Met Pro Gly Phe Thr Ala Ser Gln Leu Asp Asp Met
            180                 185                 190

Ser Thr Ile Ala Gln Ser Met Val Gln Ser Ile Gln Ser Leu Ala Ala
        195                 200                 205

Gln Gly Arg Thr Ser Pro Asn Lys Leu Gln Ala Leu Asn Met Ala Phe
    210                 215                 220

Ala Ser Ser Met Ala Glu Ile Ala Ala Ser Glu Glu Gly Gly Gly Ser
225                 230                 235                 240

Leu Ser Thr Lys Thr Ser Ser Ile Ala Ser Ala Met Ser Asn Ala Phe
                245                 250                 255
```

```
Leu Gln Thr Thr Gly Val Val Asn Gln Pro Phe Ile Asn Glu Ile Thr
            260                 265                 270
Gln Leu Val Ser Met Phe Ala Gln Ala Gly Met Asn Asp Val Ser Ala
            275                 280                 285
Leu Glu Ala Leu Phe Gln Gly Pro Asn Ser Thr Gly Ala Thr Ser Pro
            290                 295                 300
Glu Glu Ala Ile Ala Asp Leu Ser Val Asn Met Tyr Asn Arg Leu Arg
305                 310                 315                 320
Ala Thr Gly Glu Asp Glu Asn Ile Leu Phe Ser Pro Leu Ser Ile Ala
            325                 330                 335
Leu Ala Met Gly Met Met Glu Leu Gly Ala Gln Gly Ser Thr Gln Lys
            340                 345                 350
Glu Ile Arg His Ser Met Gly Tyr Asp Ser Leu Lys Asn Gly Glu Glu
            355                 360                 365
Phe Ser Phe Leu Lys Glu Phe Ser Asn Met Val Thr Ala Lys Glu Ser
    370                 375                 380
Gln Tyr Val Met Lys Ile Ala Asn Ser Leu Phe Val Gln Asn Gly Phe
385                 390                 395                 400
His Val Asn Glu Glu Phe Leu Gln Met Met Lys Lys Tyr Phe Asn Ala
            405                 410                 415
Ala Val Asn His Val Asp Phe Ser Gln Asn Val Ala Val Ala Asn Tyr
            420                 425                 430
Ile Asn Lys Trp Val Glu Asn Thr Asn Asn Leu Val Lys Asp Leu
            435                 440                 445
Val Ser Pro Arg Asp Phe Asp Ala Ala Thr Tyr Leu Ala Leu Ile Asn
            450                 455                 460
Ala Val Tyr Phe Lys Gly Asn Trp Lys Ser Gln Phe Arg Pro Glu Asn
465                 470                 475                 480
Thr Arg Thr Phe Ser Phe Thr Lys Asp Asp Glu Ser Glu Val Gln Ile
            485                 490                 495
Pro Met Met Tyr Gln Gln Gly Glu Phe Tyr Tyr Gly Glu Phe Ser Asp
            500                 505                 510
Gly Ser Asn Glu Ala Gly Gly Ile Tyr Gln Val Leu Glu Ile Pro Tyr
            515                 520                 525
Glu Gly Asp Glu Ile Ser Met Met Leu Val Leu Ser Arg Gln Glu Val
            530                 535                 540
Pro Leu Ala Thr Leu Glu Pro Leu Val Lys Ala Gln Leu Val Glu Glu
545                 550                 555                 560
Trp Ala Asn Ser Val Lys Lys Gln Lys Val Glu Val Tyr Leu Pro Arg
            565                 570                 575
Phe Thr Val Glu Gln Glu Ile Asp Leu Lys Asp Val Leu Lys Ala Leu
            580                 585                 590
Gly Ile Thr Glu Ile Phe Ile Lys Asp Ala Asn Leu Thr Gly Leu Ser
            595                 600                 605
Asp Asn Lys Glu Ile Phe Leu Ser Lys Ala Ile His Lys Ser Phe Leu
            610                 615                 620
Glu Val Asn Glu Glu Gly Ser Glu Ala Ala Val Ser Gly Met Ile
625                 630                 635                 640
Ala Ile Ser Arg Met Ala Val Leu Tyr Pro Gln Val Ile Val Asp His
            645                 650                 655
Pro Phe Phe Phe Leu Ile Arg Asn Arg Arg Thr Gly Thr Ile Leu Phe
            660                 665                 670
```

Met Gly Arg Val Met His Pro Glu Thr Met Asn Thr Ser Gly His Asp
            675                 680                 685

Phe Glu Glu Leu
    690

<210> SEQ ID NO 48
<211> LENGTH: 2085
<212> TYPE: DNA
<213> ORGANISM: Artificial Sequence
<220> FEATURE:
<223> OTHER INFORMATION: Fusion protein

<400> SEQUENCE: 48

| | | |
|---|---|---|
| atgggccatc atcatcatca tcatggcggc ggtggtagcg gtggcggtgg cagccatcat | 60 |
| catcatcatc atatgagcca taccaccccg tggaccaacc cgggcctggc ggaaaacttt | 120 |
| atgaacagct ttatgcaggg cctgagcagc atgccgggct taccgcgag ccagctggat | 180 |
| gatatgagca ccattgcgca gagcatggtg cagagcattc agagcctggc ggcgcagggc | 240 |
| cgtaccagcc cgaacaaact gcaggcgctg aacatggcgt ttgcgagcag catggcggaa | 300 |
| attgcggcga gcgaagaagg cggcggcagc ctgagcacca aaccagcag cattgcgagc | 360 |
| gcgatgagca acgcgtttct gcagaccacc ggcgtggtga accagccgtt tattaacgaa | 420 |
| attacccagc tggtgagcat gtttgcgcag gcgggcatga cgatggcgg cggcaccccg | 480 |
| tggaccaacc cgggcctggc ggaaaacttt atgaacagct ttatgcaggg cctgagcagc | 540 |
| atgccgggct taccgcgag ccagctggat gatatgagca ccattgcgca gagcatggtg | 600 |
| cagagcattc agagcctggc ggcgcagggc cgtaccagcc cgaacaaact gcaggcgctg | 660 |
| aacatggcgt ttgcgagcag catggcggaa attgcggcga gcgaagaagg cggcggcagc | 720 |
| ctgagcacca aaccagcag cattgcgagc gcgatgagca acgcgtttct gcagaccacc | 780 |
| ggcgtggtga accagccgtt tattaacgaa attacccagc tggtgagcat gtttgcgcag | 840 |
| gcgggcatga cgatgtgag cgcgctggaa gcgctgttcc agggcccgaa ttcaacaggg | 900 |
| gccacttccc ctgaggaagc cattgctgac ttgtcagtga atatgtataa tcgtcttaga | 960 |
| gccactggtg aagatgaaaa tattctcttc tctccattga gtattgctct gcaatgggga | 1020 |
| atgatggaac ttggggccca aggatctacc agaaagaaa tccgccactc aatgggatat | 1080 |
| gacagcctaa aaaatggtga agaatttct ttcttgaagg agttttcaaa catggtaact | 1140 |
| gctaaagaga gccaatatgt gatgaaaatt gccaattcct gtttgtgca aaatggattt | 1200 |
| catgtcaatg aggagttttt gcaaatgatg aaaaaatatt ttaatgcagc agtaaatcat | 1260 |
| gtggacttca gtcaaaatgt agccgtggcc aactacatca taagtgggt ggagaataac | 1320 |
| acaaacaatc tggtgaaaga tttggtatcc caagggatt tgatgctgc cacttatctg | 1380 |
| gccctcatta atgctgtcta tttcaagggg aactggaagt cgcagtttag gcctgaaaat | 1440 |
| actagaacct tttctttcac taaagatgat gaaagtgaag tccaaattcc aatgatgtat | 1500 |
| cagcaaggag aatttttatta tggggaattt agtgatggct ccaatgaagc tggtggtatc | 1560 |
| taccaagtcc tagaaatacc atatgaagga gatgaaataa gcatgatgct ggtgctgtcc | 1620 |
| agacaggaag ttcctcttgc tactctggag ccattagtca aagcacagct ggttgaagaa | 1680 |
| tgggcaaact ctgtgaagaa gcaaaaagta gaagtatacc tgcccaggtt cacagtggaa | 1740 |
| caggaaattg attaaaaga tgttttgaag gctcttggaa taactgaaat tttcatcaaa | 1800 |
| gatgcaaatt tgacaggcct ctctgataat aaggagattt ttctttccaa agcaattcac | 1860 |
| aagtccttcc tagaggttaa tgaagaaggc tcagaagctg ctgctgtctc aggaatgatt | 1920 |

```
gcaattagta ggatggctgt gctgtatcct caagttattg tcgaccatcc attttctttt    1980
cttatcagaa acaggagaac tggtacaatt ctattcatgg gacgagtcat gcatcctgaa    2040
acaatgaaca caagtggaca tgatttcgaa gaactttaat gataa                    2085
```

<210> SEQ ID NO 49
<211> LENGTH: 398
<212> TYPE: PRT
<213> ORGANISM: Homo sapiens

<400> SEQUENCE: 49

```
Gly Pro Asn Ser Thr Gly Ala Thr Ser Pro Glu Glu Ala Ile Ala Asp
1               5                   10                  15

Leu Ser Val Asn Met Tyr Asn Arg Leu Arg Ala Thr Gly Glu Asp Glu
            20                  25                  30

Asn Ile Leu Phe Ser Pro Leu Ser Ile Ala Leu Ala Met Gly Met Met
        35                  40                  45

Glu Leu Gly Ala Gln Gly Ser Thr Gln Lys Glu Ile Arg His Ser Met
    50                  55                  60

Gly Tyr Asp Ser Leu Lys Asn Gly Glu Glu Phe Ser Phe Leu Lys Glu
65                  70                  75                  80

Phe Ser Asn Met Val Thr Ala Lys Glu Ser Gln Tyr Val Met Lys Ile
                85                  90                  95

Ala Asn Ser Leu Phe Val Gln Asn Gly Phe His Val Asn Glu Glu Phe
            100                 105                 110

Leu Gln Met Met Lys Lys Tyr Phe Asn Ala Ala Val Asn His Val Asp
        115                 120                 125

Phe Ser Gln Asn Val Ala Val Ala Asn Tyr Ile Asn Lys Trp Val Glu
    130                 135                 140

Asn Asn Thr Asn Asn Leu Val Lys Asp Leu Val Ser Pro Arg Asp Phe
145                 150                 155                 160

Asp Ala Ala Thr Tyr Leu Ala Leu Ile Asn Ala Val Tyr Phe Lys Gly
                165                 170                 175

Asn Trp Lys Ser Gln Phe Arg Pro Glu Asn Thr Arg Thr Phe Ser Phe
            180                 185                 190

Thr Lys Asp Asp Glu Ser Glu Val Gln Ile Pro Met Met Tyr Gln Gln
        195                 200                 205

Gly Glu Phe Tyr Tyr Gly Glu Phe Ser Asp Gly Ser Asn Glu Ala Gly
    210                 215                 220

Gly Ile Tyr Gln Val Leu Glu Ile Pro Tyr Glu Gly Asp Glu Ile Ser
225                 230                 235                 240

Met Met Leu Val Leu Ser Arg Gln Glu Val Pro Leu Ala Thr Leu Glu
                245                 250                 255

Pro Leu Val Lys Ala Gln Leu Val Glu Glu Trp Ala Asn Ser Val Lys
            260                 265                 270

Lys Gln Lys Val Glu Val Tyr Leu Pro Arg Phe Thr Val Glu Gln Glu
        275                 280                 285

Ile Asp Leu Lys Asp Val Leu Lys Ala Leu Gly Ile Thr Glu Ile Phe
    290                 295                 300

Ile Lys Asp Ala Asn Leu Thr Gly Leu Ser Asp Asn Lys Glu Ile Phe
305                 310                 315                 320

Leu Ser Lys Ala Ile His Lys Ser Phe Leu Glu Val Asn Glu Glu Gly
                325                 330                 335

Ser Glu Ala Ala Ala Val Ser Gly Met Ile Ala Ile Ser Arg Met Ala
```

```
                340                 345                 350
Val Leu Tyr Pro Gln Val Ile Val Asp His Pro Phe Phe Phe Leu Ile
            355                 360                 365

Arg Asn Arg Arg Thr Gly Thr Ile Leu Phe Met Gly Arg Val Met His
370                 375                 380

Pro Glu Thr Met Asn Thr Ser Gly His Asp Phe Glu Glu Leu
385                 390                 395

<210> SEQ ID NO 50
<211> LENGTH: 131
<212> TYPE: PRT
<213> ORGANISM: Euprosthenops australis

<400> SEQUENCE: 50

Ser His Thr Thr Pro Trp Thr Asn Pro Gly Leu Ala Glu Asn Phe Met
1               5                   10                  15

Asn Ser Phe Met Gln Gly Leu Ser Ser Met Pro Gly Phe Thr Ala Ser
                20                  25                  30

Gln Leu Asp Asp Met Ser Thr Ile Ala Gln Ser Met Val Gln Ser Ile
            35                  40                  45

Gln Ser Leu Ala Ala Gln Gly Arg Thr Ser Pro Asn Lys Leu Gln Ala
    50                  55                  60

Leu Asn Met Ala Phe Ala Ser Ser Met Ala Glu Ile Ala Ala Ser Glu
65                  70                  75                  80

Glu Gly Gly Gly Ser Leu Ser Thr Lys Thr Ser Ser Ile Ala Ser Ala
                85                  90                  95

Met Ser Asn Ala Phe Leu Gln Thr Thr Gly Val Val Asn Gln Pro Phe
                100                 105                 110

Ile Asn Glu Ile Thr Gln Leu Val Ser Met Phe Ala Gln Ala Gly Met
            115                 120                 125

Asn Asp Val
    130

<210> SEQ ID NO 51
<211> LENGTH: 127
<212> TYPE: PRT
<213> ORGANISM: Latrodectus geometricus

<400> SEQUENCE: 51

Gln Ala Asn Thr Pro Trp Ser Ser Lys Gln Asn Ala Asp Ala Phe Ile
1               5                   10                  15

Ser Ala Phe Met Thr Ala Ala Ser Gln Ser Gly Ala Phe Ser Ser Asp
                20                  25                  30

Gln Ile Asp Asp Met Ser Val Ile Ser Asn Thr Leu Met Ala Ala Met
            35                  40                  45

Asp Asn Met Gly Gly Arg Ile Thr Pro Ser Lys Leu Gln Ala Leu Asp
    50                  55                  60

Met Ala Phe Ala Ser Ser Val Ala Glu Ile Ala Ala Val Glu Gly Gln
65                  70                  75                  80

Asn Ile Gly Val Thr Thr Asn Ala Ile Ser Asp Ala Leu Thr Ser Ala
                85                  90                  95

Phe Tyr Gln Thr Thr Gly Val Val Asn Asn Lys Phe Ile Ser Glu Ile
                100                 105                 110

Arg Ser Leu Ile Asn Met Phe Ala Gln Ala Ser Ala Asn Asp Val
            115                 120                 125
```

<210> SEQ ID NO 52
<211> LENGTH: 127
<212> TYPE: PRT
<213> ORGANISM: Latrodectus hesperus

<400> SEQUENCE: 52

Gln Ala Asn Thr Pro Trp Ser Ser Lys Ala Asn Ala Asp Ala Phe Ile
1               5                   10                  15

Asn Ser Phe Ile Ser Ala Ala Ser Asn Thr Gly Ser Phe Ser Gln Asp
            20                  25                  30

Gln Met Glu Asp Met Ser Leu Ile Gly Asn Thr Leu Met Ala Ala Met
        35                  40                  45

Asp Asn Met Gly Gly Arg Ile Thr Pro Ser Lys Leu Gln Ala Leu Asp
50                  55                  60

Met Ala Phe Ala Ser Ser Val Ala Glu Ile Ala Ala Ser Glu Gly Gly
65                  70                  75                  80

Asp Leu Gly Val Thr Thr Asn Ala Ile Ala Asp Ala Leu Thr Ser Ala
                85                  90                  95

Phe Tyr Gln Thr Thr Gly Val Val Asn Ser Arg Phe Ile Ser Glu Ile
            100                 105                 110

Arg Ser Leu Ile Gly Met Phe Ala Gln Ala Ser Ala Asn Asp Val
        115                 120                 125

<210> SEQ ID NO 53
<211> LENGTH: 130
<212> TYPE: PRT
<213> ORGANISM: Nephila clavipes

<400> SEQUENCE: 53

Gln Asn Thr Pro Trp Ser Ser Thr Glu Leu Ala Asp Ala Phe Ile Asn
1               5                   10                  15

Ala Phe Met Asn Glu Ala Gly Arg Thr Gly Ala Phe Thr Ala Asp Gln
            20                  25                  30

Leu Asp Asp Met Ser Thr Ile Gly Asp Thr Ile Lys Thr Ala Met Asp
        35                  40                  45

Lys Met Ala Arg Ser Asn Lys Ser Ser Lys Gly Lys Leu Gln Ala Leu
50                  55                  60

Asn Met Ala Phe Ala Ser Ser Met Ala Glu Ile Ala Ala Val Glu Gln
65                  70                  75                  80

Gly Gly Leu Ser Val Asp Ala Lys Thr Asn Ala Ile Ala Asp Ser Leu
                85                  90                  95

Asn Ser Ala Phe Tyr Gln Thr Thr Gly Ala Ala Asn Pro Gln Phe Val
            100                 105                 110

Asn Glu Ile Arg Ser Leu Ile Asn Met Phe Ala Gln Ser Ser Ala Asn
        115                 120                 125

Glu Val
130

<210> SEQ ID NO 54
<211> LENGTH: 131
<212> TYPE: PRT
<213> ORGANISM: Argiope trifasciata

<400> SEQUENCE: 54

Gln Gly Ala Thr Pro Trp Glu Asn Ser Gln Leu Ala Glu Ser Phe Ile
1               5                   10                  15

Ser Arg Phe Leu Arg Phe Ile Gly Gln Ser Gly Ala Phe Ser Pro Asn
            20                  25                  30

```
Gln Leu Asp Asp Met Ser Ser Ile Gly Asp Thr Leu Lys Thr Ala Ile
            35                  40                  45

Glu Lys Met Ala Gln Ser Arg Lys Ser Ser Lys Ser Lys Leu Gln Ala
 50                  55                  60

Leu Asn Met Ala Phe Ala Ser Ser Met Ala Glu Ile Ala Val Ala Glu
 65                  70                  75                  80

Gln Gly Gly Leu Ser Leu Glu Ala Lys Thr Asn Ala Ile Ala Ser Ala
                85                  90                  95

Leu Ser Ala Ala Phe Leu Glu Thr Thr Gly Tyr Val Asn Gln Gln Phe
                100                 105                 110

Val Asn Glu Ile Lys Thr Leu Ile Phe Met Ile Ala Gln Ala Ser Ser
                115                 120                 125

Asn Glu Ile
        130

<210> SEQ ID NO 55
<211> LENGTH: 124
<212> TYPE: PRT
<213> ORGANISM: Latrodectus geometricus

<400> SEQUENCE: 55

Leu Arg Trp Ser Ser Lys Asp Asn Ala Asp Arg Phe Ile Asn Ala Phe
 1               5                  10                  15

Leu Gln Ala Ala Ser Asn Ser Gly Ala Phe Ser Ser Asp Gln Val Asp
                20                  25                  30

Asp Met Ser Val Ile Gly Asn Thr Leu Met Thr Ala Met Asp Asn Met
            35                  40                  45

Gly Gly Arg Ile Thr Pro Ser Lys Leu Gln Ala Leu Asp Met Ala Phe
 50                  55                  60

Ala Ser Ser Val Ala Glu Ile Ala Val Ala Asp Gly Gln Asn Val Gly
 65                  70                  75                  80

Gly Ala Thr Asn Ala Ile Ser Asn Ala Leu Arg Ser Ala Phe Tyr Gln
                85                  90                  95

Thr Thr Gly Val Val Asn Asn Gln Phe Ile Ser Glu Ile Ser Asn Leu
                100                 105                 110

Ile Asn Met Phe Ala Gln Val Ser Ala Asn Glu Val
        115                 120

<210> SEQ ID NO 56
<211> LENGTH: 127
<212> TYPE: PRT
<213> ORGANISM: Latrodectus hesperus

<400> SEQUENCE: 56

Gln Ala Asn Thr Pro Trp Ser Ser Lys Glu Asn Ala Asp Ala Phe Ile
 1               5                  10                  15

Gly Ala Phe Met Asn Ala Ala Ser Gln Ser Gly Ala Phe Ser Ser Asp
                20                  25                  30

Gln Ile Asp Asp Met Ser Val Ile Ser Asn Thr Leu Met Ala Ala Met
            35                  40                  45

Asp Asn Met Gly Gly Arg Ile Thr Gln Ser Lys Leu Gln Ala Leu Asp
 50                  55                  60

Met Ala Phe Ala Ser Ser Val Ala Glu Ile Ala Val Ala Asp Gly Gln
 65                  70                  75                  80

Asn Val Gly Ala Ala Thr Asn Ala Ile Ser Asp Ala Leu Arg Ser Ala
                85                  90                  95
```

```
Phe Tyr Gln Thr Thr Gly Val Val Asn Asn Gln Phe Ile Thr Gly Ile
            100                 105                 110

Ser Ser Leu Ile Gly Met Phe Ala Gln Val Ser Gly Asn Glu Val
        115                 120                 125

<210> SEQ ID NO 57
<211> LENGTH: 131
<212> TYPE: PRT
<213> ORGANISM: Nephila inaurata madagascariensis

<400> SEQUENCE: 57

Gln Ala Asn Thr Pro Trp Ser Asp Thr Ala Thr Ala Asp Ala Phe Ile
1               5                   10                  15

Gln Asn Phe Leu Gly Ala Val Ser Gly Ser Gly Ala Phe Thr Pro Asp
            20                  25                  30

Gln Leu Asp Asp Met Ser Thr Val Gly Asp Thr Ile Met Ser Ala Met
        35                  40                  45

Asp Lys Met Ala Arg Ser Asn Lys Ser Ser Lys Ser Lys Leu Gln Ala
50                  55                  60

Leu Asn Met Ala Phe Ala Ser Ser Met Ala Glu Ile Ala Ala Val Glu
65                  70                  75                  80

Gln Gly Gly Gln Ser Met Asp Val Lys Thr Asn Ala Ile Ala Asn Ala
                85                  90                  95

Leu Asp Ser Ala Phe Tyr Met Thr Thr Gly Ser Thr Asn Gln Gln Phe
            100                 105                 110

Val Asn Glu Met Arg Ser Leu Ile Asn Met Leu Ser Ala Ala Ala Val
        115                 120                 125

Asn Glu Val
    130

<210> SEQ ID NO 58
<211> LENGTH: 131
<212> TYPE: PRT
<213> ORGANISM: Nephila clavipes

<400> SEQUENCE: 58

Gln Ala Arg Ser Pro Trp Ser Asp Thr Ala Thr Ala Asp Ala Phe Ile
1               5                   10                  15

Gln Asn Phe Leu Ala Ala Val Ser Gly Ser Gly Ala Phe Thr Ser Asp
            20                  25                  30

Gln Leu Asp Asp Met Ser Thr Ile Gly Asp Thr Ile Met Ser Ala Met
        35                  40                  45

Asp Lys Met Ala Arg Ser Asn Lys Ser Ser Gln His Lys Leu Gln Ala
50                  55                  60

Leu Asn Met Ala Phe Ala Ser Ser Met Ala Glu Ile Ala Ala Val Glu
65                  70                  75                  80

Gln Gly Gly Met Ser Met Ala Val Lys Thr Asn Ala Ile Val Asp Gly
                85                  90                  95

Leu Asn Ser Ala Phe Tyr Met Thr Thr Gly Ala Ala Asn Pro Gln Phe
            100                 105                 110

Val Asn Glu Met Arg Ser Leu Ile Ser Met Ile Ser Ala Ala Ser Ala
        115                 120                 125

Asn Glu Val
    130

<210> SEQ ID NO 59
```

<211> LENGTH: 129
<212> TYPE: PRT
<213> ORGANISM: Argiope bruennichi

<400> SEQUENCE: 59

Ala Val Pro Ser Val Phe Ser Ser Pro Asn Leu Ala Ser Gly Phe Leu
1               5                   10                  15
Gln Cys Leu Thr Phe Gly Ile Gly Asn Ser Pro Ala Phe Pro Thr Gln
            20                  25                  30
Glu Gln Gln Asp Leu Asp Ala Ile Ala Gln Val Ile Leu Asn Ala Val
        35                  40                  45
Ser Ser Asn Thr Gly Ala Thr Ala Ser Ala Arg Ala Gln Ala Leu Ser
    50                  55                  60
Thr Ala Leu Ala Ser Ser Leu Thr Asp Leu Leu Ile Ala Glu Ser Ala
65                  70                  75                  80
Glu Ser Asn Tyr Ser Asn Gln Leu Ser Glu Leu Thr Gly Ile Leu Ser
                85                  90                  95
Asp Cys Phe Ile Gln Thr Thr Gly Ser Asp Pro Ala Phe Val Ser
            100                 105                 110
Arg Ile Gln Ser Leu Ile Ser Val Leu Ser Gln Asn Ala Asp Thr Asn
        115                 120                 125
Ile

<210> SEQ ID NO 60
<211> LENGTH: 129
<212> TYPE: PRT
<213> ORGANISM: Nephila clavata

<400> SEQUENCE: 60

Pro Val Pro Ser Val Phe Ser Ser Pro Ser Leu Ala Ser Gly Phe Leu
1               5                   10                  15
Gly Cys Leu Thr Thr Gly Ile Gly Leu Ser Pro Ala Phe Pro Phe Gln
            20                  25                  30
Glu Gln Gln Asp Leu Asp Asp Leu Ala Lys Val Ile Leu Ser Ala Val
        35                  40                  45
Thr Ser Asn Thr Asp Thr Ser Lys Ser Ala Arg Ala Gln Ala Leu Ser
    50                  55                  60
Thr Ala Leu Ala Ser Ser Leu Ala Asp Leu Leu Ile Ser Glu Ser Ser
65                  70                  75                  80
Gly Ser Ser Tyr Gln Thr Gln Ile Ser Ala Leu Thr Asn Ile Leu Ser
                85                  90                  95
Asp Cys Phe Val Thr Thr Thr Gly Ser Asn Asn Pro Ala Phe Val Ser
            100                 105                 110
Arg Val Gln Thr Leu Ile Gly Val Leu Ser Gln Ser Ser Asn Ala
        115                 120                 125
Ile

<210> SEQ ID NO 61
<211> LENGTH: 128
<212> TYPE: PRT
<213> ORGANISM: Latrodectus hesperus

<400> SEQUENCE: 61

Ala Ser Val Asn Ile Phe Asn Ser Pro Asn Ala Ala Thr Ser Phe Leu
1               5                   10                  15
Asn Cys Leu Arg Ser Asn Ile Glu Ser Ser Pro Ala Phe Pro Phe Gln
            20                  25                  30

-continued

Glu Gln Ala Asp Leu Asp Ser Ile Ala Glu Val Ile Leu Ser Asp Val
         35                  40                  45

Ser Ser Val Asn Thr Ala Ser Ser Ala Thr Ser Leu Ala Leu Ser Thr
 50                  55                  60

Ala Leu Ala Ser Ser Leu Ala Glu Leu Leu Val Thr Glu Ser Ala Glu
 65                  70                  75                  80

Glu Asp Ile Asp Asn Gln Val Val Ala Leu Ser Thr Ile Leu Ser Gln
                 85                  90                  95

Cys Phe Val Glu Thr Thr Gly Ser Pro Asn Pro Ala Phe Val Ala Ser
                100                 105                 110

Val Lys Ser Leu Leu Gly Val Leu Ser Gln Ser Ala Ser Asn Tyr Glu
             115                 120                 125

<210> SEQ ID NO 62
<211> LENGTH: 130
<212> TYPE: PRT
<213> ORGANISM: Nephila clavipes

<400> SEQUENCE: 62

Ile Ala Asn Ser Pro Phe Ser Asn Pro Asn Thr Ala Glu Ala Phe Ala
 1               5                  10                  15

Arg Ser Phe Val Ser Asn Ile Val Ser Ser Gly Glu Phe Gly Ala Gln
             20                  25                  30

Gly Ala Glu Asp Phe Asp Asp Ile Ile Gln Ser Leu Ile Gln Ala Gln
         35                  40                  45

Ser Met Gly Lys Gly Arg His Asp Thr Lys Ala Lys Ala Lys Ala Met
 50                  55                  60

Gln Val Ala Leu Ala Ser Ser Ile Ala Glu Leu Val Ile Ala Glu Ser
 65                  70                  75                  80

Ser Gly Gly Asp Val Gln Arg Lys Thr Asn Val Ile Ser Asn Ala Leu
                 85                  90                  95

Arg Asn Ala Leu Met Ser Thr Thr Gly Ser Pro Asn Glu Glu Phe Val
                100                 105                 110

His Glu Val Gln Asp Leu Ile Gln Met Leu Ser Gln Glu Gln Ile Asn
             115                 120                 125

Glu Val
 130

<210> SEQ ID NO 63
<211> LENGTH: 130
<212> TYPE: PRT
<213> ORGANISM: Nephila inaurata madagascariensis

<400> SEQUENCE: 63

Ile Val Asn Ser Pro Phe Ser Asn Pro Asn Thr Ala Glu Ala Phe Ala
 1               5                  10                  15

Arg Ser Phe Val Ser Asn Val Val Ser Ser Gly Glu Phe Gly Ala Gln
             20                  25                  30

Gly Ala Glu Asp Phe Asp Asp Ile Ile Gln Ser Leu Ile Gln Ala Gln
         35                  40                  45

Ser Met Gly Lys Gly Arg His Asp Thr Lys Ala Lys Ala Lys Ala Met
 50                  55                  60

Gln Val Ala Leu Ala Ser Ser Ile Ala Glu Leu Val Ile Ala Glu Ser
 65                  70                  75                  80

Ser Gly Gly Asp Val Gln Arg Lys Thr Asn Val Ile Ser Asn Ala Leu
                 85                  90                  95

Arg Asn Ala Leu Met Ser Thr Thr Gly Ser Pro Asn Glu Glu Phe Val
            100                 105                 110

His Glu Val Gln Asp Leu Ile Gln Met Leu Ser Gln Glu Gln Ile Asn
        115                 120                 125

Glu Val
    130

<210> SEQ ID NO 64
<211> LENGTH: 18
<212> TYPE: PRT
<213> ORGANISM: Euprosthenops australis

<400> SEQUENCE: 64

Ala Ser Ala Ser Ala Ala Ala Ser Ala Ala Ser Thr Val Ala Asn Ser
1               5                   10                  15

Val Ser

<210> SEQ ID NO 65
<211> LENGTH: 8
<212> TYPE: PRT
<213> ORGANISM: Euprosthenops australis

<400> SEQUENCE: 65

Ala Ser Ala Ala Ser Ala Ala Ala
1               5

<210> SEQ ID NO 66
<211> LENGTH: 8
<212> TYPE: PRT
<213> ORGANISM: Euprosthenops australis

<400> SEQUENCE: 66

Gly Ser Ala Met Gly Gln Gly Ser
1               5

<210> SEQ ID NO 67
<211> LENGTH: 5
<212> TYPE: PRT
<213> ORGANISM: Euprosthenops australis

<400> SEQUENCE: 67

Ser Ala Ser Ala Gly
1               5

<210> SEQ ID NO 68
<211> LENGTH: 100
<212> TYPE: PRT
<213> ORGANISM: Euprosthenops sp

<400> SEQUENCE: 68

Ser Arg Leu Ser Ser Pro Glu Ala Ser Ser Arg Val Ser Ser Ala Val
1               5                   10                  15

Ser Asn Leu Val Ser Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
        35                  40                  45

Ser Gly Cys Asp Val Leu Val Gln Ala Leu Leu Glu Val Val Ser Ala
    50                  55                  60

Leu Ile His Ile Leu Gly Ser Ser Ile Gly Gln Val Asn Tyr Gly
65                  70                  75                  80

```
Ser Ala Gly Gln Ala Thr Gln Leu Val Gly Gln Ser Val Tyr Gln Ala
                85                  90                  95
Leu Gly Glu Phe
            100

<210> SEQ ID NO 69
<211> LENGTH: 98
<212> TYPE: PRT
<213> ORGANISM: Euprosthenops australis

<400> SEQUENCE: 69

Ser Arg Leu Ser Ser Pro Ser Ala Val Ser Arg Val Ser Ser Ala Val
1               5                   10                  15

Ser Ser Leu Val Ser Asn Gly Gln Val Asn Met Ala Ala Leu Pro Asn
                20                  25                  30

Ile Ile Ser Asn Ile Ser Ser Val Ser Ala Ser Ala Pro Gly Ala
            35                  40                  45

Ser Gly Cys Glu Val Ile Val Gln Ala Leu Leu Glu Val Ile Thr Ala
    50                  55                  60

Leu Val Gln Ile Val Ser Ser Ser Val Gly Tyr Ile Asn Pro Ser
65                  70                  75                  80

Ala Val Asn Gln Ile Thr Asn Val Val Ala Asn Ala Met Ala Gln Val
                85                  90                  95

Met Gly

<210> SEQ ID NO 70
<211> LENGTH: 99
<212> TYPE: PRT
<213> ORGANISM: Argiope trifasciata

<400> SEQUENCE: 70

Ser Arg Leu Ser Ser Pro Gly Ala Ala Ser Arg Val Ser Ser Ala Val
1               5                   10                  15

Thr Ser Leu Val Ser Ser Gly Gly Pro Thr Asn Ser Ala Ala Leu Ser
                20                  25                  30

Asn Thr Ile Ser Asn Val Val Ser Gln Ile Ser Ser Ser Asn Pro Gly
            35                  40                  45

Leu Ser Gly Cys Asp Val Leu Val Gln Ala Leu Leu Glu Ile Val Ser
    50                  55                  60

Ala Leu Val His Ile Leu Gly Ser Ala Asn Ile Gly Gln Val Asn Ser
65                  70                  75                  80

Ser Gly Val Gly Arg Ser Ala Ser Ile Val Gly Gln Ser Ile Asn Gln
                85                  90                  95

Ala Phe Ser

<210> SEQ ID NO 71
<211> LENGTH: 89
<212> TYPE: PRT
<213> ORGANISM: Cyrtophora moluccensis

<400> SEQUENCE: 71

Ser His Leu Ser Ser Pro Glu Ala Ser Ser Arg Val Ser Ser Ala Val
1               5                   10                  15

Ser Asn Leu Val Ser Ser Gly Ser Thr Asn Ser Ala Ala Leu Pro Asn
                20                  25                  30

Thr Ile Ser Asn Val Val Ser Gln Ile Ser Ser Ser Asn Pro Gly Leu
            35                  40                  45
```

-continued

```
Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln Ile Val
                 85

<210> SEQ ID NO 72
<211> LENGTH: 98
<212> TYPE: PRT
<213> ORGANISM: Latrodectus geometricus

<400> SEQUENCE: 72

Ser Ala Leu Ala Ala Pro Ala Thr Ser Ala Arg Ile Ser Ser His Ala
 1               5                  10                  15

Ser Thr Leu Leu Ser Asn Gly Pro Thr Asn Pro Ala Ser Ile Ser Asn
                 20                  25                  30

Val Ile Ser Asn Ala Val Ser Gln Ile Ser Ser Asn Pro Gly Ala
             35                  40                  45

Ser Ser Cys Asp Val Leu Val Gln Ala Leu Leu Glu Leu Val Thr Ala
 50                  55                  60

Leu Leu Thr Ile Ile Gly Ser Ser Asn Val Gly Asn Val Asn Tyr Asp
 65                  70                  75                  80

Ser Ser Gly Gln Tyr Ala Gln Val Val Ser Gln Ser Val Gln Asn Ala
                 85                  90                  95

Phe Val

<210> SEQ ID NO 73
<211> LENGTH: 98
<212> TYPE: PRT
<213> ORGANISM: Latrodectus hesperus

<400> SEQUENCE: 73

Ser Ala Leu Ser Ala Pro Ala Thr Ser Ala Arg Ile Ser Ser His Ala
 1               5                  10                  15

Ser Ala Leu Leu Ser Ser Gly Pro Thr Asn Pro Ala Ser Ile Ser Asn
                 20                  25                  30

Val Ile Ser Asn Ala Val Ser Gln Ile Ser Ser Asn Pro Gly Ala
             35                  40                  45

Ser Ala Cys Asp Val Leu Val Gln Ala Leu Leu Glu Leu Val Thr Ala
 50                  55                  60

Leu Leu Thr Ile Ile Gly Ser Ser Asn Ile Gly Ser Val Asn Tyr Asp
 65                  70                  75                  80

Ser Ser Gly Gln Tyr Ala Gln Val Val Thr Gln Ser Val Gln Asn Val
                 85                  90                  95

Phe Gly

<210> SEQ ID NO 74
<211> LENGTH: 93
<212> TYPE: PRT
<213> ORGANISM: Macrothele holsti

<400> SEQUENCE: 74

Ser His Leu Ser Ser Pro Glu Ala Ser Ser Arg Val Ser Ser Ala Val
 1               5                  10                  15

Ser Asn Leu Val Ser Gly Gly Ser Thr Asn Ser Ala Ala Leu Pro Asn
                 20                  25                  30
```

-continued

```
Thr Ile Ser Asn Val Val Ser Gln Ile Ser Ser Asn Pro Gly Leu
         35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asp Tyr Gly
 65                  70                  75                  80

Ser Ala Gly Gln Ala Thr Gln Ile Val Gly Gln Ser Ala
                 85                  90
```

<210> SEQ ID NO 75
<211> LENGTH: 98
<212> TYPE: PRT
<213> ORGANISM: Nephila clavipes

<400> SEQUENCE: 75

```
Ser Arg Leu Ser Ser Pro Gln Ala Ser Ser Arg Val Ser Ala Val
 1               5                  10                  15

Ser Asn Leu Val Ala Ser Gly Pro Thr Asn Ser Ala Ala Leu Ser Ser
                 20                  25                  30

Thr Ile Ser Asn Val Val Ser Gln Ile Gly Ala Ser Asn Pro Gly Leu
         35                  40                  45

Ser Gly Cys Asp Val Leu Ile Gln Ala Leu Leu Glu Val Val Ser Ala
 50                  55                  60

Leu Ile Gln Ile Leu Gly Ser Ser Ile Gly Gln Val Asn Tyr Gly
 65                  70                  75                  80

Ser Ala Gly Gln Ala Thr Gln Ile Val Gly Gln Ser Val Tyr Gln Ala
                 85                  90                  95

Leu Gly
```

<210> SEQ ID NO 76
<211> LENGTH: 89
<212> TYPE: PRT
<213> ORGANISM: Nephila pilipes

<400> SEQUENCE: 76

```
Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Asn
                 20                  25                  30

Thr Ile Ser Asn Val Val Ser Gln Ile Ser Ser Asn Pro Gly Leu
         35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln Ile Val
                 85
```

<210> SEQ ID NO 77
<211> LENGTH: 87
<212> TYPE: PRT
<213> ORGANISM: Nephila madagascariensis

<400> SEQUENCE: 77

```
Ser Arg Leu Ser Ser Pro Gln Ala Ser Ser Arg Val Ser Ser Ala Val
 1               5                  10                  15

Ser Asn Leu Val Ala Ser Gly Pro Thr Asn Ser Ala Ala Leu Ser Ser
                 20                  25                  30
```

-continued

Thr Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Val Val Ser Ala
 50                  55                  60

Leu Ile His Ile Leu Gly Ser Ser Ile Gly Gln Val Asn Tyr Gly
 65                  70                  75                  80

Ser Ala Gly Gln Ala Thr Gln
                85

<210> SEQ ID NO 78
<211> LENGTH: 87
<212> TYPE: PRT
<213> ORGANISM: Nephila senegalensis

<400> SEQUENCE: 78

Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Ser
            20                  25                  30

Thr Ile Ser Asn Val Val Ser Gln Ile Gly Ala Ser Asn Pro Gly Leu
            35                  40                  45

Ser Gly Cys Asp Val Leu Ile Gln Ala Leu Leu Glu Val Val Ser Ala
 50                  55                  60

Leu Val His Ile Leu Gly Ser Ser Ile Gly Gln Val Asn Tyr Gly
 65                  70                  75                  80

Ser Ala Gly Gln Ala Thr Gln
                85

<210> SEQ ID NO 79
<211> LENGTH: 89
<212> TYPE: PRT
<213> ORGANISM: Octonoba varians

<400> SEQUENCE: 79

Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Ser Asn
            20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
 50                  55                  60

Pro Ile His Ile Leu Gly Ser Ser Ile Gly Gln Val Asn Tyr Gly
 65                  70                  75                  80

Ser Ala Gly Gln Ala Thr Gln Ile Val
                85

<210> SEQ ID NO 80
<211> LENGTH: 89
<212> TYPE: PRT
<213> ORGANISM: Psechrus sinensis

<400> SEQUENCE: 80

Ser Arg Leu Ser Ser Pro Glu Ala Ser Ser Arg Val Ser Ser Ala Val
 1               5                  10                  15

Ser Asn Leu Val Ser Ser Gly Pro Thr Asn Ser Ala Ala Leu Pro Asn
            20                  25                  30

Thr Ile Ser Asn Val Val Ser Gln Ile Ser Ser Asn Pro Gly Leu
            35                  40                  45

Ser Gly Cys Asp Val Leu Val Gln Ala Leu Leu Glu Val Val Ser Ala
 50                  55                  60

Leu Ile His Ile Leu Gly Ser Ser Ile Gly Gln Val Asn Tyr Gly
65                  70                  75                  80

Ser Ala Gly Gln Ala Thr Gln Ile Val
                85

<210> SEQ ID NO 81
<211> LENGTH: 88
<212> TYPE: PRT
<213> ORGANISM: Tetragnatha kauaiensis

<400> SEQUENCE: 81

Ser Leu Leu Ser Ser Pro Ala Ser Asn Ala Arg Ile Ser Ser Ala Val
1               5                   10                  15

Ser Ala Leu Ala Ser Gly Ala Ala Ser Gly Pro Gly Tyr Leu Ser Ser
                20                  25                  30

Val Ile Ser Asn Val Val Ser Gln Val Ser Ser Asn Ser Gly Gly Leu
            35                  40                  45

Val Gly Cys Asp Thr Leu Val Gln Ala Leu Leu Glu Ala Ala Ala Ala
 50                  55                  60

Leu Val His Val Leu Ala Ser Ser Gly Gly Gln Val Asn Leu Asn
65                  70                  75                  80

Thr Ala Gly Tyr Thr Ser Gln Leu
                85

<210> SEQ ID NO 82
<211> LENGTH: 88
<212> TYPE: PRT
<213> ORGANISM: Tetragnatha versicolor

<400> SEQUENCE: 82

Ser Arg Leu Ser Ser Pro Ala Ser Asn Ala Arg Ile Ser Ser Ala Val
1               5                   10                  15

Ser Ala Leu Ala Ser Gly Gly Ala Ser Ser Pro Gly Tyr Leu Ser Ser
                20                  25                  30

Ile Ile Ser Asn Val Val Ser Gln Val Ser Ser Asn Asn Asp Gly Leu
            35                  40                  45

Ser Gly Cys Asp Thr Val Val Gln Ala Leu Leu Glu Val Ala Ala Ala
 50                  55                  60

Leu Val His Val Leu Ala Ser Ser Asn Ile Gly Gln Val Asn Leu Asn
65                  70                  75                  80

Thr Ala Gly Tyr Thr Ser Gln Leu
                85

<210> SEQ ID NO 83
<211> LENGTH: 89
<212> TYPE: PRT
<213> ORGANISM: Araneus bicentenarius

<400> SEQUENCE: 83

Ser Arg Leu Ser Ser Ser Ala Ala Ser Ser Arg Val Ser Ser Ala Val
1               5                   10                  15

Ser Ser Leu Val Ser Ser Gly Pro Thr Thr Pro Ala Ala Leu Ser Asn
                20                  25                  30

Thr Ile Ser Ser Ala Val Ser Gln Ile Ser Ala Ser Asn Pro Gly Leu

```
            35                  40                  45
Ser Gly Cys Asp Val Leu Val Gln Ala Leu Leu Glu Val Val Ser Ala
            50                  55                  60
Leu Val His Ile Leu Gly Ser Ser Val Gly Gln Ile Asn Tyr Gly
 65                  70                  75                  80
Ala Ser Ala Gln Tyr Ala Gln Met Val
                 85
```

<210> SEQ ID NO 84
<211> LENGTH: 97
<212> TYPE: PRT
<213> ORGANISM: Argiope amoena

<400> SEQUENCE: 84

```
Arg Leu Ser Ser Pro Gln Ala Ser Ser Arg Val Ser Ser Ala Val Ser
  1               5                  10                  15
Thr Leu Val Ser Ser Gly Pro Thr Asn Pro Ala Ser Leu Ser Asn Ala
                 20                  25                  30
Ile Gly Ser Val Val Ser Gln Val Ser Ala Ser Asn Pro Gly Leu Pro
             35                  40                  45
Ser Cys Asp Val Leu Val Gln Ala Leu Leu Glu Ile Val Ser Ala Leu
         50                  55                  60
Val His Ile Leu Gly Ser Ser Ile Gly Gln Ile Asn Tyr Ser Ala
 65                  70                  75                  80
Ser Ser Gln Tyr Ala Arg Leu Val Gly Gln Ser Ile Ala Gln Ala Leu
                 85                  90                  95
Gly
```

<210> SEQ ID NO 85
<211> LENGTH: 82
<212> TYPE: PRT
<213> ORGANISM: Argiope aurantia

<400> SEQUENCE: 85

```
Ser Arg Leu Ser Ser Pro Gln Ala Ser Ser Arg Val Ser Ser Ala Val
  1               5                  10                  15
Ser Thr Leu Val Ser Ser Gly Pro Thr Asn Pro Ala Ala Leu Ser Asn
                 20                  25                  30
Ala Ile Ser Ser Val Val Ser Gln Val Ser Ala Ser Asn Pro Gly Leu
             35                  40                  45
Ser Gly Cys Asp Val Leu Val Gln Ala Leu Leu Glu Leu Val Ser Ala
         50                  55                  60
Leu Val His Ile Leu Gly Ser Ser Ile Gly Gln Ile Asn Tyr Ala
 65                  70                  75                  80
Ala Ser
```

<210> SEQ ID NO 86
<211> LENGTH: 98
<212> TYPE: PRT
<213> ORGANISM: Argiope trifasciata

<400> SEQUENCE: 86

```
Ser Arg Leu Ser Ser Pro Gln Ala Ser Ser Arg Val Ser Ser Ala Val
  1               5                  10                  15
Ser Thr Leu Val Ser Ser Gly Pro Thr Asn Pro Ala Ser Leu Ser Asn
                 20                  25                  30
Ala Ile Ser Ser Val Val Ser Gln Val Ser Ser Asn Pro Gly Leu
```

```
                35                  40                  45
Ser Gly Cys Asp Val Leu Val Gln Ala Leu Leu Glu Ile Val Ser Ala
         50                  55                  60
Leu Val His Ile Leu Gly Ser Ser Ile Gly Gln Ile Asn Tyr Ala
 65                  70                  75                  80
Ala Ser Ser Gln Tyr Ala Gln Leu Val Gly Ser Leu Thr Gln Ala
                 85                  90                  95
Leu Gly

<210> SEQ ID NO 87
<211> LENGTH: 89
<212> TYPE: PRT
<213> ORGANISM: Gasteracantha mammosa

<400> SEQUENCE: 87

Ser Arg Leu Ser Ser Pro Gln Ala Gly Ala Arg Val Ser Ser Ala Val
 1               5                  10                  15
Ser Ala Leu Val Ala Ser Gly Pro Thr Ser Pro Ala Ala Val Ser Ser
                 20                  25                  30
Ala Ile Ser Asn Val Ala Ser Gln Ile Ser Ala Ser Asn Pro Gly Leu
                 35                  40                  45
Ser Gly Cys Asp Val Leu Val Gln Ala Leu Leu Glu Ile Val Ser Ala
         50                  55                  60
Leu Val Ser Ile Leu Ser Ser Ala Ser Ile Gly Gln Ile Asn Tyr Gly
 65                  70                  75                  80
Ala Ser Gly Gln Tyr Ala Ala Met Ile
                 85

<210> SEQ ID NO 88
<211> LENGTH: 90
<212> TYPE: PRT
<213> ORGANISM: Latrodectus geometricus

<400> SEQUENCE: 88

Ser Ala Leu Ser Ser Pro Thr Thr His Ala Arg Ile Ser Ser His Ala
 1               5                  10                  15
Ser Thr Leu Leu Ser Ser Gly Pro Thr Asn Ser Ala Ala Ile Ser Asn
                 20                  25                  30
Val Ile Ser Asn Ala Val Ser Gln Val Ser Ala Ser Asn Pro Gly Ser
                 35                  40                  45
Ser Ser Cys Asp Val Leu Val Gln Ala Leu Leu Glu Leu Ile Thr Ala
         50                  55                  60
Leu Ile Ser Ile Val Asp Ser Ser Asn Ile Gly Gln Val Asn Tyr Gly
 65                  70                  75                  80
Ser Ser Gly Gln Tyr Ala Gln Met Val Gly
                 85                  90

<210> SEQ ID NO 89
<211> LENGTH: 98
<212> TYPE: PRT
<213> ORGANISM: Latrodectus hesperus

<400> SEQUENCE: 89

Ser Ala Leu Ser Ser Pro Thr Thr His Ala Arg Ile Ser Ser His Ala
 1               5                  10                  15
Ser Thr Leu Leu Ser Ser Gly Pro Thr Asn Ala Ala Ala Leu Ser Asn
                 20                  25                  30
```

```
Val Ile Ser Asn Ala Val Ser Gln Val Ser Ala Ser Asn Pro Gly Ser
            35                  40                  45

Ser Ser Cys Asp Val Leu Val Gln Ala Leu Leu Glu Ile Ile Thr Ala
 50                      55                  60

Leu Ile Ser Ile Leu Asp Ser Ser Val Gly Gln Val Asn Tyr Gly
 65                  70                  75                  80

Ser Ser Gly Gln Tyr Ala Gln Ile Val Gly Gln Ser Met Gln Gln Ala
                85                  90                  95

Met Gly

<210> SEQ ID NO 90
<211> LENGTH: 97
<212> TYPE: PRT
<213> ORGANISM: Nephila clavipes

<400> SEQUENCE: 90

Ser Arg Leu Ala Ser Pro Asp Ser Gly Ala Arg Val Ala Ser Ala Val
 1               5                  10                  15

Ser Asn Leu Val Ser Ser Gly Pro Thr Ser Ser Ala Ala Leu Ser Ser
                20                  25                  30

Val Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Ile Val Ser Ala
 50                      55                  60

Cys Val Thr Ile Leu Ser Ser Ser Ile Gly Gln Val Asn Tyr Gly
 65                  70                  75                  80

Ala Ala Ser Gln Phe Ala Gln Val Val Gly Gln Ser Val Leu Ser Ala
                85                  90                  95

Phe

<210> SEQ ID NO 91
<211> LENGTH: 82
<212> TYPE: PRT
<213> ORGANISM: Nephila madagascariensis

<400> SEQUENCE: 91

Ser Arg Leu Ala Ser Pro Asp Ser Gly Ala Arg Val Ala Ser Ala Val
 1               5                  10                  15

Ser Asn Leu Val Ser Ser Gly Pro Thr Ser Ser Ala Ala Leu Ser Ser
                20                  25                  30

Val Ile Ser Asn Ala Val Ser Gln Ile Gly Ala Ser Asn Pro Gly Leu
            35                  40                  45

Ser Gly Cys Asp Val Leu Ile Gln Ala Leu Leu Glu Ile Val Ser Ala
 50                      55                  60

Cys Val Thr Ile Leu Ser Ser Ser Ile Gly Gln Val Asn Tyr Gly
 65                  70                  75                  80

Ala Ala

<210> SEQ ID NO 92
<211> LENGTH: 82
<212> TYPE: PRT
<213> ORGANISM: Nephila senegalensis
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (56)..(56)
```

<223> OTHER INFORMATION: Xaa can be any naturally occurring amino acid

<400> SEQUENCE: 92

```
Ser Arg Leu Ala Ser Pro Asp Ser Gly Ala Arg Val Ala Ser Ala Val
1               5                   10                  15

Ser Asn Leu Val Ser Ser Gly Pro Thr Ser Ser Ala Ala Leu Ser Ser
            20                  25                  30

Val Ile Xaa Asn Ala Val Ser Gln Ile Gly Ala Ser Asn Pro Gly Leu
        35                  40                  45

Ser Gly Cys Asp Val Leu Ile Xaa Ala Leu Leu Glu Ile Val Ser Ala
    50                  55                  60

Cys Val Thr Ile Leu Ser Ser Ser Ile Gly Gln Val Asn Tyr Gly
65                  70                  75                  80

Ala Ala
```

<210> SEQ ID NO 93
<211> LENGTH: 71
<212> TYPE: PRT
<213> ORGANISM: Dolomedes tenebrosus

<400> SEQUENCE: 93

```
Ser Arg Leu Ser Ser Pro Glu Ala Ala Ser Arg Val Ser Ser Ala Val
1               5                   10                  15

Ser Ser Leu Val Ser Asn Gly Gln Val Asn Val Asp Ala Leu Pro Ser
            20                  25                  30

Ile Ile Ser Asn Leu Ser Ser Ser Ile Ser Ala Ser Ala Thr Thr Ala
        35                  40                  45

Ser Asp Cys Glu Val Leu Val Gln Val Leu Leu Glu Val Val Ser Ala
    50                  55                  60

Leu Val Gln Ile Val Cys Ser
65                  70
```

<210> SEQ ID NO 94
<211> LENGTH: 97
<212> TYPE: PRT
<213> ORGANISM: Dolomedes tenebrosus

<400> SEQUENCE: 94

```
Ser Arg Leu Ser Ser Pro Gln Ala Ala Ser Arg Val Ser Ser Ala Val
1               5                   10                  15

Ser Ser Leu Val Ser Asn Gly Gln Val Asn Val Ala Ala Leu Pro Ser
            20                  25                  30

Ile Ile Ser Ser Leu Ser Ser Ser Ile Ser Ala Ser Ser Thr Ala Ala
        35                  40                  45

Ser Asp Cys Glu Val Leu Val Gln Val Leu Leu Glu Ile Val Ser Ala
    50                  55                  60

Leu Val Gln Ile Val Ser Ser Ala Asn Val Gly Tyr Ile Asn Pro Glu
65                  70                  75                  80

Ala Ser Gly Ser Leu Asn Ala Val Gly Ser Ala Leu Ala Ala Ala Met
                85                  90                  95

Gly
```

<210> SEQ ID NO 95
<211> LENGTH: 93
<212> TYPE: PRT
<213> ORGANISM: Araneus diadematus

<400> SEQUENCE: 95

```
Asn Arg Leu Ser Ser Ala Gly Ala Ala Ser Arg Val Ser Asn Val
1               5                   10                  15

Ala Ala Ile Ala Ser Ala Gly Ala Ala Leu Pro Asn Val Ile Ser
            20                  25                  30

Asn Ile Tyr Ser Gly Val Leu Ser Ser Gly Val Ser Ser Glu Ala
        35                  40                  45

Leu Ile Gln Ala Leu Leu Glu Val Ile Ser Ala Leu Ile His Val Leu
50                  55                  60

Gly Ser Ala Ser Ile Gly Asn Val Ser Val Gly Val Asn Ser Ala
65              70                  75                  80

Leu Asn Ala Val Gln Asn Ala Val Gly Ala Tyr Ala Gly
                85                  90

<210> SEQ ID NO 96
<211> LENGTH: 98
<212> TYPE: PRT
<213> ORGANISM: Araneus diadematus

<400> SEQUENCE: 96

Ser Arg Leu Ser Ser Pro Ser Ala Ala Ala Arg Val Ser Ala Val
1               5                   10                  15

Ser Leu Val Ser Asn Gly Gly Pro Thr Ser Pro Ala Ala Leu Ser Ser
            20                  25                  30

Ser Ile Ser Asn Val Val Ser Gln Ile Ser Ala Ser Asn Pro Gly Leu
        35                  40                  45

Ser Gly Cys Asp Ile Leu Val Gln Ala Leu Leu Glu Ile Ile Ser Ala
50                  55                  60

Leu Val His Ile Leu Gly Ser Ala Asn Ile Gly Pro Val Asn Ser Ser
65              70                  75                  80

Ser Ala Gly Gln Ser Ala Ser Ile Val Gly Gln Ser Val Tyr Arg Ala
                85                  90                  95

Leu Ser

<210> SEQ ID NO 97
<211> LENGTH: 98
<212> TYPE: PRT
<213> ORGANISM: Araneus diadematus

<400> SEQUENCE: 97

Ser Arg Leu Ser Ser Pro Ala Ala Ser Ser Arg Val Ser Ala Val
1               5                   10                  15

Ser Ser Leu Val Ser Ser Gly Pro Thr Lys His Ala Ala Leu Ser Asn
            20                  25                  30

Thr Ile Ser Ser Val Val Ser Gln Val Ser Ala Ser Asn Pro Gly Leu
        35                  40                  45

Ser Gly Cys Asp Val Leu Val Gln Ala Leu Leu Glu Val Val Ser Ala
50                  55                  60

Leu Val Ser Ile Leu Gly Ser Ser Ser Ile Gly Gln Ile Asn Tyr Gly
65              70                  75                  80

Ala Ser Ala Gln Tyr Thr Gln Met Val Gly Gln Ser Val Ala Gln Ala
                85                  90                  95

Leu Ala

<210> SEQ ID NO 98
<211> LENGTH: 94
<212> TYPE: PRT
```

<213> ORGANISM: Araneus diadematus

<400> SEQUENCE: 98

Ser Val Tyr Leu Arg Leu Gln Pro Arg Leu Glu Val Ser Ser Ala Val
1               5                   10                  15

Ser Ser Leu Val Ser Ser Gly Pro Thr Asn Gly Ala Ala Val Ser Gly
            20                  25                  30

Ala Leu Asn Ser Leu Val Ser Gln Ile Ser Ala Ser Asn Pro Gly Leu
        35                  40                  45

Ser Gly Cys Asp Ala Leu Val Gln Ala Leu Leu Glu Leu Val Ser Ala
    50                  55                  60

Leu Val Ala Ile Leu Ser Ser Ala Ser Ile Gly Gln Val Asn Val Ser
65                  70                  75                  80

Ser Val Ser Gln Ser Thr Gln Met Ile Ser Gln Ala Leu Ser
                85                  90

<210> SEQ ID NO 99
<211> LENGTH: 79
<212> TYPE: PRT
<213> ORGANISM: Homo sapiens
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 99

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met
65                  70                  75

<210> SEQ ID NO 100
<211> LENGTH: 79
<212> TYPE: PRT
<213> ORGANISM: Mus musculus
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 100

```
Leu Pro Ile Pro Leu Pro Phe Cys Trp Leu Cys Arg Thr Leu Ile Lys
1               5                   10                  15

Arg Val Gln Ala Val Ile Pro Lys Gly Val Leu Ala Val Ala Val Ser
                20                  25                  30

Gln Val Cys His Val Val Pro Leu Val Val Gly Gly Ile Cys Gln Cys
            35                  40                  45

Leu Ala Glu Arg Tyr Thr Val Leu Leu Asp Ala Leu Leu Gly Arg
        50                  55                  60

Val Val Pro Gln Leu Val Cys Gly Leu Val Leu Arg Cys Ser Thr
65                  70                  75

<210> SEQ ID NO 101
<211> LENGTH: 79
<212> TYPE: PRT
<213> ORGANISM: Sus scrofa
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 101

Phe Pro Ile Pro Leu Pro Phe Cys Trp Leu Cys Arg Thr Leu Ile Lys
1               5                   10                  15

Arg Ile Gln Ala Val Val Pro Lys Gly Val Leu Leu Lys Ala Val Ala
                20                  25                  30

Gln Val Cys His Val Val Pro Leu Pro Val Gly Gly Ile Cys Gln Cys
            35                  40                  45

Leu Ala Glu Arg Tyr Ile Val Ile Cys Leu Asn Met Leu Leu Asp Arg
        50                  55                  60

Thr Leu Pro Gln Leu Val Cys Gly Leu Val Leu Arg Cys Ser Ser
65                  70                  75

<210> SEQ ID NO 102
<211> LENGTH: 79
<212> TYPE: PRT
<213> ORGANISM: Oryctolagus cuniculus
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 102

Phe Pro Ile Pro Leu Pro Leu Cys Trp Leu Cys Arg Thr Leu Leu Lys
1               5                   10                  15

Arg Ile Gln Ala Met Ile Pro Lys Gly Val Leu Ala Met Ala Val Ala
                20                  25                  30

Gln Val Cys His Val Val Pro Leu Val Val Gly Gly Ile Cys Gln Cys
```

```
                35                  40                  45
Leu Ala Glu Arg Tyr Thr Val Ile Leu Leu Glu Val Leu Leu Gly His
        50                  55                  60

Val Leu Pro Gln Leu Val Cys Gly Leu Val Leu Arg Cys Ser Ser
65                  70                  75

<210> SEQ ID NO 103
<211> LENGTH: 79
<212> TYPE: PRT
<213> ORGANISM: Rattus norvegicus
<220> FEATURE:
<221> NAME/KEY: DISULFID
<222> LOCATION: (8)..(77)
<220> FEATURE:
<221> NAME/KEY: DISULFID
<222> LOCATION: (11)..(71)
<220> FEATURE:
<221> NAME/KEY: DISULFID
<222> LOCATION: (35)..(46)
<220> FEATURE:
<221> NAME/KEY: DISULFID
<222> LOCATION: (48)..(48)
<223> OTHER INFORMATION: Intermolecular Cys48-Cys48 linkage

<400> SEQUENCE: 103

Leu Pro Ile Pro Leu Pro Phe Cys Trp Leu Cys Arg Thr Leu Ile Lys
1               5                   10                  15

Arg Val Gln Ala Val Ile Pro Lys Gly Val Leu Ala Val Ala Val Ser
            20                  25                  30

Gln Val Cys His Val Val Pro Leu Val Val Gly Gly Ile Cys Gln Cys
        35                  40                  45

Leu Ala Glu Arg Tyr Thr Val Leu Leu Leu Asp Ala Leu Leu Gly Arg
    50                  55                  60

Val Val Pro Gln Leu Val Cys Gly Leu Val Leu Arg Cys Ser Thr
65                  70                  75

<210> SEQ ID NO 104
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)
<220> FEATURE:
<221> NAME/KEY: DISULFID
<222> LOCATION: (4)..(27)

<400> SEQUENCE: 104

Cys Trp Leu Cys Arg Ala Leu Ile Lys Arg Ile Gln Ala Met Ile Pro
1               5                   10                  15

Lys Gly Gly Arg Met Leu Pro Gln Leu Val Cys Arg Leu Val Leu Arg
            20                  25                  30

Cys Ser

<210> SEQ ID NO 105
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)
<220> FEATURE:
```

<221> NAME/KEY: DISULFID
<222> LOCATION: (4)..(27)

<400> SEQUENCE: 105

Cys Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser

<210> SEQ ID NO 106
<211> LENGTH: 27
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(27)
<220> FEATURE:
<221> NAME/KEY: DISULFID
<222> LOCATION: (4)..(21)

<400> SEQUENCE: 106

Cys Leu Leu Cys Arg Ala Leu Ile Lys Arg Phe Asn Arg Tyr Leu Thr
1               5                   10                  15

Pro Gln Leu Val Cys Arg Leu Val Leu Arg Cys
            20                  25

<210> SEQ ID NO 107
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)

<400> SEQUENCE: 107

Cys Trp Leu Ala Arg Ala Leu Ile Lys Arg Ile Gln Ala Leu Ile Pro
1               5                   10                  15

Lys Gly Gly Arg Leu Leu Pro Gln Leu Val Ala Arg Leu Val Leu Arg
            20                  25                  30

Cys Ser

<210> SEQ ID NO 108
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (4)..(27)

<400> SEQUENCE: 108

Ala Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Ala Ser

<210> SEQ ID NO 109

<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (1)..(33)

<400> SEQUENCE: 109

Cys Trp Leu Leu Arg Ala Leu Ile Lys Arg Ile Gln Ala Leu Ile Pro
 1               5                  10                  15

Lys Gly Gly Arg Leu Leu Pro Gln Leu Val Leu Arg Leu Val Leu Arg
             20                  25                  30

Cys Ser

<210> SEQ ID NO 110
<211> LENGTH: 34
<212> TYPE: PRT
<213> ORGANISM: Artificial Sequence
<220> FEATURE:
<223> OTHER INFORMATION: Construct derived from SP-B
<220> FEATURE:
<221> NAME/KEY: DISULFID
<222> LOCATION: (4)..(27)

<400> SEQUENCE: 110

Leu Trp Leu Cys Arg Ala Leu Ile Lys Arg Ile Gln Ala Leu Ile Pro
 1               5                  10                  15

Lys Gly Gly Arg Leu Leu Pro Gln Leu Val Cys Arg Leu Val Leu Arg
             20                  25                  30

Leu Ser

<210> SEQ ID NO 111
<211> LENGTH: 35
<212> TYPE: PRT
<213> ORGANISM: Homo sapiens

<400> SEQUENCE: 111

Phe Gly Ile Pro Cys Cys Pro Val His Leu Lys Arg Leu Leu Ile Val
 1               5                  10                  15

Val Val Val Val Val Leu Ile Val Val Val Ile Val Gly Ala Leu Leu
             20                  25                  30

Met Gly Leu
        35

<210> SEQ ID NO 112
<211> LENGTH: 35
<212> TYPE: PRT
<213> ORGANISM: Artificial Sequence
<220> FEATURE:
<223> OTHER INFORMATION: Construct derived from SP-C

<400> SEQUENCE: 112

Phe Gly Ile Pro Ser Ser Pro Val His Leu Lys Arg Leu Lys Leu Leu
 1               5                  10                  15

Leu Leu Leu Leu Leu Leu Ile Leu Leu Leu Ile Leu Gly Ala Leu Leu
             20                  25                  30

Met Gly Leu
        35

<210> SEQ ID NO 113
<211> LENGTH: 33

```
<212> TYPE: PRT
<213> ORGANISM: Artificial Sequence
<220> FEATURE:
<223> OTHER INFORMATION: Construct derived from SP-C

<400> SEQUENCE: 113

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Met Gly
            20                  25                  30

Leu

<210> SEQ ID NO 114
<211> LENGTH: 30
<212> TYPE: PRT
<213> ORGANISM: Artificial Sequence
<220> FEATURE:
<223> OTHER INFORMATION: Construct derived from SP-C

<400> SEQUENCE: 114

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu
            20                  25                  30

<210> SEQ ID NO 115
<211> LENGTH: 33
<212> TYPE: PRT
<213> ORGANISM: Artificial Sequence
<220> FEATURE:
<223> OTHER INFORMATION: Construct derived from SP-C

<400> SEQUENCE: 115

Ile Pro Ser Ser Pro Val His Leu Lys Arg Leu Lys Leu Leu Leu
1               5                   10                  15

Leu Leu Leu Leu Ile Leu Leu Leu Ile Leu Gly Ala Leu Leu Leu Gly
            20                  25                  30

Leu

<210> SEQ ID NO 116
<211> LENGTH: 37
<212> TYPE: PRT
<213> ORGANISM: Homo sapiens

<400> SEQUENCE: 116

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 117
<211> LENGTH: 21
<212> TYPE: PRT
<213> ORGANISM: Artificial Sequence
<220> FEATURE:
<223> OTHER INFORMATION: Construct derived from SP-B

<400> SEQUENCE: 117

Lys Leu Leu Leu Leu Lys Leu Leu Leu Leu Lys Leu Leu Leu Leu Lys
1               5                   10                  15
```

```
Leu Leu Leu Leu Lys
            20

<210> SEQ ID NO 118
<211> LENGTH: 34
<212> TYPE: PRT
<213> ORGANISM: Artificial Sequence
<220> FEATURE:
<223> OTHER INFORMATION: Construct derived from SP-B

<400> SEQUENCE: 118

Ala Trp Leu Ala Arg Ala Leu Ile Lys Arg Ile Gln Ala Leu Ile Pro
1               5                   10                  15

Lys Gly Gly Arg Leu Leu Pro Gln Leu Val Ala Arg Leu Val Leu Arg
            20                  25                  30

Ala Ser

<210> SEQ ID NO 119
<211> LENGTH: 34
<212> TYPE: PRT
<213> ORGANISM: Artificial Sequence
<220> FEATURE:
<223> OTHER INFORMATION: Construct derived from SP-B

<400> SEQUENCE: 119

Leu Trp Leu Leu Arg Ala Leu Ile Lys Arg Ile Gln Ala Leu Ile Pro
1               5                   10                  15

Lys Gly Gly Arg Leu Leu Pro Gln Leu Val Leu Arg Leu Val Leu Arg
            20                  25                  30

Leu Ser

<210> SEQ ID NO 120
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 120

Xaa Leu Glu Thr Leu Phe Gln Gly Xaa
1               5
```